(12) United States Patent
Meyer et al.

(10) Patent No.: US 9,981,106 B2
(45) Date of Patent: May 29, 2018

(54) OSCILLATING POSITIVE EXPIRATORY PRESSURE DEVICE

(71) Applicant: Trudell Medical International, London (CA)

(72) Inventors: Adam Meyer, London (CA); Dan Engelbreth, London (CA)

(73) Assignee: TRUDELL MEDICAL INTERNATIONAL, London Ontario (CA)

( * ) Notice: Subject to any disclaimer, the term of this patent is extended or adjusted under 35 U.S.C. 154(b) by 1 day.

(21) Appl. No.: 15/143,092

(22) Filed: Apr. 29, 2016

(65) Prior Publication Data
US 2016/0310695 A1 Oct. 27, 2016

Related U.S. Application Data

(63) Continuation of application No. 13/489,894, filed on Jun. 6, 2012, now Pat. No. 9,358,417.
(Continued)

(51) Int. Cl.
*A61M 16/20* (2006.01)
*A61M 16/00* (2006.01)
(Continued)

(52) U.S. Cl.
CPC .......... *A61M 16/208* (2013.01); *A61M 11/00* (2013.01); *A61M 15/009* (2013.01);
(Continued)

(58) Field of Classification Search
CPC .............. A63B 21/00196; A63B 23/18; A63B 2071/0694; A63B 23/185; A61M 16/0006;
(Continued)

(56) References Cited

U.S. PATENT DOCUMENTS

| 393,869 A | 12/1888 | Warren |
|---|---|---|
| 938,808 A | 11/1909 | Yount |

(Continued)

FOREIGN PATENT DOCUMENTS

| EP | 0 372 148 A1 | 3/1990 |
|---|---|---|
| EP | 0 678 306 A2 | 10/1995 |

(Continued)

OTHER PUBLICATIONS

U.S. Appl. No. 14/329,011, filed Jul. 11, 2014, Costella, et al.
(Continued)

*Primary Examiner* — Todd J Scherbel
*Assistant Examiner* — Elliot S Ruddie
(74) *Attorney, Agent, or Firm* — Brinks Gilson & Lione

(57) ABSTRACT

A respiratory treatment device comprising at least one chamber, a chamber inlet configured to receive exhaled air into the at least one chamber, at least one chamber outlet configured to permit exhaled air to exit the at least one chamber, and an exhalation flow path defined between the chamber inlet and the at least one chamber outlet. A restrictor member positioned in the exhalation flow path is moveable between a closed position, where a flow of exhaled air along the exhalation flow path is restricted, and an open position, where the flow of exhaled air along the exhalation flow path is less restricted. A vane in fluid communication with the exhalation flow path is operatively connected to the restrictor member and is configured to reciprocate between a first position and a second position in response to the flow of exhaled air along the exhalation flow path.

21 Claims, 60 Drawing Sheets

Related U.S. Application Data

(60) Provisional application No. 61/532,951, filed on Sep. 9, 2011, provisional application No. 61/493,816, filed on Jun. 6, 2011.

(51) Int. Cl.

| | | |
|---|---|---|
| *A63B 23/18* | (2006.01) | |
| *A61M 16/08* | (2006.01) | |
| *A61M 15/00* | (2006.01) | |
| *A61M 16/04* | (2006.01) | |
| *A61M 16/06* | (2006.01) | |
| *A63B 21/00* | (2006.01) | |
| *A61M 11/00* | (2006.01) | |
| *A63B 71/06* | (2006.01) | |

(52) U.S. Cl.
CPC ........ *A61M 16/0006* (2014.02); *A61M 16/04* (2013.01); *A61M 16/06* (2013.01); *A61M 16/0866* (2014.02); *A63B 21/00196* (2013.01); *A63B 23/18* (2013.01); *A61M 15/00* (2013.01); *A63B 2071/0694* (2013.01)

(58) Field of Classification Search
CPC .............. A61M 16/0866; A61M 15/00; A61M 16/208; A61B 5/0875; A61B 5/0876; A61B 5/09
USPC ................ 128/203.12, 204.25; 600/538, 539
See application file for complete search history.

(56) References Cited

U.S. PATENT DOCUMENTS

| | | |
|---|---|---|
| 2,670,739 A | 3/1954 | NcNeill |
| 2,918,917 A | 12/1959 | Emerson |
| 3,710,780 A | 1/1973 | Milch |
| 3,908,987 A | 9/1975 | Boehringer |
| 4,054,134 A | 10/1977 | Kritzer |
| 4,062,358 A | 12/1977 | Kritzer |
| 4,182,366 A | 1/1980 | Boehringer |
| 4,198,969 A | 4/1980 | Virag |
| 4,221,381 A | 9/1980 | Ericson |
| 4,226,233 A | 10/1980 | Kritzer |
| 4,231,375 A | 11/1980 | Boehringer et al. |
| 4,267,832 A | 5/1981 | Hakkinen |
| 4,275,722 A | 6/1981 | Sorensen |
| 4,298,023 A | 11/1981 | McGinnis |
| 4,327,740 A | 5/1982 | Shuman |
| 4,403,616 A | 9/1983 | King |
| 4,436,090 A | 3/1984 | Darling |
| 4,470,412 A | 9/1984 | Nowacki et al. |
| 4,601,465 A | 7/1986 | Roy |
| 4,611,591 A | 9/1986 | Inui et al. |
| 4,635,631 A | 1/1987 | Izumi |
| 4,651,731 A | 3/1987 | Vicenzi et al. |
| 4,739,987 A | 4/1988 | Nicholson |
| 4,770,413 A | 9/1988 | Green |
| 4,973,047 A | 11/1990 | Norell |
| 4,981,295 A | 1/1991 | Belman et al. |
| 5,018,517 A | 5/1991 | Liardet |
| 5,042,467 A | 8/1991 | Foley |
| 5,065,746 A | 11/1991 | Steen |
| 5,193,529 A | 3/1993 | Labaere |
| 5,345,930 A | 9/1994 | Cardinal et al. |
| 5,381,789 A | 1/1995 | Marquardt |
| 5,451,190 A | 9/1995 | Liardet |
| 5,479,920 A | 1/1996 | Piper et al. |
| 5,540,220 A | 7/1996 | Gropper et al. |
| 5,569,122 A | 10/1996 | Cegla |
| 5,570,682 A | 11/1996 | Johnson |
| 5,598,839 A | 2/1997 | Niles et al. |
| 5,613,489 A | 3/1997 | Miller |
| 5,645,049 A | 7/1997 | Foley et al. |
| 5,647,345 A | 7/1997 | Saul |
| 5,655,520 A | 8/1997 | Howe |
| 5,658,221 A | 8/1997 | Hougen |
| 5,791,339 A | 8/1998 | Winter |
| 5,829,429 A | 11/1998 | Hughes |
| 5,848,588 A | 12/1998 | Foley et al. |
| 5,862,802 A | 1/1999 | Bird |
| 5,890,998 A | 4/1999 | Hougen |
| 5,893,361 A | 4/1999 | Hughes |
| 5,899,832 A | 5/1999 | Hougen |
| 5,910,071 A | 6/1999 | Hougen |
| 5,925,831 A | 7/1999 | Storsved |
| 6,026,807 A | 2/2000 | Puderbaugh et al. |
| 6,044,841 A | 4/2000 | Verdun et al. |
| 6,058,932 A | 5/2000 | Hughes |
| 6,066,101 A | 5/2000 | Johnson |
| 6,067,984 A | 5/2000 | Piper |
| 6,083,141 A | 7/2000 | Hougen |
| 6,089,105 A | 7/2000 | Ricciardelli |
| 6,102,038 A | 8/2000 | DeVries |
| 6,167,881 B1 | 1/2001 | Hughes |
| 6,176,235 B1 | 1/2001 | Benarrouch et al. |
| D440,651 S | 4/2001 | Foran |
| 6,240,917 B1 | 6/2001 | Andrade |
| 6,253,766 B1 | 7/2001 | Niles |
| 6,293,279 B1 | 9/2001 | Schmidt et al. |
| 6,340,025 B1 | 1/2002 | Van Brunt |
| 6,345,617 B1 | 2/2002 | Engelbreth et al. |
| 6,412,481 B1 | 7/2002 | Bienvenu et al. |
| 6,500,095 B1 | 12/2002 | Hougen |
| 6,557,549 B2 | 5/2003 | Schmidt et al. |
| 6,581,595 B1 | 6/2003 | Murdock et al. |
| 6,581,596 B1 | 6/2003 | Truitt |
| 6,581,598 B1 | 6/2003 | Foran et al. |
| 6,581,600 B2 | 6/2003 | Bird |
| 6,595,203 B1 | 7/2003 | Bird |
| 6,606,989 B1 | 8/2003 | Brand |
| 6,615,831 B1 | 9/2003 | Truitt |
| 6,631,721 B1 | 10/2003 | Salter et al. |
| 6,659,100 B2 | 12/2003 | O'Rourke |
| 6,702,769 B1 | 3/2004 | Fowler-Hawkins |
| 6,708,690 B1 | 3/2004 | Hete et al. |
| 6,708,691 B1 | 3/2004 | Hayek |
| 6,726,598 B1 | 4/2004 | Jarvis |
| D490,519 S | 5/2004 | Pelerossi et al. |
| 6,776,159 B2 * | 8/2004 | Pelerossi ............... A61M 16/08 128/204.18 |
| 6,848,443 B2 * | 2/2005 | Schmidt ............ A61M 15/0086 128/200.23 |
| 6,851,425 B2 | 2/2005 | Jaffre |
| 6,904,906 B2 | 6/2005 | Salter |
| 6,923,181 B2 | 8/2005 | Tuck |
| 6,929,007 B2 | 8/2005 | Emerson |
| 6,984,214 B2 | 1/2006 | Fowler-Hawkins |
| 7,059,324 B2 | 6/2006 | Pelerossi et al. |
| 7,096,866 B2 | 8/2006 | Be'eri et al. |
| 7,134,434 B2 | 11/2006 | Truitt et al. |
| 7,165,547 B2 | 1/2007 | Truitt et al. |
| 7,188,621 B2 | 3/2007 | DeVries |
| 7,191,776 B2 | 3/2007 | Niles |
| 7,191,780 B2 | 3/2007 | Faram |
| 7,214,170 B2 | 5/2007 | Sumners et al. |
| 7,383,740 B2 | 6/2008 | Krasilchikov et al. |
| 7,617,821 B2 | 11/2009 | Hughes |
| 7,699,054 B2 | 4/2010 | Pelerossi et al. |
| 7,717,847 B2 | 5/2010 | Smith |
| 7,771,472 B2 | 8/2010 | Hendricksen |
| 7,779,841 B2 | 8/2010 | Dunsmore et al. |
| 7,798,148 B2 | 9/2010 | Doshi |
| 7,856,979 B2 | 12/2010 | Doshi |
| 7,909,033 B2 | 3/2011 | Faram |
| 8,006,922 B2 | 8/2011 | Katzer |
| 8,025,051 B2 | 9/2011 | Dagsland |
| 8,025,054 B2 | 9/2011 | Dunsmore et al. |
| 8,043,236 B2 | 10/2011 | Abrammerovich et al. |
| 8,051,854 B2 | 11/2011 | Faram |
| RE43,174 E | 2/2012 | Schmidt et al. |
| 8,118,024 B2 | 2/2012 | DeVries et al. |
| 8,118,713 B2 | 2/2012 | Foley et al. |
| 8,225,808 B2 | 7/2012 | Richards et al. |
| 8,327,849 B2 | 12/2012 | Grychowski et al. |

(56) References Cited

U.S. PATENT DOCUMENTS

| | | | |
|---|---|---|---|
| 8,460,223 B2 | 6/2013 | Huster et al. | |
| 8,469,029 B2 | 6/2013 | Brown et al. | |
| 8,485,179 B1 | 7/2013 | Meyer | |
| 8,539,179 B1 | 9/2013 | Meyer et al. | |
| 8,985,111 B2 | 3/2015 | Grychowski et al. | |
| D731,050 S | 6/2015 | Meyer | |
| 9,149,589 B2 | 10/2015 | Meyer et al. | |
| 9,220,855 B2 | 12/2015 | Meyer | |
| 2007/0259759 A1 | 11/2007 | Sumners et al. | |
| 2008/0053456 A1 | 3/2008 | Brown et al. | |
| 2008/0110455 A1* | 5/2008 | Dunsmore | A61M 16/00 128/200.24 |
| 2009/0241949 A1 | 10/2009 | Smutney et al. | |
| 2010/0139655 A1 | 7/2010 | Genosar | |
| 2010/0307487 A1 | 12/2010 | Dunsmore et al. | |
| 2012/0097164 A1 | 4/2012 | Rozario et al. | |
| 2012/0304988 A1 | 12/2012 | Meyer | |
| 2013/0133649 A1 | 5/2013 | Grychowski et al. | |
| 2013/0184619 A1 | 7/2013 | Von Hollen et al. | |
| 2013/0312746 A1 | 11/2013 | Grychowski | |
| 2014/0041657 A1 | 2/2014 | Meyer | |
| 2014/0150790 A1 | 6/2014 | Meyer | |
| 2015/0053209 A1 | 2/2015 | Meyer et al. | |
| 2015/0151060 A1 | 6/2015 | Grychowski et al. | |
| 2015/0224269 A1 | 8/2015 | Alizoti et al. | |
| 2015/0297848 A1 | 10/2015 | Meyer et al. | |
| 2015/0374939 A1 | 12/2015 | Meyer et al. | |
| 2016/0136369 A1 | 5/2016 | Meyer et al. | |
| 2017/0028161 A1 | 2/2017 | Meyer et al. | |
| 2017/0049979 A1 | 2/2017 | Meyer et al. | |

FOREIGN PATENT DOCUMENTS

| | | |
|---|---|---|
| EP | 1435251 | 12/2003 |
| EP | 1 464 357 A1 | 10/2004 |
| EP | 1 435 251 B1 | 6/2006 |
| EP | 1 103 287 B1 | 6/2007 |
| EP | 1 897 576 A1 | 3/2008 |
| EP | 1 908 489 A1 | 4/2008 |
| EP | 2444114 | 4/2012 |
| EP | 2455137 | 5/2012 |
| GB | 2 425 488 A | 11/2006 |
| WO | WO 1989/03707 A1 | 5/1989 |
| WO | WO 1996/40376 | 12/1996 |
| WO | WO 1999/16490 | 4/1999 |
| WO | WO 2000/27455 | 5/2000 |
| WO | WO 2007/061648 A3 | 5/2007 |
| WO | WO 2007/119104 A3 | 10/2007 |
| WO | WO 2008/063966 A1 | 5/2008 |
| WO | WO 2008/122045 A1 | 10/2008 |
| WO | WO 2009/131965 | 10/2009 |
| WO | WO 2011/058470 | 5/2011 |
| WO | WO 2012/038864 A2 | 3/2012 |
| WO | WO 2016/012740 | 1/2016 |

OTHER PUBLICATIONS

U.S. Appl. No. 14/674,494, filed Mar. 31, 2015, Meyer et al.
U.S. Appl. No. 29/524,678, filed Apr. 22, 2015, Meyer et al.
U.S. Appl. No. 29/538,317, filed Sep. 2, 2015, Engelbreth et al.
U.S. Appl. No. 29/538,323, filed Sep. 2, 2015, Engelbreth et al.
Web page entitled Bronchial Hygiene, acapella Vibratory PEP Therapy System accessed from http://www.smiths-medical.com/catalog/bronchial-hygiene/acapella/acapella.html on Jul. 7, 2009.
Web page entitled Thayer Quake accessed from http://www.thayermedical.com/quake.htm on Jul. 7, 2009.
Human growth hormone, cortisol, and acid-base balance changes after hyperventilation and breath-holding; PubMed—indexed for MEDLINE; Int J Sports Med., Dec. 1986; 7(6):311-5, Djarova T.
Bosco C, Cardinale M. & Tsarpela O (1999). Influence of vibration on mechanical power and electromyogram activity in human arm flexor muscles. Eur J Appl Physiol 79, 306-311.
David Sumners; Power Breathing and Strength; http://EzineArticles.com/972576 Published: Feb. 7, 2008.
Good Vibrations blog; http://vibrotraining.blogspot.com, Earliest posting Jan. 17, 2008.
Breathtaking News; More Youbreathe; Aug. 10, 2007.
U.S. Appl. No. 15/415,524, filed Jan. 25, 2017, Meyer et al.
U.S. Appl. No. 15/453,767, filed Mar. 8, 2017, Meyer et al.

* cited by examiner

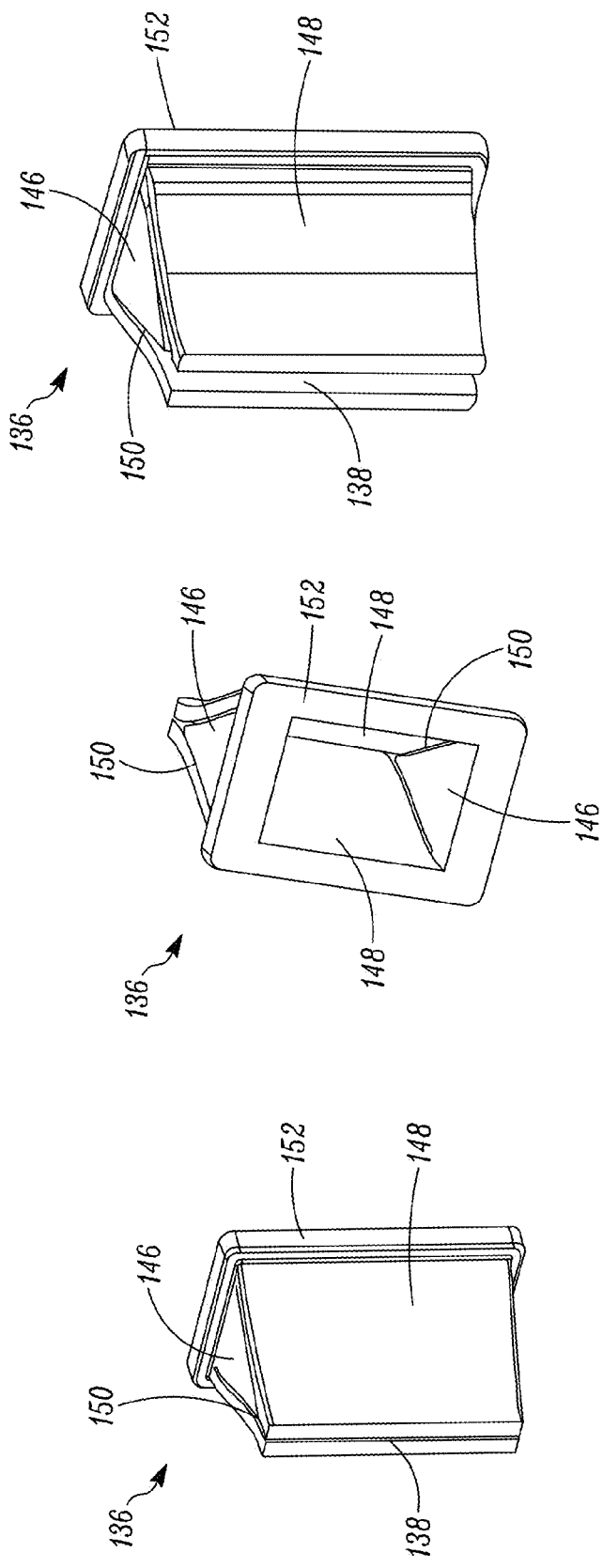

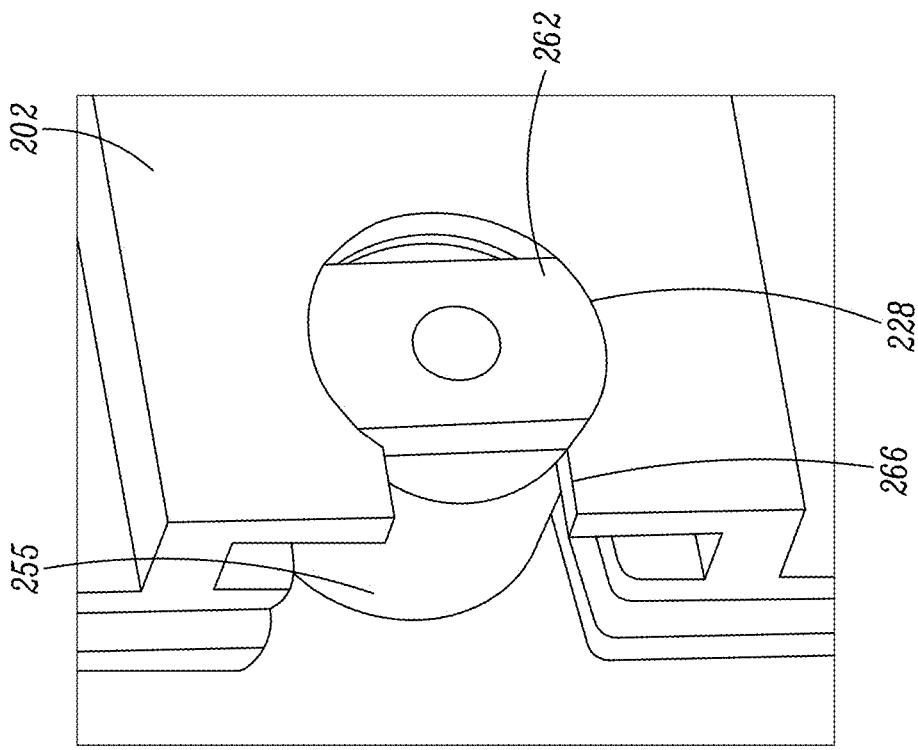
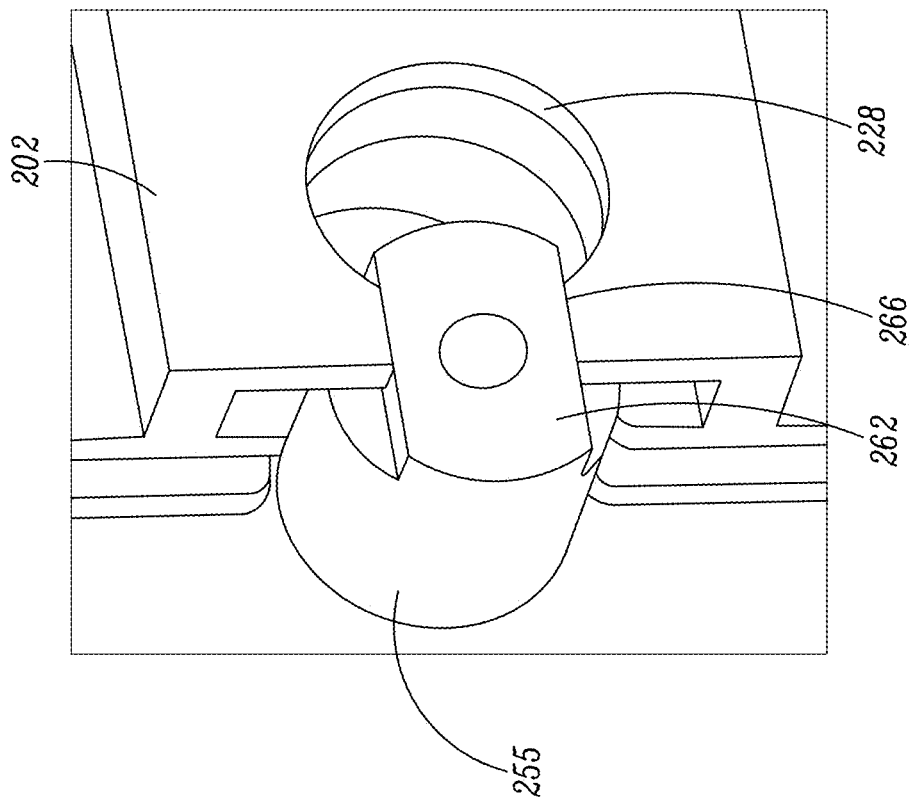

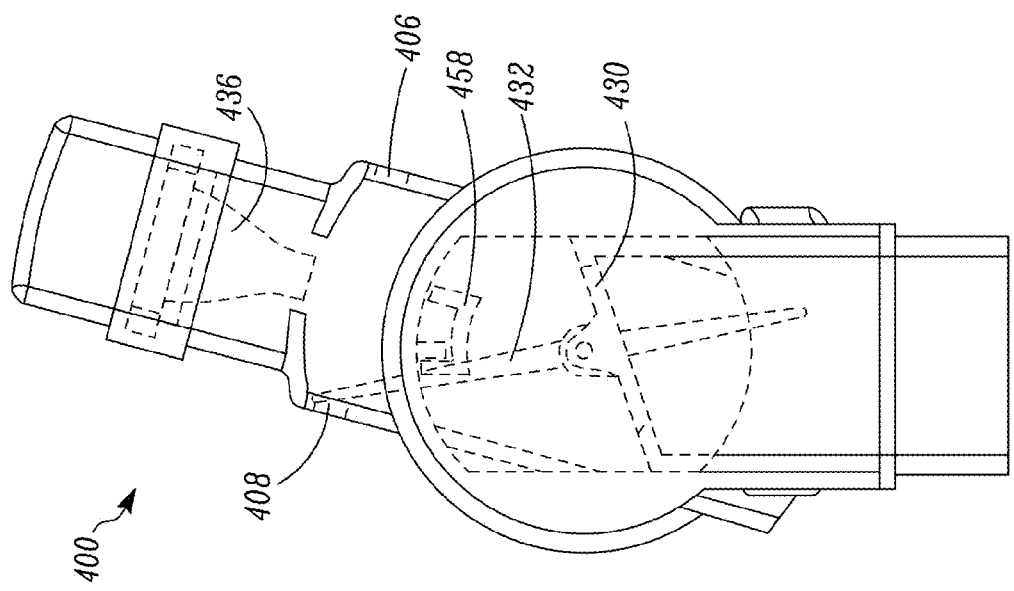
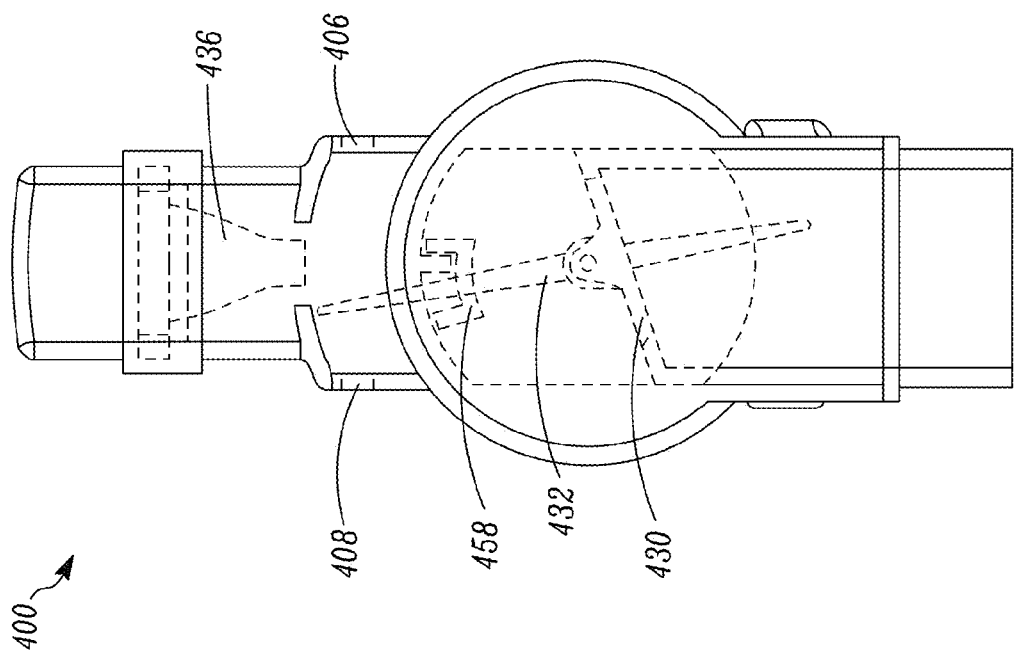

OSCILLATING POSITIVE EXPIRATORY PRESSURE DEVICE

RELATED APPLICATIONS

This application is a continuation of U.S. application Ser. No. 13/489,894, filed on Jun. 6, 2012, pending, which claims the benefit of U.S. Provisional Application No. 61/532,951, filed on Sep. 9, 2011, expired, and U.S. Provisional Application No. 61/493,816, filed on Jun. 6, 2011, expired, all of which are incorporated herein by reference.

TECHNICAL FIELD

The present disclosure relates to a respiratory treatment device, and in particular, to an oscillating positive expiratory pressure ("OPEP") device.

BACKGROUND

Each day, humans may produce upwards of 30 milliliters of sputum, which is a type of bronchial secretion. Normally, an effective cough is sufficient to loosen secretions and clear them from the body's airways. However, for individuals suffering from more significant bronchial obstructions, such as collapsed airways, a single cough may be insufficient to clear the obstructions.

OPEP therapy represents an effective bronchial hygiene technique for the removal of bronchial secretions in the human body and is an important aspect in the treatment and continuing care of patients with bronchial obstructions, such as those suffering from chronic obstructive lung disease. It is believed that OPEP therapy, or the oscillation of exhalation pressure at the mouth during exhalation, effectively transmits an oscillating back pressure to the lungs, thereby splitting open obstructed airways and loosening the secretions contributing to bronchial obstructions.

OPEP therapy is an attractive form of treatment because it can be easily taught to most patients, and such patients can assume responsibility for the administration of OPEP therapy throughout a hospitalization and also from home. To that end, a number of portable OPEP devices have been developed.

BRIEF SUMMARY

In order to provide an effective means for delivering OPEP therapy, a method and device for administering OPEP therapy is disclosed. In a first aspect, a respiratory treatment device includes a housing enclosing at least one chamber, a chamber inlet configured to receive exhaled air into the at least one chamber, at least one chamber outlet configured to permit exhaled air to exit the at least one chamber, and an exhalation flow path defined between the chamber inlet and the at least one chamber outlet. A restrictor member positioned in the exhalation flow path is moveable between a closed position, where a flow of exhaled air along the exhalation flow path is restricted, and an open position, where the flow of exhaled air along the exhalation flow path is less restricted. Furthermore, a vane in fluid communication with the exhalation flow path is operatively connected to the restrictor member and is configured to reciprocate between a first position and a second position in response to a flow of exhaled air along the exhalation flow path. The restrictor member and the vane are axially offset along a common axis of rotation.

In another aspect, in the first position, the vane is positioned to direct the flow of exhaled air to exit the at least one chamber through a first chamber outlet of the at least one chamber outlet, and in the second position, the vane is positioned to direct the flow of exhaled air to exit the at least one chamber through a second chamber outlet of the at least one chamber outlet.

In another aspect, the restrictor member is positioned in a first chamber, while the vane is positioned in a second chamber. The first chamber and the second chamber may be connected by an orifice, and the size of the orifice may be configured to change in response to the flow of exhaled air through the orifice. The restrictor member may be implemented as a butterfly valve. Also, the restrictor member may be operatively connected to the restrictor member by a shaft.

In yet another aspect, a face of the restrictor member is rotatable about an axis of rotation. The face of the restrictor member may also be radially offset from the axis of rotation. In addition, the face of the restrictor member may have a greater surface area positioned on one side of the shaft than the other side of the shaft.

In another aspect, an orientation of the chamber inlet is selectively adjustable.

In a further aspect, the respiratory treatment device includes a chamber inlet bypass configured to permit exhaled air into the at least one chamber without passing through the chamber inlet.

In another aspect, the respiratory treatment device includes a control port configured to permit exhaled air to exit the respiratory treatment device prior to entering the at least one chamber. The respiratory treatment device may also include a control port configured to permit exhaled air to exit the first chamber.

In a further aspect, the respiratory treatment device includes an inhalation port in fluid communication with a user interface. The respiratory treatment device may also include a one-way valve configured to permit air to flow through the inhalation port to the user interface upon inhalation. The inhalation port may be adapted to receive an aerosol medicament from an aerosol delivery device. The aerosol delivery device may be connected to the inhalation port.

In another aspect, the exhalation flow path is folded upon itself.

In another aspect, a respiratory treatment device includes a housing enclosing at least one chamber, a chamber inlet configured to receive exhaled air into the at least one chamber, at least one chamber outlet configured to permit exhaled air to exit the at least one chamber, and an exhalation flow path defined between the chamber inlet and the at least one chamber outlet. A restrictor member positioned in the exhalation flow path is moveable between a closed position, where a flow of exhaled air through the chamber inlet is restricted, and an open position, where the flow of exhaled air through the chamber inlet is less restricted. In addition, an orifice is positioned along the exhalation flow path through which exhaled air passes. A vane positioned adjacent the orifice is operatively connected to the restrictor member and is configured to reciprocate between a first position and a second position in response to an increased pressure adjacent the vane. The restrictor member moves between the closed position and the open position in response to the vane reciprocating between the first position and the second position.

In a further aspect, the restrictor member may be positioned in a first chamber and the vane may be positioned in a second chamber, with the orifice separating the first and the second chamber. In addition, the size of the orifice may be configured to change in response to the flow of exhaled air through the orifice.

In another aspect, a respiratory treatment device includes a housing enclosing at least one chamber, a chamber inlet configured to receive exhaled air into the at least one chamber, at least one chamber outlet configured to permit exhaled air to exit the at least one chamber, and an exhalation flow path defined between the chamber inlet and the at least one chamber outlet. A restrictor member positioned in the exhalation flow path is moveable in response to a flow of exhaled air along the exhalation flow path between a closed position, where the flow of exhaled air along the exhalation flow path is restricted, and an open position, where the flow of exhaled air along the exhalation flow path is less restricted. Furthermore, a variable nozzle is positioned in the exhalation flow path such that the exhalation flow path passes through an orifice of the variable nozzle. A size of the orifice is configured to increase in response to the flow of exhaled air thought the orifice.

In yet another aspect, the respiratory treatment device may comprise a vane positioned adjacent the orifice. The vane may be operatively connected to the restrictor member such that it is configured to move the restrictor member between the closed position and the open position in response to an increased pressure adjacent the vane.

In another aspect, the variable nozzle is positioned downstream from the restrictor member in the exhalation flow path.

In a further aspect, the orifice of the variable nozzle is substantially rectangular. The orifice of the variable nozzle may remain substantially rectangular after an increase in the size of the orifice in repose to the flow of exhaled air through the orifice.

In yet another aspect, a method of performing OPEP therapy includes receiving a flow of exhaled air along an exhalation flow path defined between an inlet and an outlet of a respiratory treatment device, directing the flow of exhaled air toward a vane, and reciprocating the vane between a first position and a second position in response to the flow of exhaled air. The method further includes moving a restrictor member in response to the reciprocal movement of the vane between a closed position, where a flow of exhaled air through the chamber inlet is restricted, and an open position, where the flow of exhaled air is less restricted.

In another aspect, a method of performing OPEP therapy includes receiving a flow of exhaled air along an exhalation flow path defined between an inlet and an outlet of a respiratory treatment device, accelerating the flow of exhaled air though an orifice positioned along the exhalation flow path, and reciprocating a vane adjacent the orifice between a first position and a second position in response to the flow of exhaled air through the orifice. The method further includes moving a restrictor member in response to the reciprocal movement of the vane between a closed position, where a flow of exhaled air along the exhalation flow path is restricted, and an open position, where the flow of exhaled air along the exhalation flow path is less restricted. The method may also include changing a size of the orifice in response to the flow of exhaled air thought the orifice.

In yet another aspect, a respiratory treatment device includes a housing enclosing a plurality of chambers, a first opening in the housing configured to transmit air exhaled into and air inhaled from the housing, a second opening in the housing configured to permit air exhaled into the first opening to exit the housing, and a third opening in the housing configured to permit air outside the housing to enter the housing upon inhalation at the first opening. An exhalation flow path is defined between the first opening and the second opening, and an inhalation flow path defined between the third opening and the first opening. A restrictor member is positioned in the exhalation flow path and the inhalation flow path, and is movable between a closed position, where a flow of air along the exhalation flow path or the inhalation flow path is restricted, and an open position, where the flow of exhaled air along the exhalation flow path or the inhalation flow path is less restricted. A vane is in fluid communication with the exhalation flow path and the inhalation flow path. The vane is operatively connected to the restrictor member and configured to repeatedly reciprocate between a first position and a second position in response to the flow of air along the exhalation flow path or the inhalation flow path.

In a further aspect, the exhalation flow path and the inhalation flow path form an overlapping portion. The flow of air along the exhalation flow path and the inhalation flow path along the overlapping portion may be in the same direction. Furthermore, the restrictor member may be positioned in the overlapping portion, and the vane may be in fluid communication with the overlapping portion.

In another aspect, the restrictor member is positioned in a first chamber of the plurality of chambers, and the vane is positioned in a second chamber of the plurality of chambers. The flow of air through an inlet to the first chamber may be restricted when the restrictor member is in the closed position, and the flow of air through the inlet may be less restricted when the restrictor member is in the open position. In addition, the first chamber and the second chamber may be connected by an orifice. Furthermore, the vane may be positioned adjacent the orifice such that the vane is configured to move the restrictor member between the closed position and the open position in response to an increased pressure adjacent the vane.

In yet another aspect, the second opening includes a one-way exhalation valve configured to permit air exhaled into the housing to exit the housing upon exhalation at the first opening.

In another aspect, the third opening includes a one-way inhalation valve configured to permit air outside the housing to enter the housing upon inhalation at the first opening.

In an additional aspect, a one-way valve is positioned along the exhalation flow path between the first opening and the second opening, such that the one-way valve is configured to open in response to air exhaled into the first opening, and close in response to air inhaled through the first opening.

In a further aspect, a one-way valve is positioned along the inhalation flow path between the third opening and the first opening, such that the one-way valve is configured to open in response to air inhaled through the first opening, and close in response to air exhaled into the first opening.

In yet another aspect, the respiratory treatment device may include an inhalation port in fluid communication with a user interface, wherein the inhalation port is adapted to receive an medicament suitable for inhalation from an aerosol delivery device. The aerosol delivery device may be connected to the inhalation port.

BRIEF DESCRIPTION OF THE DRAWINGS

FIG. 12 is a front perspective view of a variable nozzle shown without the flow of exhaled air therethrough;

FIG. 13 is a rear perspective view of the variable nozzle of FIG. 12 shown without the flow of exhaled air therethrough;

FIG. 14 is a front perspective view of the variable nozzle of FIG. 12 shown with a high flow of exhaled air therethrough;

FIGS. 29A-B are partial cross-sectional views illustrating installation of the assembly of FIG. 27 within the OPEP device of FIG. 18;

FIGS. 41A-B are top phantom views of the OPEP device of FIG. 39, illustrating the adjustability of the OPEP device;

DETAILED DESCRIPTION

Figure 1:
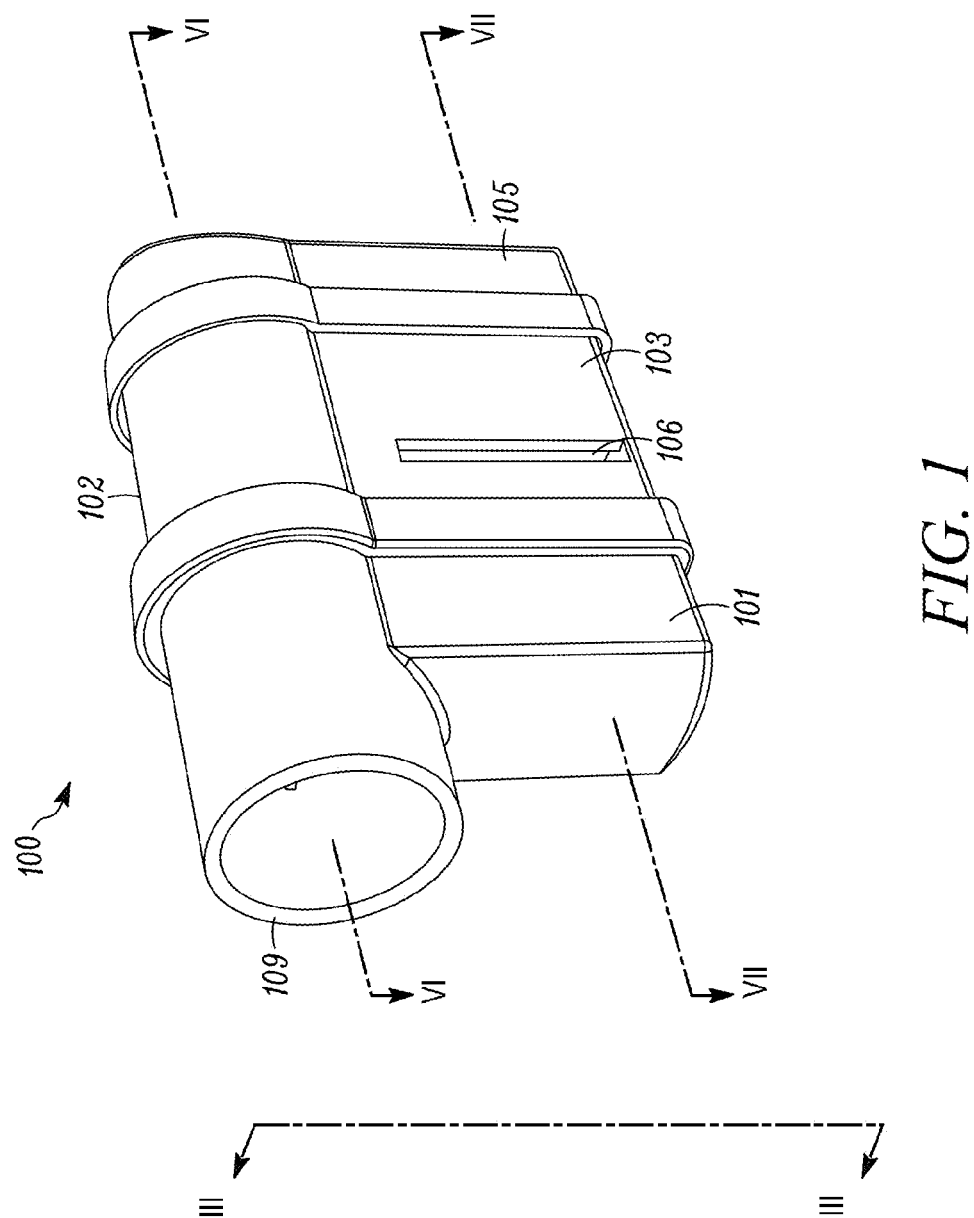
FIG. 1 is a front perspective view of an OPEP device.
Figure 2:
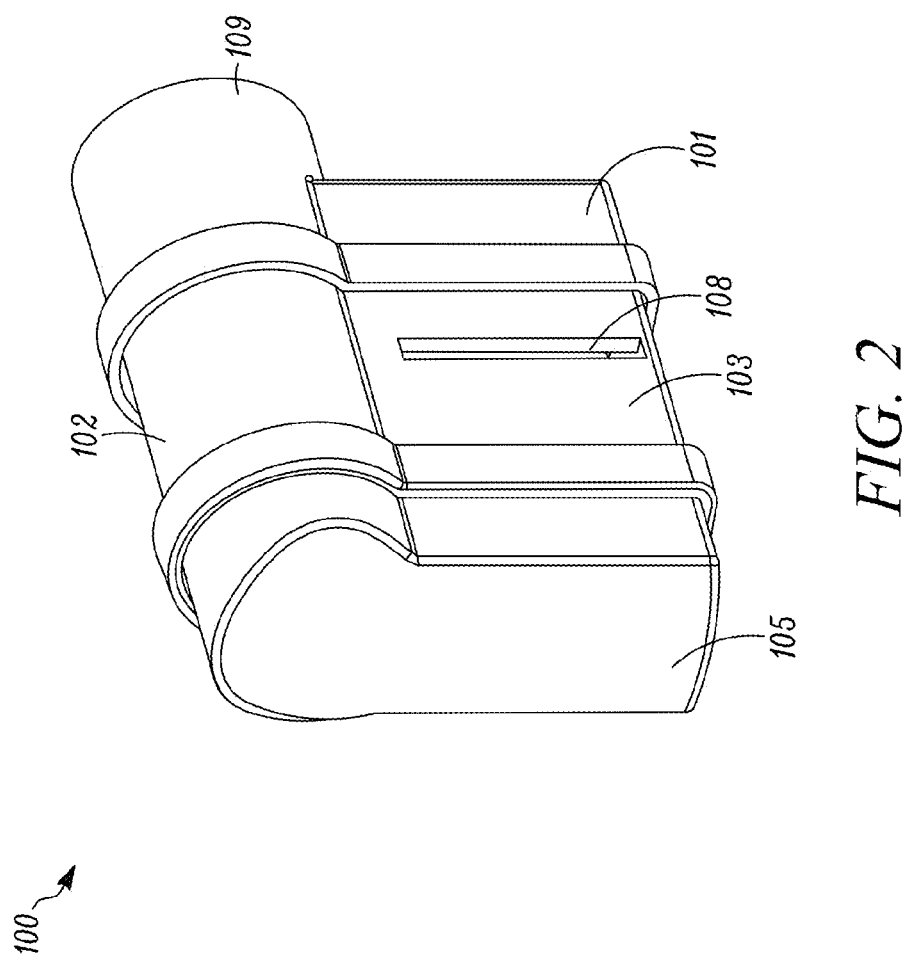
FIG. 2 is a rear perspective view of the OPEP device of FIG. 1.

OPEP therapy is effective within a range of operating conditions. For example, an adult human may have an exhalation flow rate ranging from 10 to 60 liters per minute, and may maintain a static exhalation pressure in the range of 8 to 18 cm $H_2O$. Within these parameters, OPEP therapy is believed to be most effective when changes in the exhalation pressure (i.e., the amplitude) range from 5 to 20 cm $H_2O$ oscillating at a frequency of 10 to 40 Hz. In contrast, an adolescent may have a much lower exhalation flow rate, and may maintain a lower static exhalation pressure, thereby altering the operating conditions most effective for the administration of OPEP therapy. Likewise, the ideal operating conditions for someone suffering from a respiratory illness, or in contrast, a healthy athlete, may differ from those of an average adult. As described below, the components of the disclosed OPEP devices are selectable and/or adjustable so that ideal operating conditions (e.g., amplitude and frequency of oscillating pressure) may be identified and maintained. Each of the various embodiments described herein achieve frequency and amplitude ranges that fall within the desired ranges set forth above. Each of the various embodiments described herein may also be configured to achieve frequencies and amplitudes that fall outside the ranges set forth above.

First Embodiment

Referring first to FIGS. 1-4, a front perspective view, a rear perspective view, a cross-sectional front perspective view, and an exploded view of an OPEP device 100 are shown. For purposes of illustration, the internal components of the OPEP device 100 are omitted in FIG. 3. The OPEP device 100 generally comprises a housing 102, a chamber inlet 104, a first chamber outlet 106, a second chamber outlet 108 (best seen in FIGS. 2 and 7), and a mouthpiece 109 in fluid communication with the chamber inlet 104. While the mouthpiece 109 is shown in FIGS. 1-4 as being integrally formed with the housing 102, it is envisioned that the mouthpiece 109 may be removable and replaceable with a mouthpiece 109 of a different size or shape, as required to maintain ideal operating conditions. In general, the housing 102 and the mouthpiece 109 may be constructed of any durable material, such as a polymer. One such material is Polypropylene. Alternatively, acrylonitrile butadiene styrene (ABS) may be used.

Alternatively, other or additional interfaces, such as breathing tubes or gas masks (not shown) may be attached in fluid communication with the mouthpiece 109 and/or associated with the housing 102. For example, the housing 102 may include an inhalation port (not shown) having a separate one-way inhalation valve (not shown) in fluid communication with the mouthpiece 109 to permit a user of the OPEP device 100 both to inhale the surrounding air through the one-way valve, and to exhale through the chamber inlet 104 without withdrawing the mouthpiece 109 of the OPEP device 100 between periods of inhalation and exhalation. In addition, any number of aerosol delivery devices may be connected to the OPEP device 100, for example, through the inhalation port mentioned above, for the simultaneous administration of aerosol and OPEP therapies. As such, the inhalation port may include, for example, an elastomeric adapter, or other flexible adapter, capable of accommodating the different mouthpieces or outlets of the particular aerosol delivery device that a user intends to use with the OPEP device 100. As used herein, the term aerosol delivery devices should be understood to include, for example, without limitation, any nebulizer, soft mist inhaler, pressurized metered dose inhaler, dry powder inhaler, combination of a holding chamber a pressurized metered dose inhaler, or the like. Suitable commercially available aerosol delivery devices include, without limitation, the AEROECLIPSE nebulizer, RESPIMAT soft mist inhaler, LC Sprint nebulizer, AEROCHAMBER PLUS holding chambers, MICRO MIST nebulizer, SIDESTREAM nebulizers, Inspiration Elite nebulizers, FLOVENT pMDI, VENTOLIN pMDI, AZMACORT pMDI, BECLOVENT pMDI, QVAR pMDI and AEROBID PMDI, XOPENEX pMDI, PROAIR pMDI, PROVENT pMDI, SYMBICORT pMDI, TURBOHALER DPI, and DISKHALER DPI. Descriptions of suitable aerosol delivery devices may be found in U.S. Pat. Nos. 4,566,452; 5,012,803; 5,012,804; 5,312,046; 5,497,944; 5,622,162; 5,823,179; 6,293,279; 6,435,177; 6,484,717; 6,848,443; 7,360,537; 7,568,480; and, 7,905,228, the entireties of which are herein incorporated by reference.

In FIGS. 1-4, the housing 102 is generally box-shaped. However, a housing 102 of any shape may be used. Furthermore, the chamber inlet 104, the first chamber outlet 106, and the second chamber outlet 108 could be any shape or series of shapes, such as a plurality (i.e., more than one) of circular passages or linear slots. More importantly, it should be appreciated that the cross-sectional area of the chamber inlet 104, the first chamber outlet 106, and the second chamber outlet 108 are only a few of the factors influencing the ideal operating conditions described above.

Preferably, the housing 102 is openable so that the components contained therein can be periodically accessed, cleaned, replaced, or reconfigured, as required to maintain the ideal operating conditions. As such, the housing 102 is shown in FIGS. 1-4 as comprising a front section 101, a middle section 103, and a rear section 105. The front section 101, the middle section 103, and the rear section 105 may be removably connected to one another by any suitable means, such as a snap-fit, a compression fit, etc., such that a seal forms between the relative sections sufficient to permit the OPEP device 100 to properly administer OPEP therapy.

Figure 3:
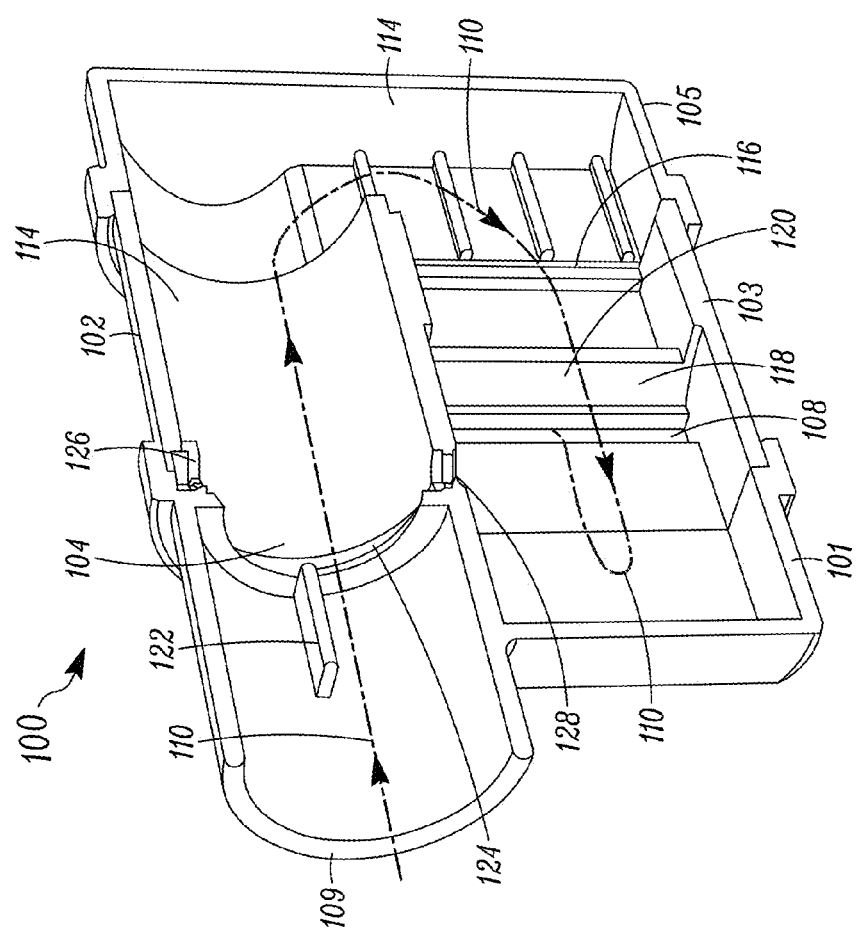
FIG. 3 is a cross-sectional perspective view taken along line III in FIG. 1 of the OPEP device shown without the internal components of the OPEP device.
Figure 7:
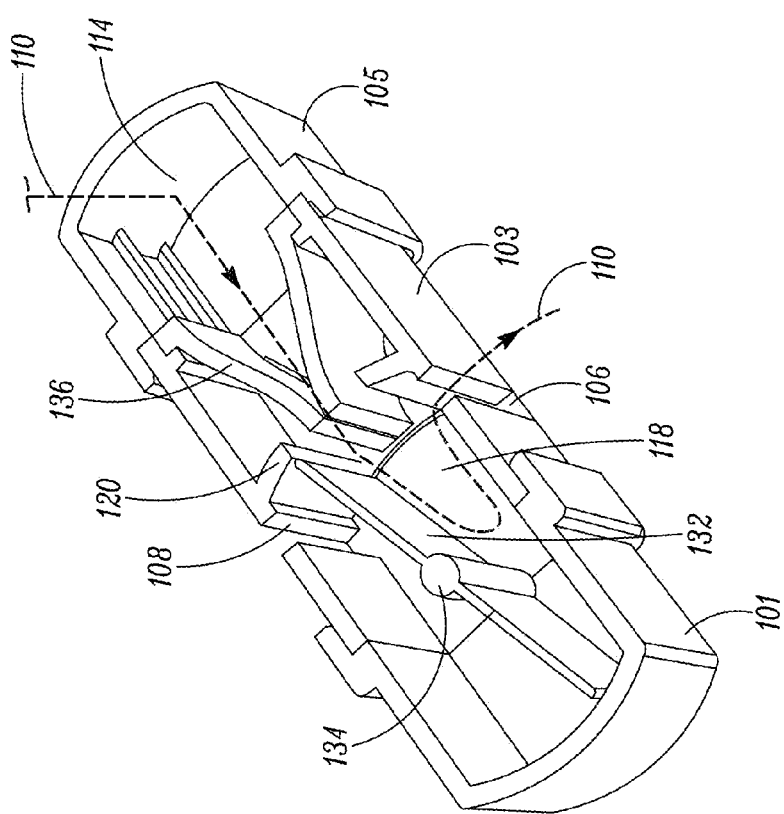
FIG. 7 is a different cross-sectional perspective view taken along line VII in FIG. 1 of the OPEP device shown with the internal components of the OPEP device.

As shown in FIG. 3, an exhalation flow path 110, identified by a dashed line, is defined between the mouthpiece 109 and at least one of the first chamber outlet 106 and the second chamber outlet 108 (best seen in FIG. 7). More specifically, the exhalation flow path 110 begins at the mouthpiece 109, passes through the chamber inlet 104, and enters into a first chamber 114, or an entry chamber. In the first chamber 114, the exhalation flow path makes a 180-degree turn, passes through a chamber passage 116, and enters into a second chamber 118, or an exit chamber. In the second chamber 118, the exhalation flow path 110 may exit the OPEP device 100 through at least one of the first chamber outlet 106 and the second chamber outlet 108. In this way, the exhalation flow path 110 is "folded" upon itself, i.e., it reverses longitudinal directions between the chamber inlet 104 and one of the first chamber outlet 106 or the second chamber outlet 108. However, those skilled in the art will appreciate that the exhalation flow path 110 identified by the dashed line is exemplary, and that air exhaled into the OPEP device 100 may flow in any number of directions or paths as it traverses from the mouthpiece 109 or chamber inlet 104 and the first chamber outlet 106 or the second chamber outlet 108.

FIG. 3 also shows various other features of the OPEP device 100 associated with the housing 102. For example, a stop 122 prevents a restrictor member 130 (see FIG. 5), described below, from opening in a wrong direction; a seat 124 shaped to accommodate the restrictor member 130 is formed about the chamber inlet 104; and, an upper bearing 126 and a lower bearing 128 are formed within the housing 102 and configured to accommodate a shaft rotatably mounted therebetween. One or more guide walls 120 are positioned in the second chamber 118 to direct exhaled air along the exhalation flow path 110.

Figure 5:
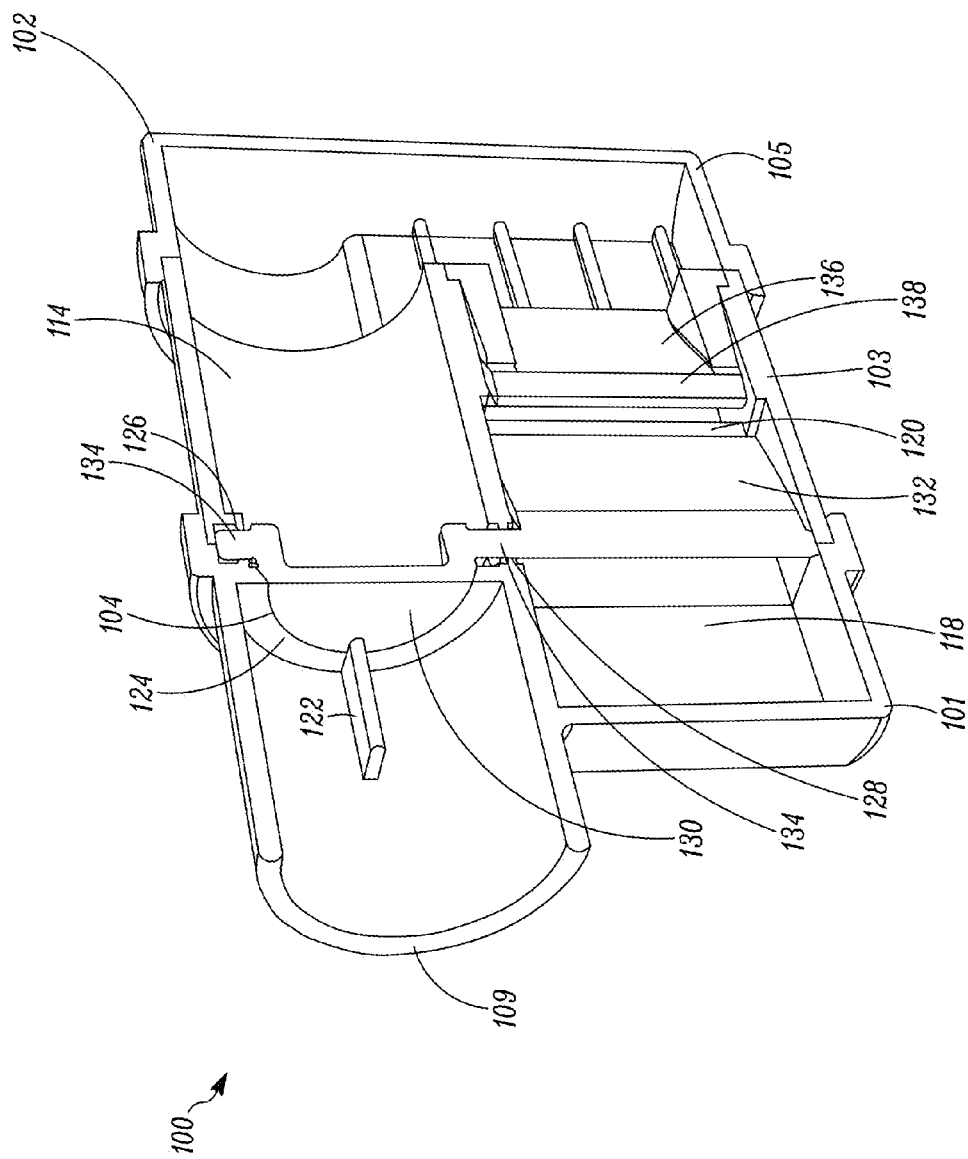
FIG. 5 is a cross-sectional perspective view taken along line III in FIG. 1 of the OPEP device shown with the internal components of the OPEP device.
Figure 6:
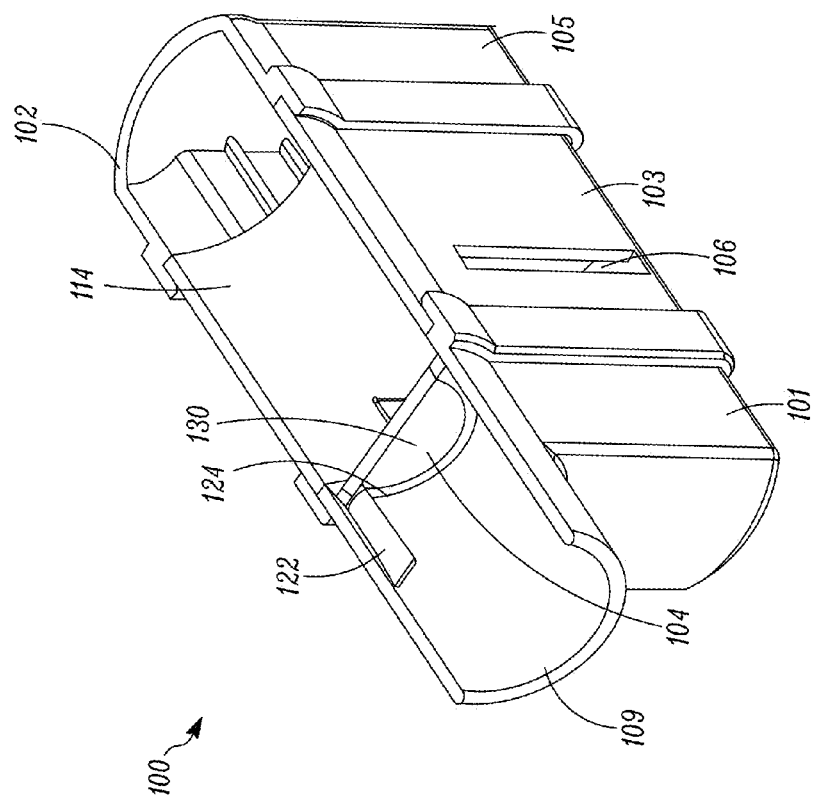
FIG. 6 is a different cross-sectional perspective view taken along line VI in FIG. 1 of the OPEP device shown with the internal components of the OPEP device.

Turning to FIGS. 5-7, various cross-sectional perspective views of the OPEP device 100 are shown with its internal components. The internal components of the OPEP device 100 comprise a restrictor member 130, a vane 132, and an optional variable nozzle 136. As shown, the restrictor member 130 and the vane 132 are operatively connected by means of a shaft 134 rotatably mounted between the upper bearing 126 and the lower bearing 128, such that the restrictor member 130 and the vane 132 are rotatable in unison about the shaft 134. As described below in further detail, the variable nozzle 136 includes an orifice 138 configured to increase in size in response to the flow of exhaled air therethrough.

Figure 4:
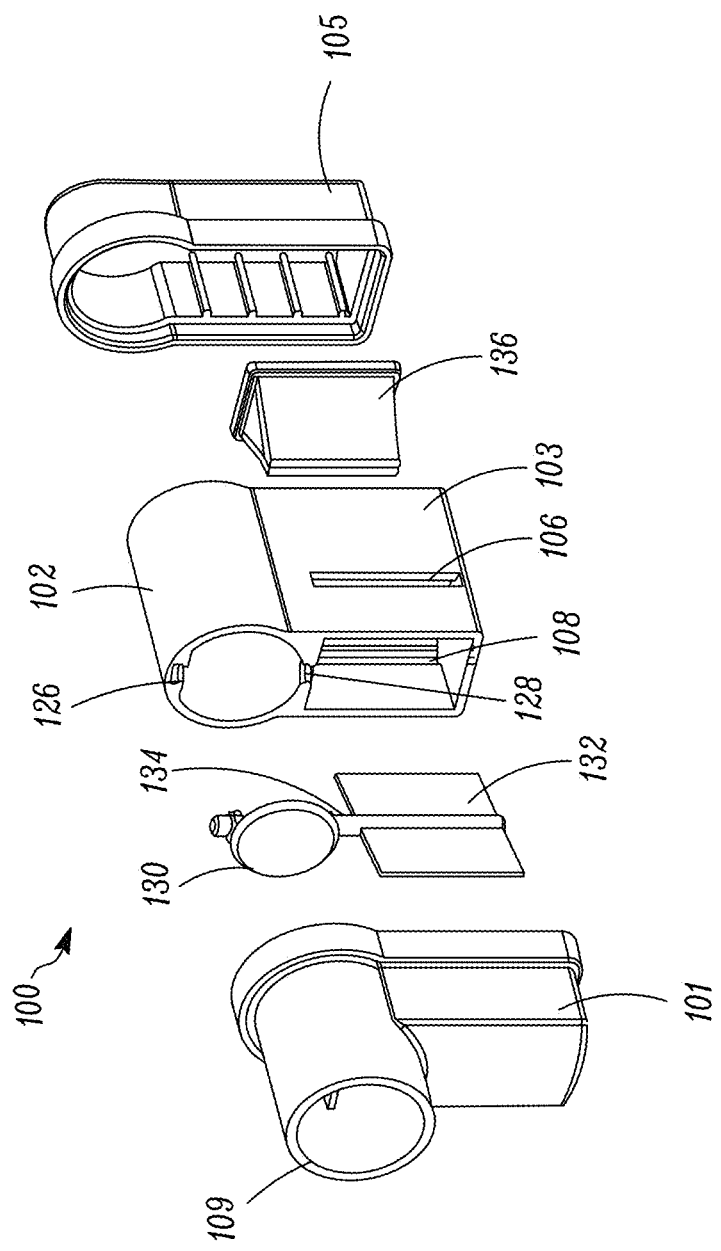
FIG. 4 is an exploded view of the OPEP device of FIG. 1, shown with the internal components of the OPEP device.

FIGS. 4-6 further illustrate the division of the first chamber 114 and the second chamber 118 within the housing 102. As previously described, the chamber inlet 104 defines an entrance to the first chamber 114. The restrictor member 130 is positioned in the first chamber 114 relative to a seat 124 about the chamber inlet 104 such that it is moveable between a closed position, where a flow of exhaled air along the exhalation flow path 110 through the chamber inlet 104 is restricted, and an open position, where the flow of exhaled air through the chamber inlet 104 is less restricted. Likewise, the variable nozzle 136, which is optional, is mounted about or positioned in the chamber passage 116, such that the flow of exhaled air entering the first chamber 114 exits the first chamber 114 through the orifice 138 of the variable nozzle 136. Exhaled air exiting the first chamber 114 through the orifice 138 of the variable nozzle 136 enters the second chamber, which is defined by the space within the housing 102 occupied by the vane 132 and the guide walls 120. Depending on the position of the vane 132, the exhaled air is then able to exit the second chamber 118 through at least one of the first chamber outlet 106 and the second chamber outlet 108.

Figure 9:
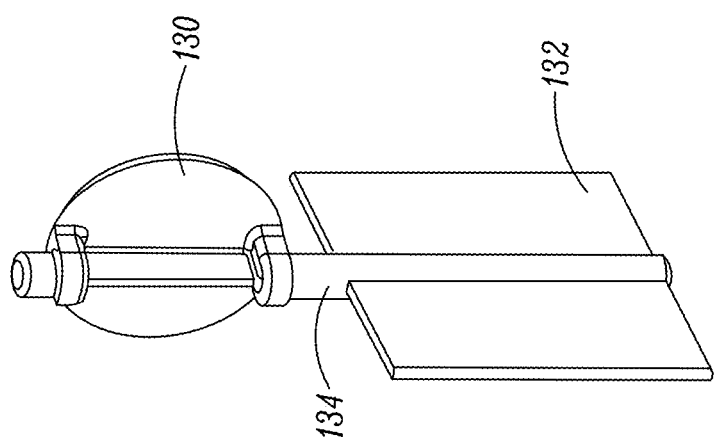
FIG. 9 is a rear perspective view of the restrictor member operatively connected to the vane shown in FIG. 8.
Figure 8:
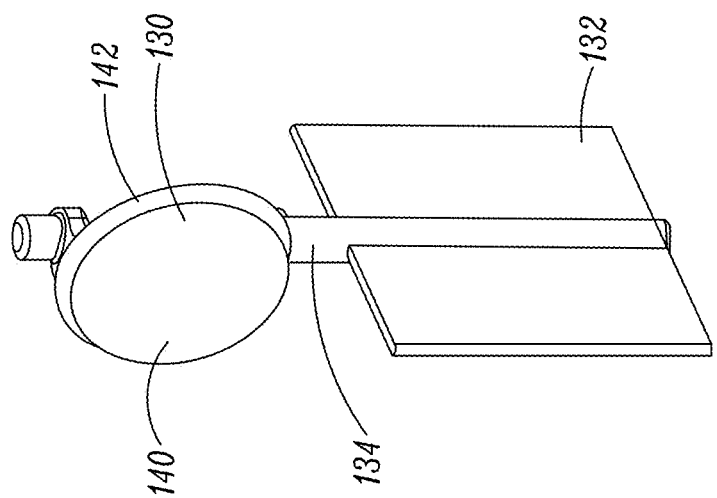
FIG. 8 is a front perspective view of a restrictor member operatively connected to a vane.

FIGS. 8-14 show the internal components of the OPEP device 100 in greater detail. Turning first to FIGS. 8-9, a front perspective view and a rear perspective view shows the restrictor member 130 operatively connected to the vane 132 by the shaft 134. As such, the restrictor member 130 and the vane 132 are rotatable about the shaft 134 such that rotation of the restrictor member 130 results in a corresponding rotation of the vane 132, and vice-versa. Like the housing 102, the restrictor member 130 and the vane 132 may be made of constructed of any durable material, such as a polymer. Preferably, they are constructed of a low shrink, low friction plastic. One such material is acetal.

As shown, the restrictor member 130, the vane 132, and the shaft 134 are formed as a unitary component. The restrictor member 130 is generally disk-shaped, and the vane 132 is planar. The restrictor member 130 includes a generally circular face 140 axially offset from the shaft 134 and a beveled or chamfered edge 142 shaped to engage the seat 124 formed about the chamber inlet 104. In this way, the restrictor member 130 is adapted to move relative to the chamber inlet 104 about an axis of rotation defined by the shaft 134 such that the restrictor member 130 may engage the seat 124 in a closed position to substantially seal and restrict the flow of exhaled air through the chamber inlet 104. However, it is envisioned that the restrictor member 130 and the vane 132 may be formed as separate components connectable by any suitable means such that they remain independently replaceable with a restrictor member 130 or a vane 132 of a different shape, size, or weight, as selected to maintain ideal operating conditions. For example, the restrictor member 130 and/or the vane 132 may include one or more contoured surfaces. Alternatively, the restrictor member 130 may be configured as a butterfly valve.

Figure 10:
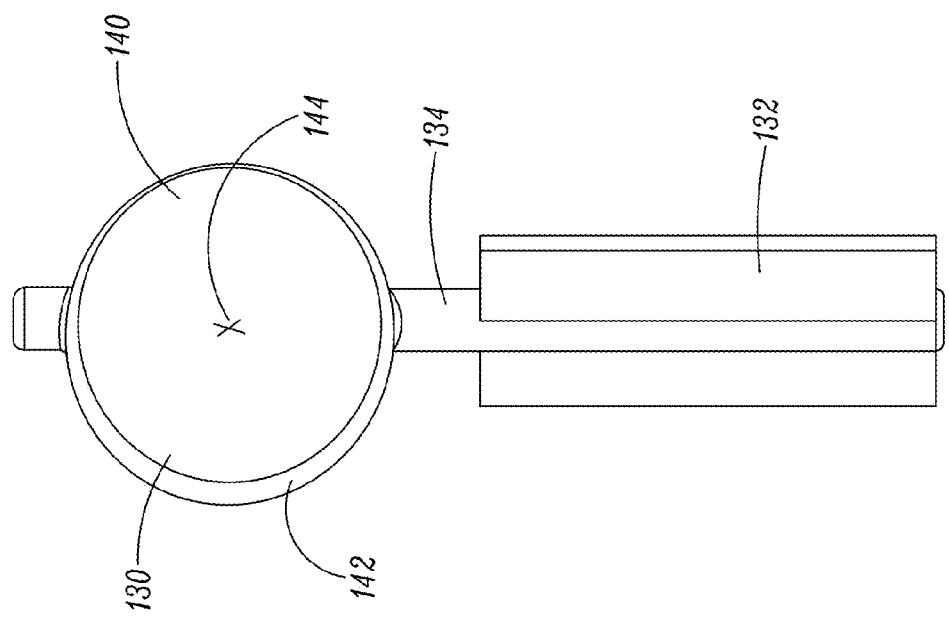
FIG. 10 is a front view of the restrictor member operatively connected to the vane shown in FIG. 8.

Turning to FIG. 10, a front view of the restrictor member 130 and the vane 132 is shown. As previously described, the restrictor member 130 comprises a generally circular face 140 axially offset from the shaft 134. The restrictor member 130 further comprises a second offset designed to facilitate movement of the restrictor member 130 between a closed position and an open position. More specifically, a center 144 of the face 140 of the restrictor member 130 is offset from the plane defined by the radial offset and the shaft 134, or the axis of rotation. In other words, a greater surface area of the face 140 of the restrictor member 130 is positioned on one side of the shaft 134 than on the other side of the shaft 134. Pressure at the chamber inlet 104 derived from exhaled air produces a force acting on the face 140 of the restrictor member 130. Because the center 144 of the face 140 of the restrictor member 130 is offset as described above, a resulting force differential creates a torque about the shaft 134. As further explained below, this torque facilitates movement of the restrictor member 130 between a closed position and an open position.

Figure 11:
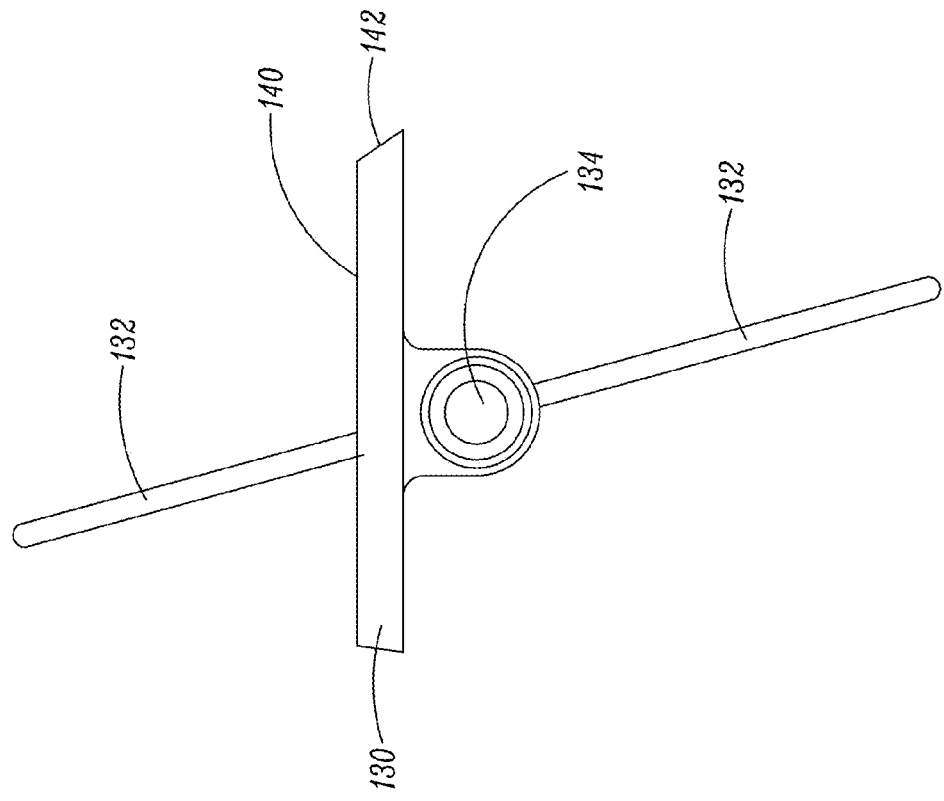
FIG. 11 is a top view of the restrictor member operatively connected to the vane shown in FIG. 8.

Turning to FIG. 11, a top view of the restrictor member 130 and the vane 132 is shown. As illustrated, the vane 132 is connected to the shaft 134 at a 75° angle relative to the face 140 of restrictor member 130. Preferably, the angle will remain between 60° and 80°, although it is envisioned that the angle of the vane 132 may be selectively adjusted to maintain the ideal operating conditions, as previously discussed. It is also preferable that the vane 132 and the restrictor member 130 are configured such that when the OPEP device 100 is fully assembled, the angle between a centerline of the variable nozzle 136 and the vane 132 is between 10° and 25° when the restrictor member 130 is in a closed position. Moreover, regardless of the configuration, it is preferable that the combination of the restrictor member 130 and the vane 132 have a center of gravity aligned with the shaft 134, or the axis of rotation. In full view of the present disclosure, it should be apparent to those skilled in the art that the angle of the vane 132 may be limited by the size or shape of the housing 102, and will generally be less than half the total rotation of the vane 132 and the restrictor member 130.

Turning to FIGS. 12 and 13, a front perspective view and a rear perspective view of the variable nozzle 136 is shown without the flow of exhaled air therethrough. In general, the variable nozzle 136 includes top and bottom walls 146, side walls 148, and V-shaped slits 150 formed therebetween. As shown, the variable nozzle is generally shaped like a duckbill type valve. However, it should be appreciated that nozzles or valves of other shapes and sizes may also be used. The variable nozzle 136 may also include a lip 152 configured to mount the variable nozzle 136 within the housing 102 between the first chamber 114 and the second chamber 118. The variable nozzle 136 may be constructed or molded of any material having a suitable flexibility, such as silicone, and preferably with a wall thickness of between 0.50 and 2.00 millimeters, and an orifice width between 0.25 to 1.00 millimeters, or smaller depending on manufacturing capabilities.

As previously described, the variable nozzle 136 is optional in the operation of the OPEP device 100. It should also be appreciated that the OPEP device 100 could alternatively omit both the chamber passage 116 and the variable nozzle 136, and thus comprise a single-chamber embodiment. Although functional without the variable nozzle 136, the performance of the OPEP device 100 over a wider range of exhalation flow rates is improved when the OPEP device 100 is operated with the variable nozzle 136. The chamber passage 116, when used without the variable nozzle 136, or the orifice 138 of the variable nozzle 136, when the variable nozzle 136 is included, serves to create a jet of exhaled air having an increased velocity. As explained in more detail below, the increased velocity of the exhaled air entering the second chamber 118 results in a proportional increase in the force applied by the exhaled air to the vane 132, and in turn, an increased torque about the shaft 134, all of which affect the ideal operating conditions.

Without the variable nozzle 136, the orifice between the first chamber 114 and the second chamber 118 is fixed according to the size, shape, and cross-sectional area of the chamber passage 116, which may be selectively adjusted by any suitable means, such as replacement of the middle section 103 or the rear section 105 of the housing. On the other hand, when the variable nozzle 136 is included in the OPEP device 100, the orifice between the first chamber 114 and the second chamber 118 is defined by the size, shape, and cross-sectional area of the orifice 138 of the variable nozzle 136, which may vary according to the flow rate of exhaled air and/or the pressure in the first chamber 114.

Turning to FIG. 14, a front perspective view of the variable nozzle 136 is shown with a flow of exhaled air therethrough. One aspect of the variable nozzle 136 shown in FIG. 14 is that, as the orifice 138 opens in response to the flow of exhaled air therethrough, the cross-sectional shape of the orifice 138 remains generally rectangular, which during the administration of OPEP therapy results in a lower drop in pressure through the variable nozzle 136 from the first chamber 114 (See FIGS. 3 and 5) to the second chamber 118. The generally consistent rectangular shape of the orifice 138 of the variable nozzle 136 during increased flow rates is achieved by the V-shaped slits 150 formed between the top and bottom walls 146 and the side walls 148, which serve to permit the side walls 148 to flex without restriction. Preferably, the V-shaped slits 150 are as thin as possible to minimize the leakage of exhaled air therethrough. For example, the V-shaped slits 150 may be approximately 0.25 millimeters wide, but depending on manufacturing capabilities, could range between 0.10 and 0.50 millimeters. Exhaled air that does leak through the V-shaped slits 150 is ultimately directed along the exhalation flow path by the guide walls 120 in the second chamber 118 protruding from the housing 102.

It should be appreciated that numerous factors contribute to the impact the variable nozzle 136 has on the performance of the OPEP device 100, including the geometry and material of the variable nozzle 136. By way of example only, in order to attain a target oscillating pressure frequency of between 10 to 13 Hz at an exhalation flow rate of 15 liters per minute, in one embodiment, a 1.0 by 20.0 millimeter passage or orifice may be utilized. However, as the exhalation flow rate increases, the frequency of the oscillating pressure in that embodiment also increases, though at a rate too quickly in comparison to the target frequency. In order to attain a target oscillating pressure frequency of between 18 to 20 Hz at an exhalation flow rate of 45 liters per minute, the same embodiment may utilize a 3.0 by 20.0 millimeter passage or orifice. Such a relationship demonstrates the desirability of a passage or orifice that expands in cross-sectional area as the exhalation flow rate increases in order to limit the drop in pressure across the variable nozzle 136.

Figure 15A:
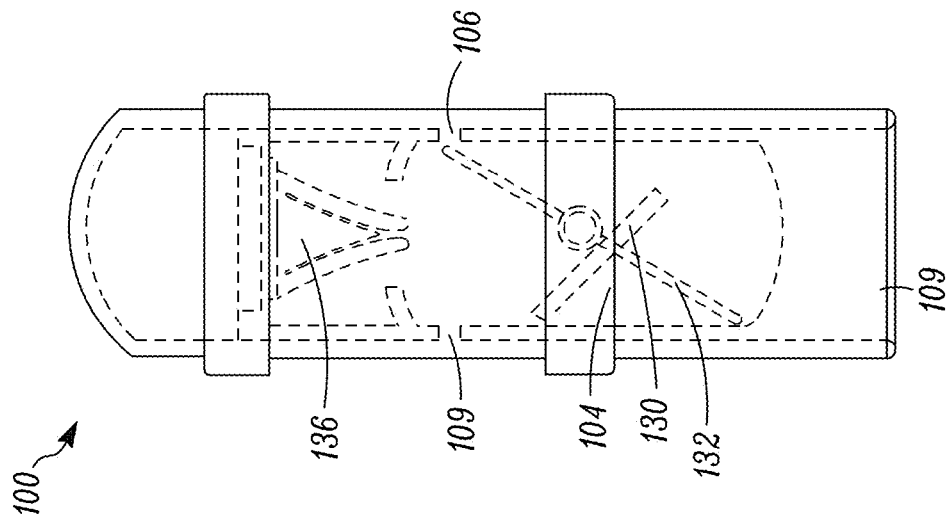
FIGS. 15A-C are top phantom views of the OPEP device of FIG. 1 showing an exemplary illustration of the operation of the OPEP device of FIG. 1.
Figure 15B:
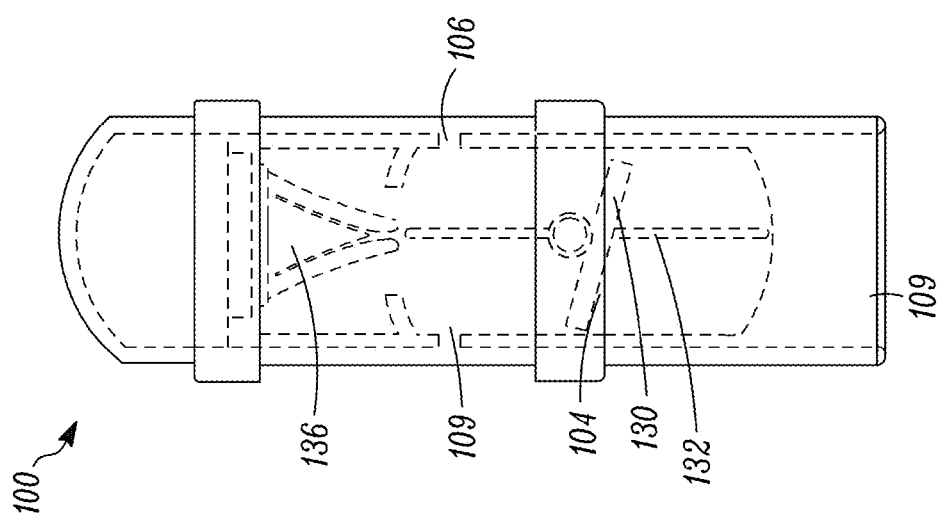
Figure 15C:
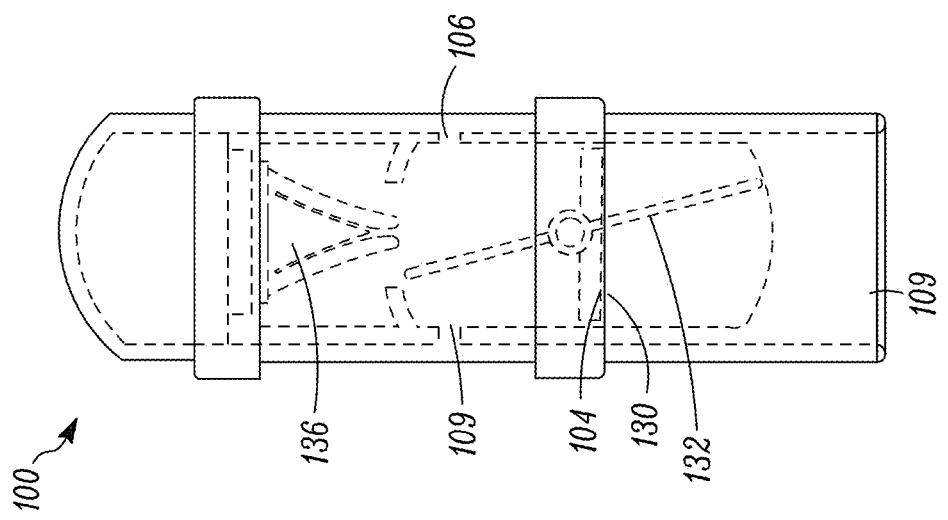

Turning to FIGS. 15A-C, top phantom views of the OPEP device 100 show an exemplary illustration of the operation of the OPEP device 100. Specifically, FIG. 15A shows the restrictor member 130 in an initial, or closed position, where the flow of exhaled air through the chamber inlet 104 is restricted, and the vane 132 is in a first position, directing the flow of exhaled air toward the first chamber outlet 106. FIG. 15B shows this restrictor member 130 in a partially open position, where the flow of exhaled air through the chamber inlet 104 is less restricted, and the vane 132 is directly aligned with the jet of exhaled air exiting the variable nozzle 136. FIG. 15C shows the restrictor member 130 in an open position, where the flow of exhaled air through the chamber inlet 104 is even less restricted, and the vane 132 is in a second position, directing the flow of exhaled air toward the second chamber outlet 108. It should be appreciated that the cycle described below is merely exemplary of the operation of the OPEP device 100, and that numerous factors may affect operation of the OPEP device 100 in a manner that results in a deviation from the described cycle. However, during the operation of the OPEP device 100, the restrictor member 130 and the vane 132 will generally reciprocate between the positions shown in FIGS. 15A and 15C.

During the administration of OPEP therapy, the restrictor member 130 and the vane 132 may be initially positioned as shown in FIG. 15A. In this position, the restrictor member 130 is in a closed position, where the flow of exhaled air along the exhalation path through the chamber inlet 104 is substantially restricted. As such, an exhalation pressure at the chamber inlet 104 begins to increase when a user exhales into the mouthpiece 108. As the exhalation pressure at the chamber inlet 104 increases, a corresponding force acting on the face 140 of the restrictor member 130 increases. As previously explained, because the center 144 of the face 140 is offset from the plane defined by the radial offset and the shaft 134, a resulting net force creates a negative or opening torque about the shaft. In turn, the opening torque biases the restrictor member 130 to rotate open, letting exhaled air enter the first chamber 114, and biases the vane 132 away from its first position. As the restrictor member 130 opens and exhaled air is let into the first chamber 114, the pressure at the chamber inlet 104 begins to decrease, the force acting on the face 140 of the restrictor member begins to decrease, and the torque biasing the restrictor member 130 open begins to decrease.

As exhaled air continues to enter the first chamber 114 through the chamber inlet 104, it is directed along the exhalation flow path 110 by the housing 102 until it reaches the chamber passage 116 disposed between the first chamber 114 and the second chamber 118. If the OPEP device 100 is being operated without the variable nozzle 136, the exhaled air accelerates through the chamber passage 116 due to the decrease in cross-sectional area to form a jet of exhaled air. Likewise, if the OPEP device 100 is being operated with the variable nozzle 136, the exhaled air accelerates through the orifice 138 of the variable nozzle 136, where the pressure through the orifice 138 causes the side walls 148 of the variable nozzle 136 to flex outward, thereby increasing the size of the orifice 138, as well as the resulting flow of exhaled air therethrough. To the extent some exhaled air leaks out of the V-shaped slits 150 of the variable nozzle 136, it is directed back toward the jet of exhaled air and along the exhalation flow path by the guide walls 120 protruding into the housing 102.

Then, as the exhaled air exits the first chamber 114 through the variable nozzle 136 and/or chamber passage 116 and enters the second chamber 118, it is directed by the vane 132 toward the front section 101 of the housing 102, where it is forced to reverse directions before exiting the OPEP device 100 through the open first chamber exit 106. As a result of the change in direction of the exhaled air toward the front section 101 of the housing 102, a pressure accumulates in the second chamber 118 near the front section 101 of the housing 102, thereby resulting in a force on the adjacent vane 132, and creating an additional negative or opening torque about the shaft 134. The combined opening torques created about the shaft 134 from the forces acting on the face 140 of the restrictor member 130 and the vane 132 cause the restrictor member 130 and the vane 132 to rotate about the shaft 134 from the position shown in FIG. 15A toward the position shown in FIG. 15B.

When the restrictor member 130 and the vane 132 rotate to the position shown in FIG. 15B, the vane 132 crosses the jet of exhaled air exiting the variable nozzle 136 or the chamber passage 116. Initially, the jet of exhaled air exiting the variable nozzle 136 or chamber passage 116 provides a force on the vane 132 that, along with the momentum of the vane 132, the shaft 134, and the restrictor member 130, propels the vane 132 and the restrictor member 130 to the position shown in FIG. 15C. However, around the position shown in FIG. 15B, the force acting on the vane 132 from the exhaled air exiting the variable nozzle 136 also switches from a negative or opening torque to a positive or closing torque. More specifically, as the exhaled air exits the first chamber 114 through the variable nozzle 136 and enters the second chamber 118, it is directed by the vane 132 toward the front section 101 of the housing 102, where it is forced to reverse directions before exiting the OPEP device 100 through the open second chamber exit 108. As a result of the change in direction of the exhaled air toward the front section 101 of the housing 102, a pressure accumulates in the second chamber 118 near the front section 101 of the housing 102, thereby resulting in a force on the adjacent vane 132, and creating a positive or closing torque about the shaft 134. As the vane 132 and the restrictor member 130 continue to move closer to the position shown in FIG. 15C, the pressure accumulating in the section chamber 118 near the front section 101 of the housing 102, and in turn, the positive or closing torque about the shaft 134, continues to increase, as the flow of exhaled air along the exhalation flow path 110 and through the chamber inlet 104 is even less restricted. Meanwhile, although the torque about the shaft 134 from the force acting on the restrictor member 130 also switches from a negative or opening torque to a positive or closing torque around the position shown in FIG. 15B, its magnitude is essentially negligible as the restrictor member 130 and the vane 132 rotate from the position shown in FIG. 15B to the position shown in FIG. 15C.

After reaching the position shown in FIG. 15C, and due to the increased positive or closing torque about the shaft 134, the vane 132 and the restrictor member 130 reverse directions and begin to rotate back toward the position shown in FIG. 15B. As the vane 132 and the restrictor member 130 approach the position shown in FIG. 15B, and the flow of exhaled through the chamber inlet 104 is increasingly restricted, the positive or closing torque about the shaft 134 begins to decrease. When the restrictor member 130 and the vane 132 reach the position 130 shown in FIG. 15B, the vane 132 crosses the jet of exhaled air exiting the variable nozzle 136 or the chamber passage 116, thereby creating a force on the vane 132 that, along with the momentum of the vane 132, the shaft 134, and the restrictor member 130, propels the vane 132 and the restrictor member 130 back to the position shown in FIG. 15A. After the restrictor member 130 and the vane 132 return to the position shown in FIG. 15A, the flow of exhaled air through the chamber inlet 104 is restricted, and the cycle described above repeats itself.

It should be appreciated that, during a single period of exhalation, the cycle described above will repeat numerous times. Thus, by repeatedly moving the restrictor member 130 between a closed position, where the flow of exhaled air through the chamber inlet 104 is restricted, and an open position, where the flow of exhaled air through the chamber inlet 104 is less restricted, an oscillating back pressure is transmitted to the user of the OPEP device 100 and OPEP therapy is administered.

Figure 17:
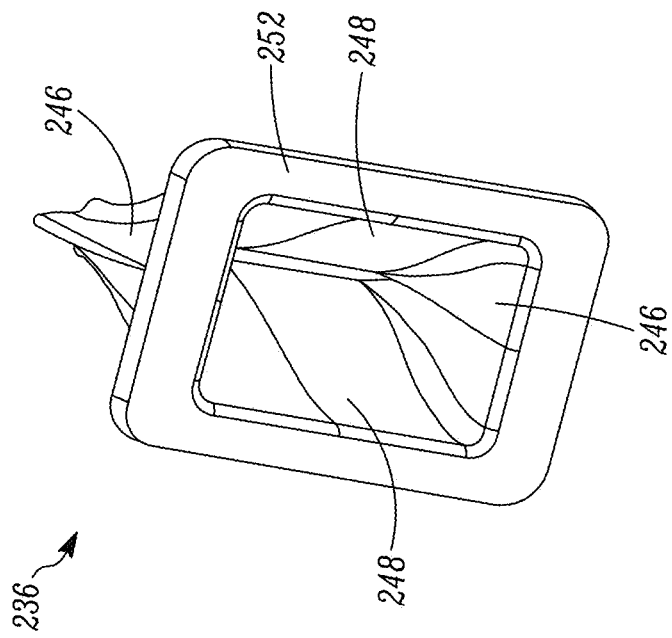
FIG. 17 is a rear perspective view of the variable nozzle of FIG. 16 shown without the flow of exhaled air therethrough.
Figure 16:
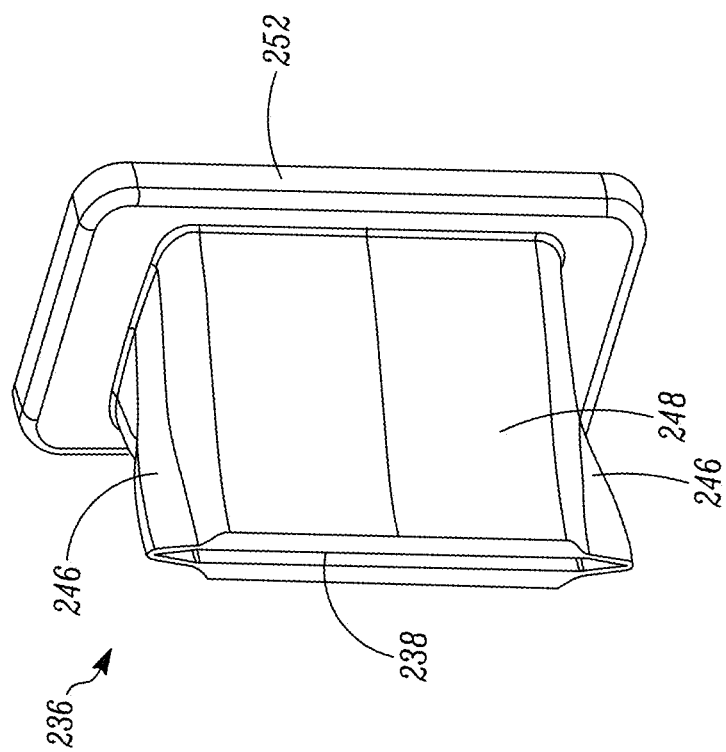
FIG. 16 is a front perspective view of a different embodiment of a variable nozzle shown without the flow of exhaled air therethrough.

Turning now to FIGS. 16-17, an alternative embodiment of a variable nozzle 236 is shown. The variable nozzle 236 may be used in the OPEP device 100 as an alternative to the variable nozzle 136 described above. As shown in FIGS. 16-17, the variable nozzle 236 includes an orifice 238, top and bottom walls 246, side walls 248, and a lip 252 configured to mount the variable nozzle 236 within the housing of the OPEP device 100 between the first chamber 114 and the second chamber 118 in the same manner as the variable nozzle 136. Similar to the variable nozzle 136 shown in FIGS. 12-13, the variable nozzle 236 may be constructed or molded of any material having a suitable flexibility, such as silicone.

During the administration of OPEP therapy, as the orifice 238 of the variable nozzle 236 opens in response to the flow of exhaled air therethrough, the cross-sectional shape of the orifice 238 remains generally rectangular, which results in a lower drop in pressure through the variable nozzle 236 from the first chamber 114 to the second chamber 118. The generally consistent rectangular shape of the orifice 238 of the variable nozzle 236 during increased flow rates is achieved by thin, creased walls formed in the top and bottom walls 246, which allow the side walls 248 to flex easier and with less resistance. A further advantage of this embodiment is that there is no leakage out of the top and bottom walls 246 while exhaled air flows through the orifice 238 of the variable nozzle 236, such as for example, through the V-shaped slits 150 of the variable nozzle 136 shown in FIGS. 12-13.

Those skilled in the art will also appreciate that, in some applications, only positive expiratory pressure (without oscillation) may be desired, in which case the OPEP device 100 may be operated without the restrictor member 130, but with a fixed orifice or manually adjustable orifice instead. The positive expiratory pressure embodiment may also comprise the variable nozzle 136, or the variable nozzle 236, in order to maintain a relatively consistent back pressure within a desired range.

Second Embodiment

Figure 18:
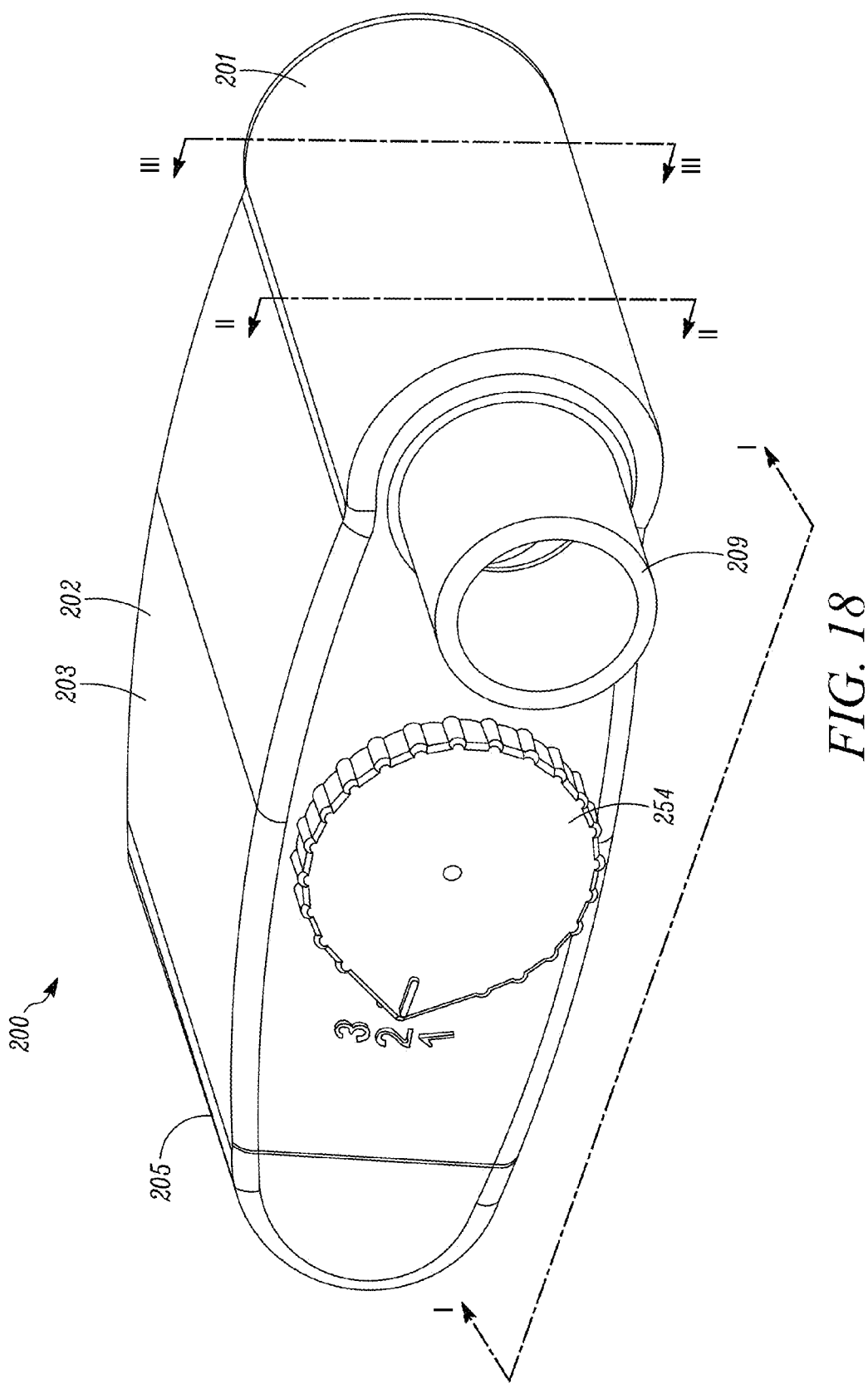
FIG. 18 is a front perspective view of a second embodiment of an OPEP device.
Figure 19:
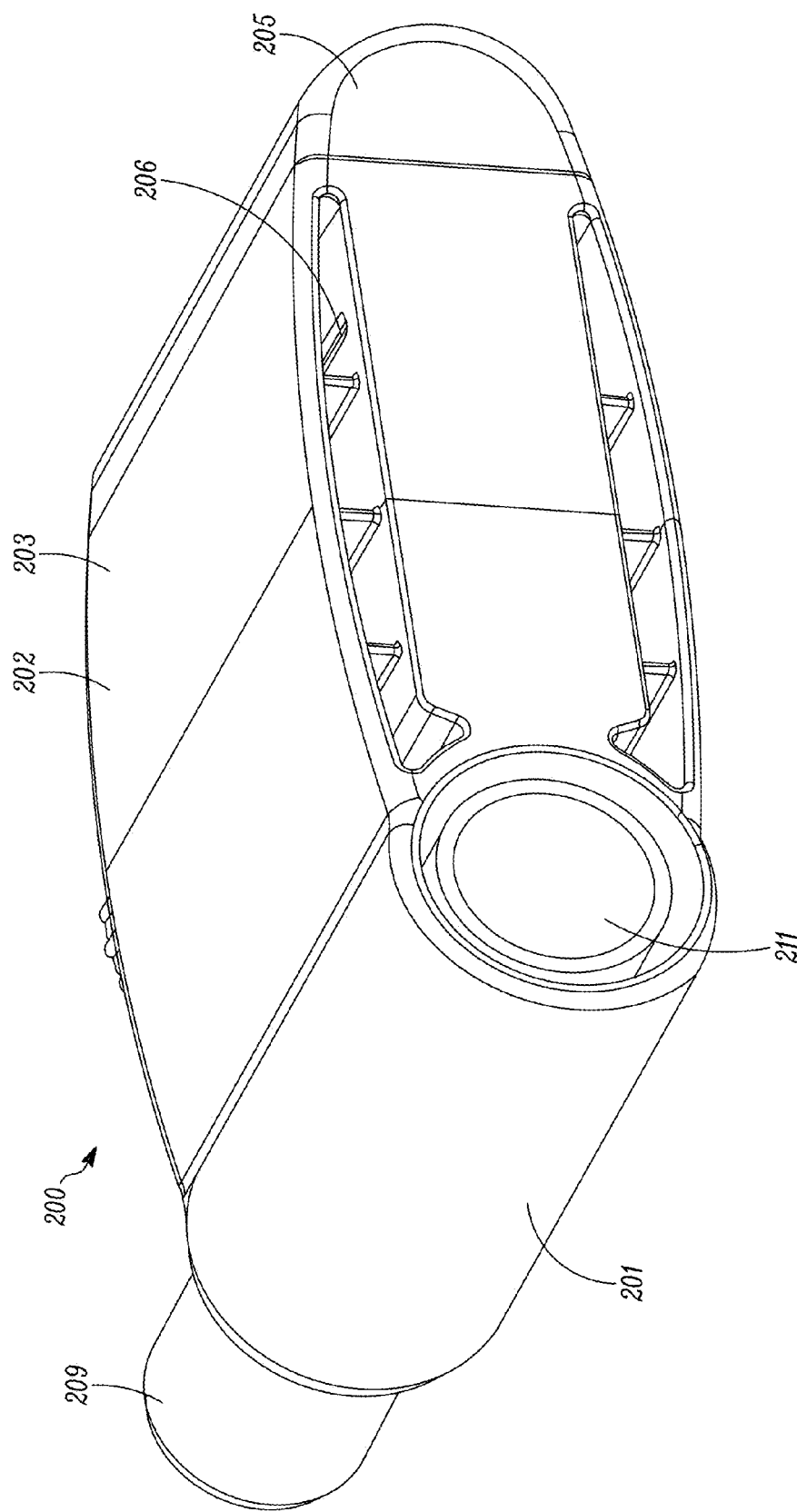
FIG. 19 is a rear perspective view of the OPEP device of FIG. 18.

Turning now to FIGS. 18-19, a front perspective view and a rear perspective view of a second embodiment of an OPEP device 200 is shown. The configuration and operation of the OPEP device 200 is similar to that of the OPEP device 100. However, as best shown in FIGS. 20-24, the OPEP device 200 further includes an adjustment mechanism 253 adapted to change the relative position of the chamber inlet 204 with respect to the housing 202 and the restrictor member 230, which in turn changes the range of rotation of the vane 232 operatively connected thereto. As explained below, a user is therefore able to conveniently adjust both the frequency and the amplitude of the OPEP therapy administered by the OPEP device 200 without opening the housing 202 and disassembling the components of the OPEP device 200.

The OPEP device 200 generally comprises a housing 202, a chamber inlet 204, a first chamber outlet 206 (best seen in FIGS. 23 and 32), a second chamber outlet 208 (best seen in FIGS. 23 and 32), and a mouthpiece 209 in fluid communication with the chamber inlet 204. As with the OPEP device 100, a front section 201, a middle section 203, and a rear section 205 of the housing 202 are separable so that the components contained therein can be periodically accessed, cleaned, replaced, or reconfigured, as required to maintain the ideal operating conditions. The OPEP device also includes an adjustment dial 254, as described below.

As discussed above in relation to the OPEP device 100, the OPEP device 200 may be adapted for use with other or additional interfaces, such as an aerosol delivery device. In this regard, the OPEP device 200 is equipped with an inhalation port 211 (best seen in FIGS. 19, 21, and 23) in fluid communication with the mouthpiece 209 and the chamber inlet 204. As noted above, the inhalation port may include a separate one-way valve (not shown) to permit a user of the OPEP device 200 both to inhale the surrounding air through the one-way valve and to exhale through the chamber inlet 204 without withdrawing the mouthpiece 209 of the OPEP device 200 between periods of inhalation and exhalation. In addition, the aforementioned aerosol delivery devices may be connected to the inhalation port 211 for the simultaneous administration of aerosol and OPEP therapies.

Figure 20:
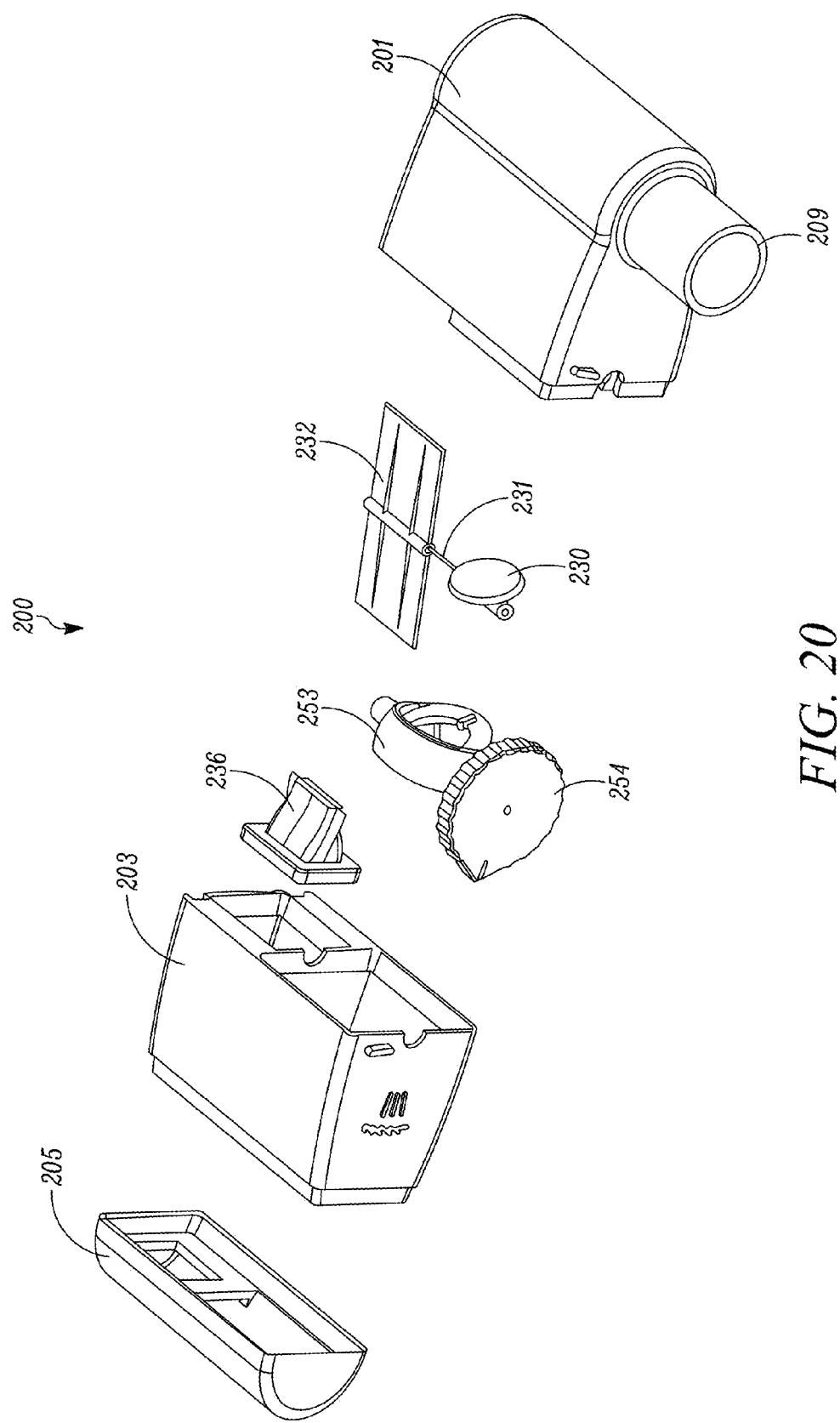
FIG. 20 is an exploded view of the OPEP device of FIG. 18, shown with the internal components of the OPEP device.

An exploded view of the OPEP device 200 is shown in FIG. 20. In addition to the components of the housing described above, the OPEP device 200 includes a restrictor member 230 operatively connected to a vane 232 by a pin 231, an adjustment mechanism 253, and a variable nozzle 236. As shown in the cross-sectional view of FIG. 21, when the OPEP device 200 is in use, the variable nozzle 236 is positioned between the middle section 203 and the rear section 205 of the housing 202, and the adjustment mechanism 253, the restrictor member 230, and the vane 232 form an assembly.

Figure 21:
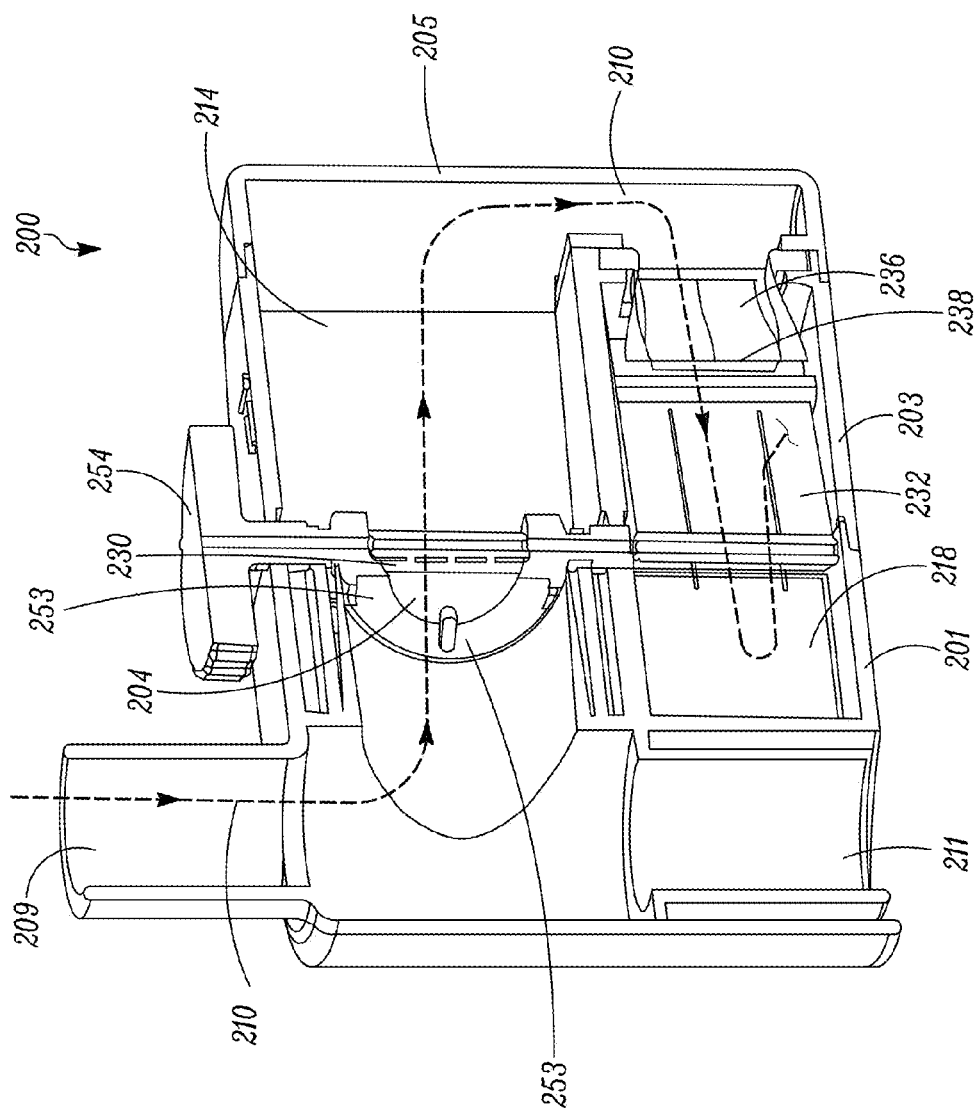
FIG. 21 is a cross-sectional view taken along line I in FIG. 18 of the OPEP device, shown with the internal components of the OPEP device.
Figure 22:
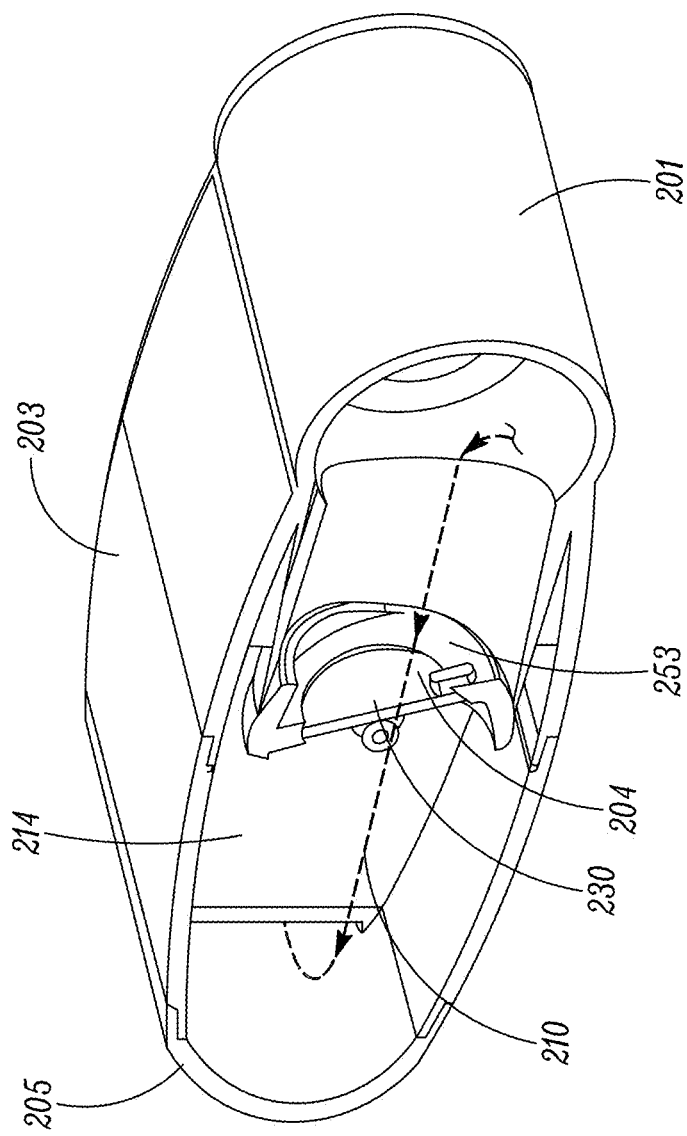
FIG. 22 is a cross-sectional view taken along line II in FIG. 18 of the OPEP device, shown with the internal components of the OPEP device.
Figure 23:
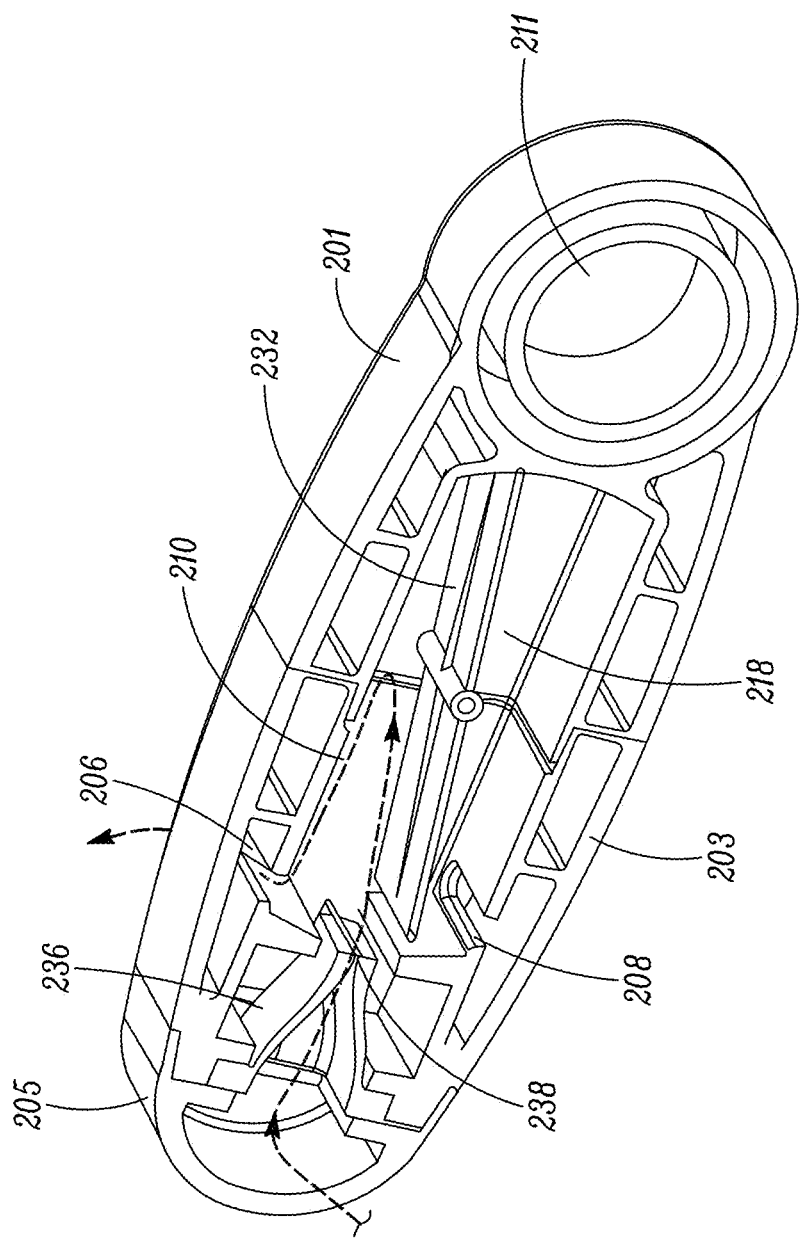
FIG. 23 is a cross-sectional view taken along line III in FIG. 18 of the OPEP device, shown with the internal components of the OPEP device.

Turning to FIGS. 21-23, various cross-sectional perspective views of the OPEP device 200 are shown. As with the OPEP device 100, an exhalation flow path 210, identified by a dashed line, is defined between the mouthpiece 209 and at least one of the first chamber outlet 206 and the second chamber outlet 208 (best seen in FIGS. 23 and 32). As a result of a one-way valve (not-shown) and/or an aerosol delivery device (not shown) attached to the inhalation port 211, the exhalation flow path 210 begins at the mouthpiece 209 and is directed toward the chamber inlet 204, which in operation may or may not be blocked by the restrictor member 230. After passing through the chamber inlet 204, the exhalation flow path 210 enters a first chamber 214 and makes a 180° turn toward the variable nozzle 236. After passing through the orifice 238 of the variable nozzle 236, the exhalation flow path 210 enters a second chamber 218. In the second chamber 218, the exhalation flow path 210 may exit the OPEP device 200 through at least one of the first chamber outlet 206 or the second chamber outlet 208. Those skilled in the art will appreciate that the exhalation flow path 210 identified by the dashed line is exemplary, and that air exhaled into the OPEP device 200 may flow in any number of directions or paths as it traverses from the mouthpiece 209 or chamber inlet 204 to the first chamber outlet 206 or the second chamber outlet 208.

Figure 25:
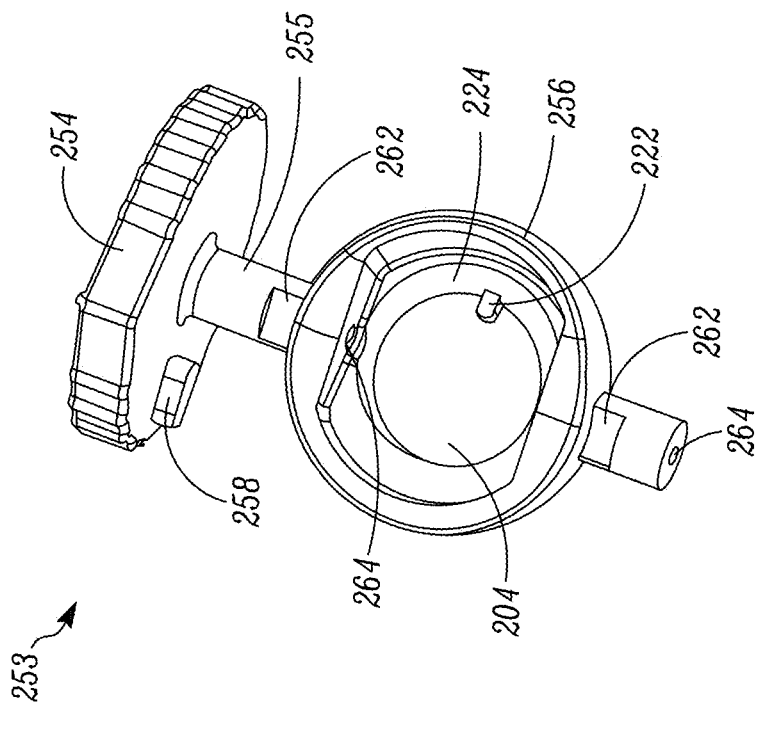
FIG. 25 is a rear perspective view of the adjustment mechanism of FIG. 24.
Figure 24:
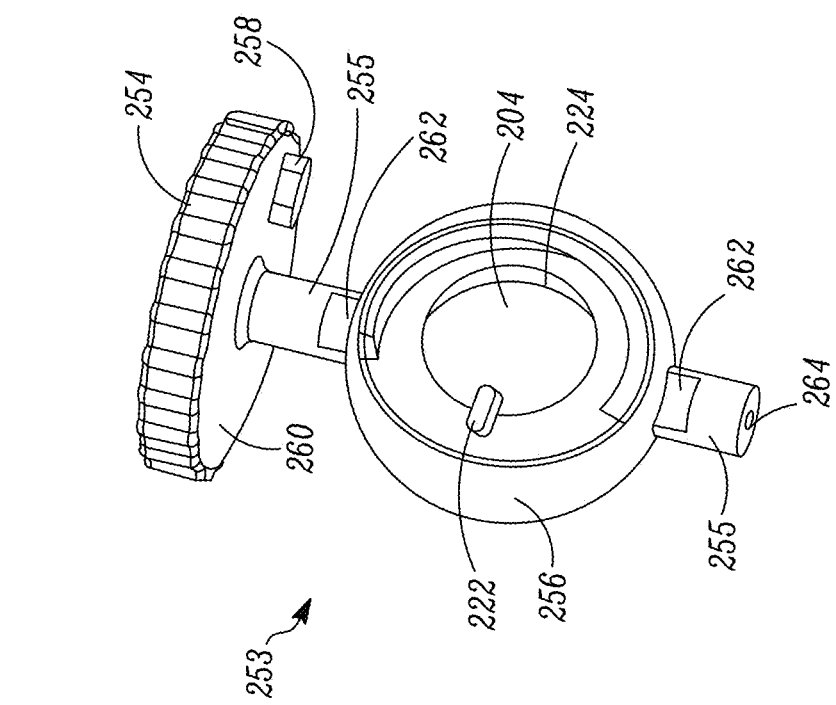
FIG. 24 is a front perspective view of an adjustment mechanism of the OPEP device of FIG. 18.

Referring to FIGS. 24-25, front and rear perspective views of the adjustment mechanism 253 of the OPEP device 200 are shown. In general, the adjustment mechanism 253 includes an adjustment dial 254, a shaft 255, and a frame 256. A protrusion 258 is positioned on a rear face 260 of the adjustment dial, and is adapted to limit the selective rotation of the adjustment mechanism 253 by a user, as further described below. The shaft 255 includes keyed portions 262 adapted to fit within upper and lower bearings 226, 228 formed in the housing 200 (see FIGS. 21 and 28-29). The shaft further includes an axial bore 264 configured to receive the pin 231 operatively connecting the restrictor member 230 and the vane 232. As shown, the frame 256 is spherical, and as explained below, is configured to rotate relative to the housing 202, while forming a seal between the housing 202 and the frame 256 sufficient to permit the administration of OPEP therapy. The frame 256 includes a circular opening defined by a seat 224 adapted to accommodate the restrictor member 230. In use, the circular opening functions as the chamber inlet 204. The frame 256 also includes a stop 222 for preventing the restrictor member 230 from opening in a wrong direction.

Figure 26:
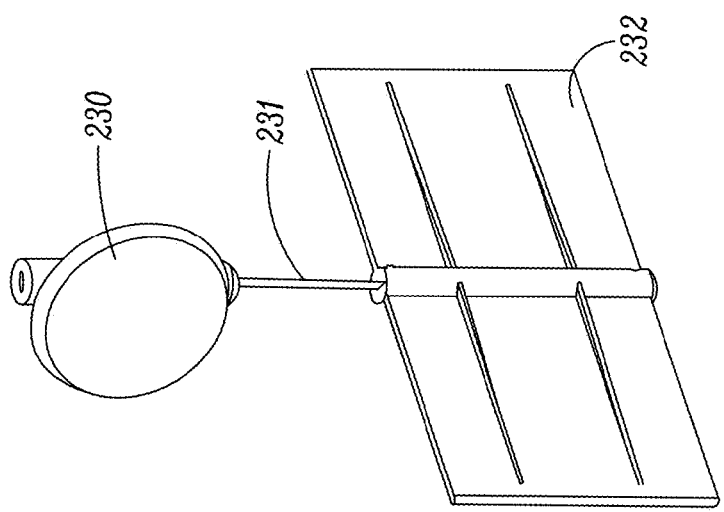
FIG. 26 is a front perspective view of a restrictor member operatively connected to a vane for use in the OPEP device of FIG. 18.

Turning to FIG. 26, a front perspective view of the restrictor member 230 and the vane 232 is shown. The design, materials, and configuration of the restrictor member 230 and the vane 232 may be the same as described above in regards to the OPEP device 100. However, the restrictor member 230 and the vane 232 in the OPEP device 200 are operatively connected by a pin 231 adapted for insertion through the axial bore 264 in the shaft 255 of the adjustment mechanism 253. The pin 231 may be constructed, for example, by stainless steel. In this way, rotation of the restrictor member 230 results in a corresponding rotation of the vane 232, and vice versa.

Figure 27:
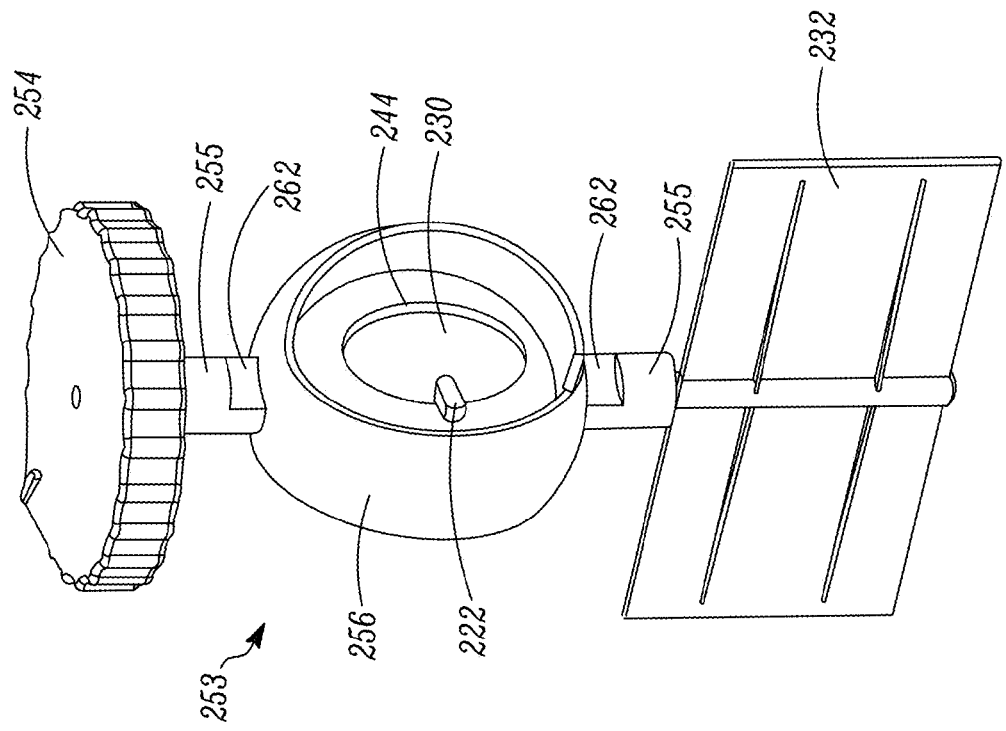
FIG. 27 is a front perspective view of the adjustment mechanism of FIG. 24 assembled with the restrictor member and the vane of FIG. 26.

Turning to FIG. 27, a front perspective view of the adjustment mechanism 253 assembled with the restrictor member 230 and the vane 232 is shown. In this configuration, it can be seen that the restrictor member 230 is positioned such that it is rotatable relative to the frame 256 and the seat 224 between a closed position (as shown), where a flow of exhaled air along the exhalation flow path 210 through the chamber inlet 204 is restricted, and an open position (not shown), where the flow of exhaled air through the chamber inlet 204 is less restricted. As previously mentioned the vane 232 is operatively connected to the restrictor member 230 by the pin 231 extending through shaft 255, and is adapted to move in unison with the restrictor member 230. It can further be seen that the restrictor member 230 and the vane 232 are supported by the adjustment mechanism 253, which itself is rotatable within the housing 202 of the OPEP device 200, as explained below.

Figure 28:
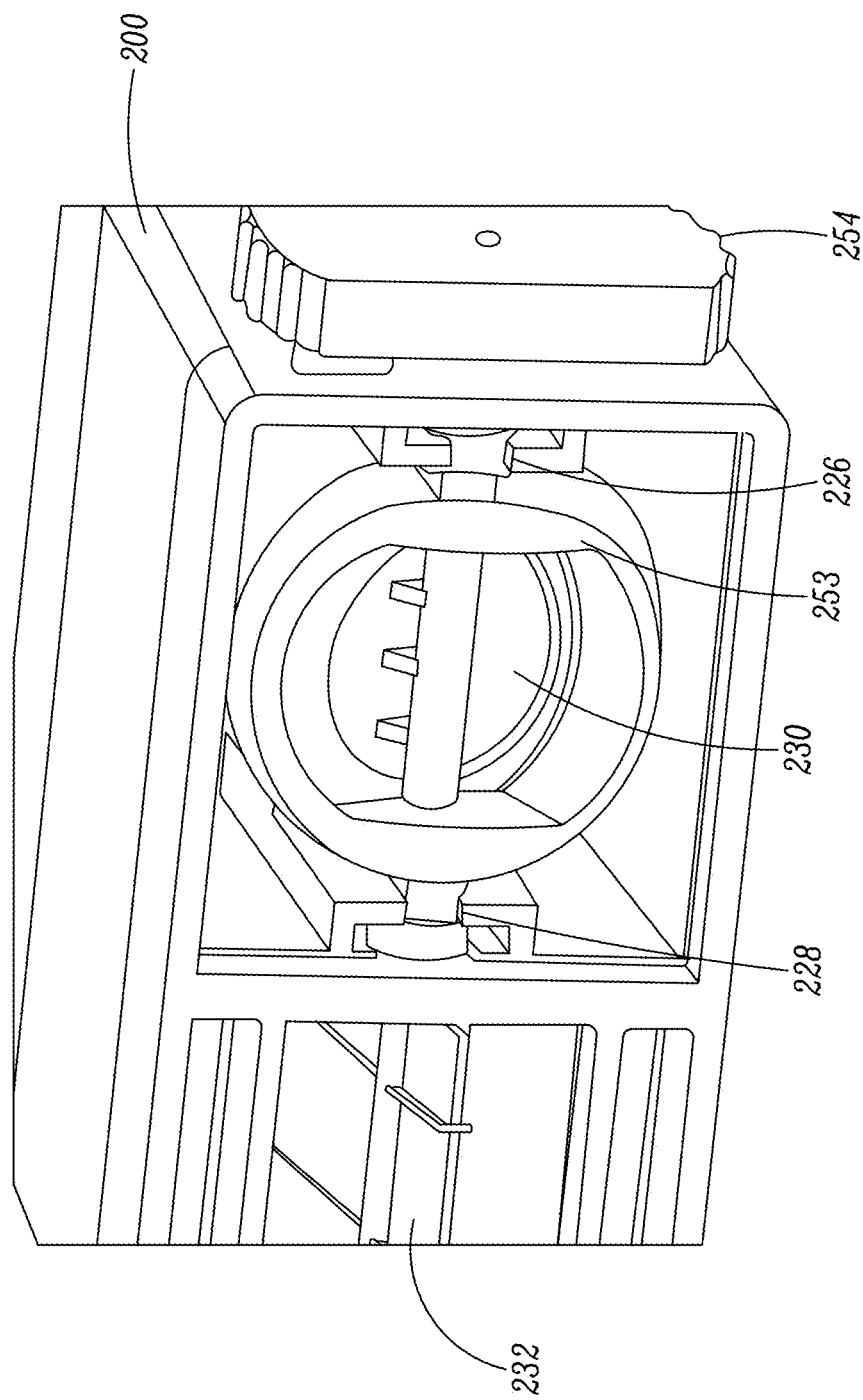
FIG. 28 is a partial cross-sectional view of the assembly of FIG. 27 within the OPEP device of FIG. 18.

FIGS. 28 and 29A-B are partial cross-sectional views illustrating the adjustment mechanism 253 mounted within the housing 202 of the OPEP device 200. As shown in FIG. 28, the adjustment mechanism 253, as well as the restrictor member 230 and the vane 232, are rotatably mounted within the housing 200 about an upper and lower bearing 226, 228, such that a user is able to rotate the adjustment mechanism 253 using the adjustment dial 254. FIGS. 29A-29B further illustrates the process of mounting and locking the adjustment mechanism 253 within the lower bearing 228 of the housing 202. More specifically, the keyed portion 262 of the shaft 255 is aligned with and inserted through a rotational lock 166 formed in the housing 202, as shown in FIG. 29A. Once the keyed portion 262 of the shaft 255 is inserted through the rotational lock 266, the shaft 255 is rotated 90° to a locked position, but remains free to rotate. The adjustment mechanism 253 is mounted and locked within the upper bearing 226 in the same manner.

Figure 30:
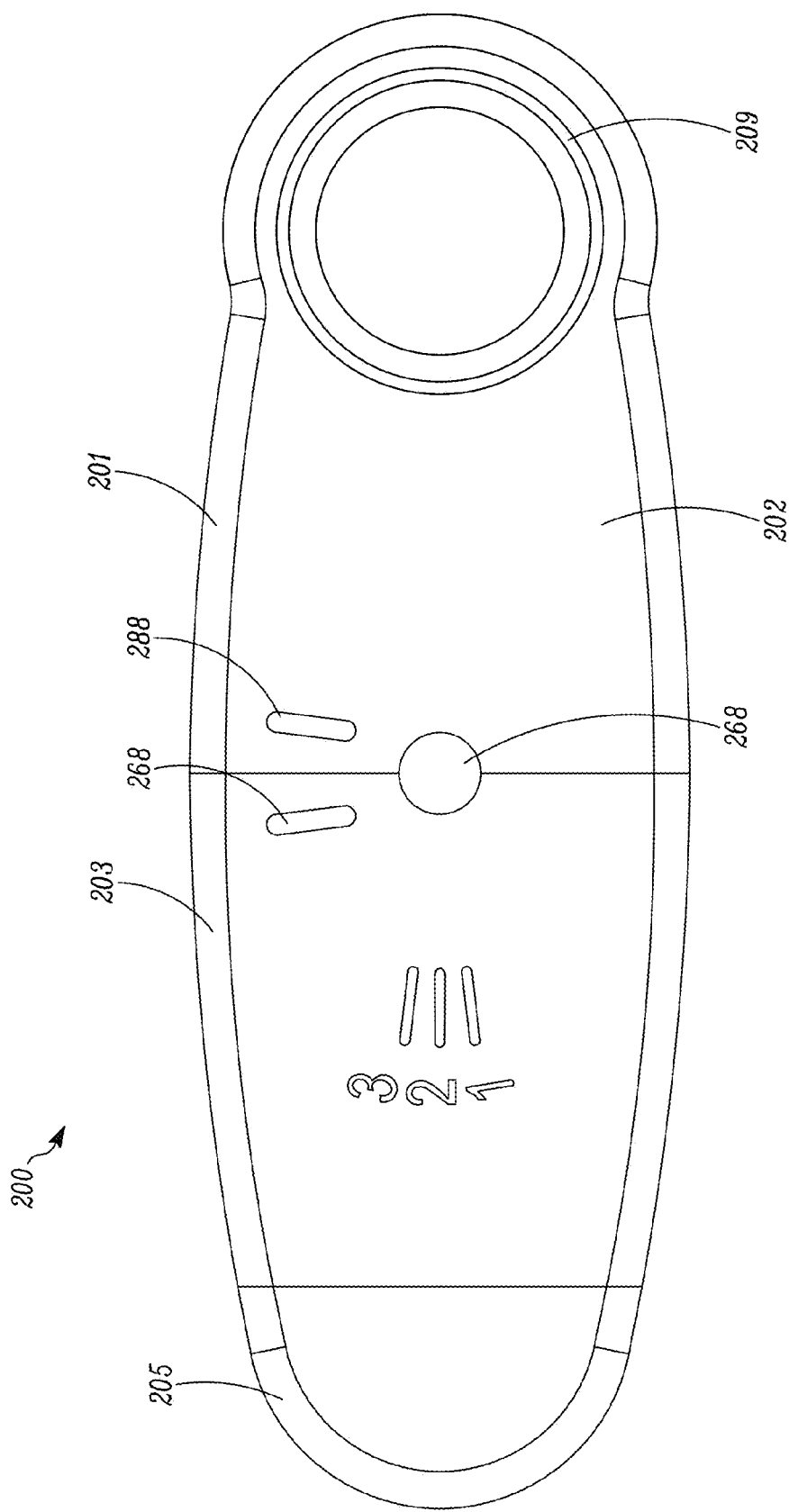
FIG. 30 is a front view of the OPEP device of FIG. 18 illustrating an aspect of the adjustability of the OPEP device.

Once the housing 200 and the internal components of the OPEP device 200 are assembled, the rotation of the shaft 255 is restricted to keep it within a locked position in the rotational lock 166. As shown in a front view of the OPEP device 200 in FIG. 30, two stops 268, 288 are positioned on the housing 202 such that they engage the protrusion 258 formed on the rear face 260 of the adjustment dial 254 when a user rotates the adjustment dial 254 to a predetermined position. For purposes of illustration, the OPEP device 200 is shown in FIG. 30 without the adjustment dial 254 or the adjustment mechanism 253, which would extend from the housing 202 through an opening 269. In this way, rotation of the adjustment dial 254, the adjustment mechanism 253, and the keyed portion 262 of the shaft 255 can be appropriately restricted.

Figure 31:
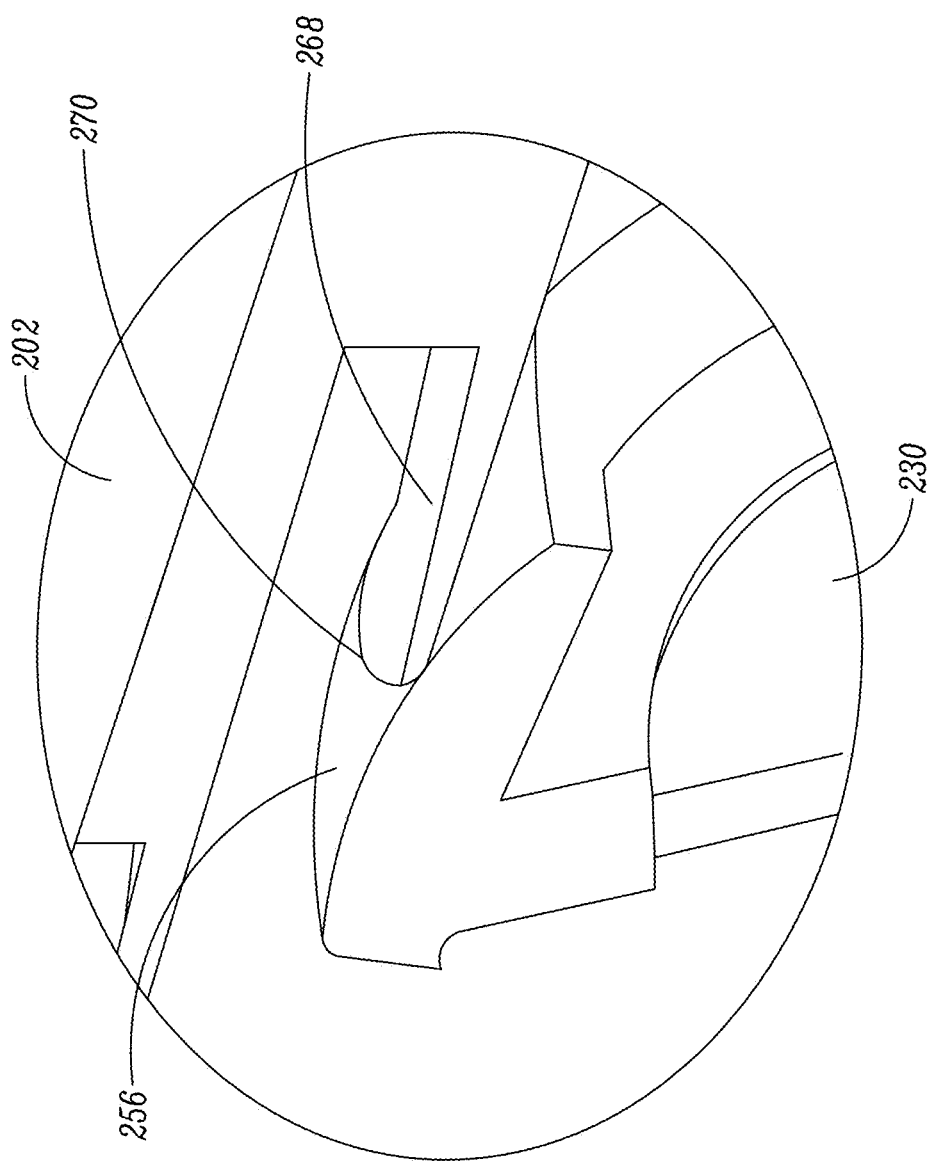
FIG. 31 is a partial cross-sectional view of the assembly of FIG. 27 within the OPEP device of FIG. 18.

Turning to FIG. 31, a partial cross-sectional view of the adjustment mechanism 253 mounted within the housing 200 is shown. As previously mentioned, the frame 256 of the adjustment mechanism 253 is spherical, and is configured to rotate relative to the housing 202, while forming a seal between the housing 202 and the frame 256 sufficient to permit the administration of OPEP therapy. As shown in FIG. 31, a flexible cylinder 271 extending from the housing 202 completely surrounds a portion of the frame 256 to form a sealing edge 270. Like the housing 202 and the restrictor member 230, the flexible cylinder 271 and the frame 256 may be constructed of a low shrink, low friction plastic. One such material is acetal. In this way, the sealing edge 270 contacts the frame 256 for a full 360° and forms a seal throughout the permissible rotation of the adjustment member 253.

Figure 32B:
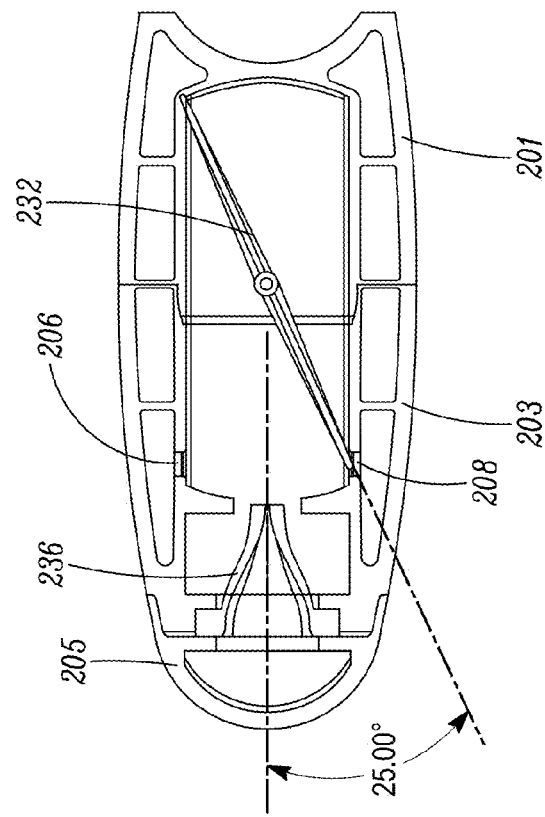
FIGS. 32A-B are partial cross-sectional views taken along line III in FIG. 18 of the OPEP device, illustrating possible configurations of the OPEP device.
Figure 32A:
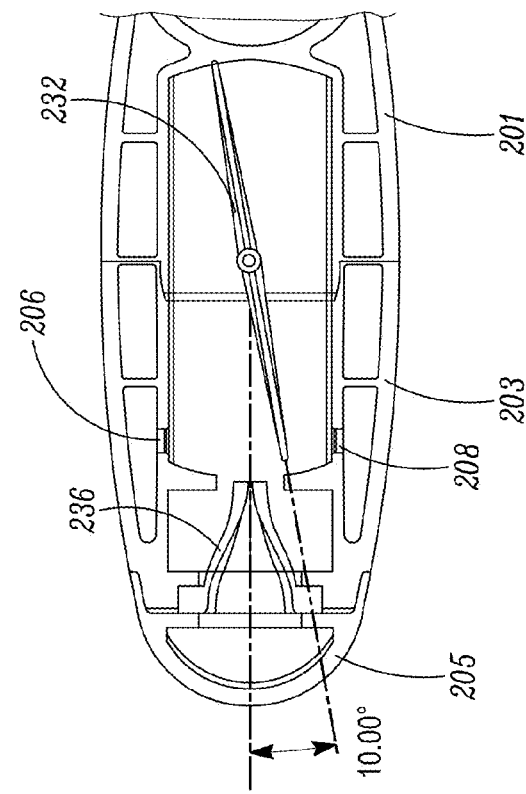
Figure 33A:
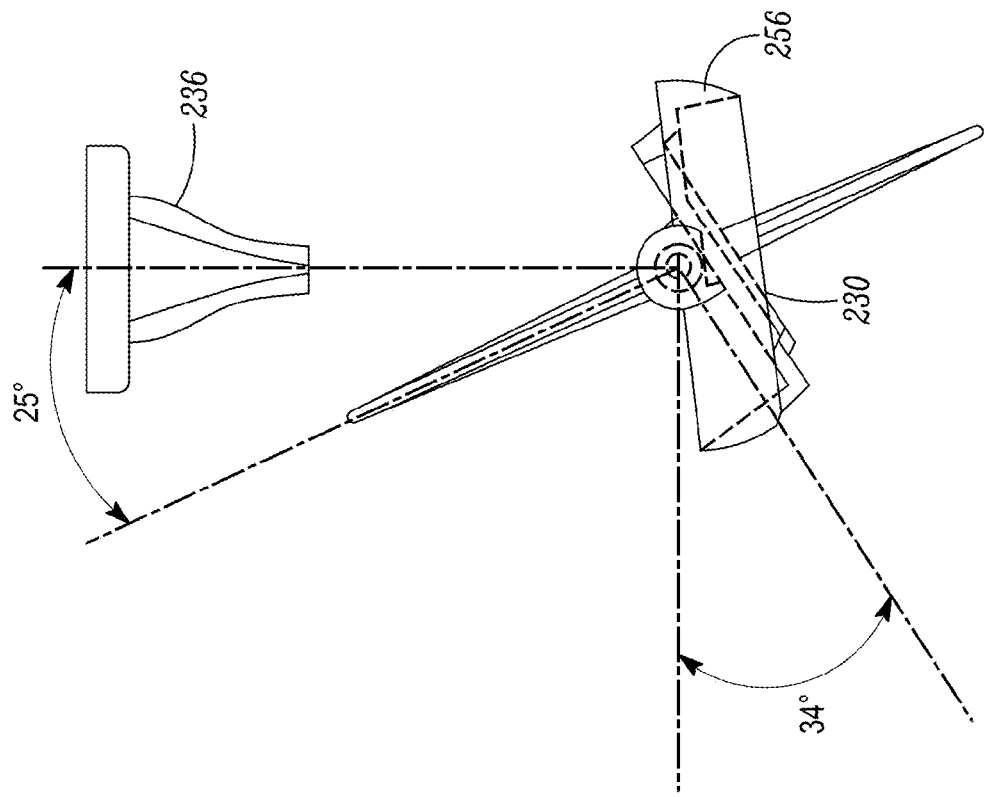
FIGS. 33A-B are top phantom views illustrating the adjustability of the OPEP device of FIG. 18.
Figure 33B:
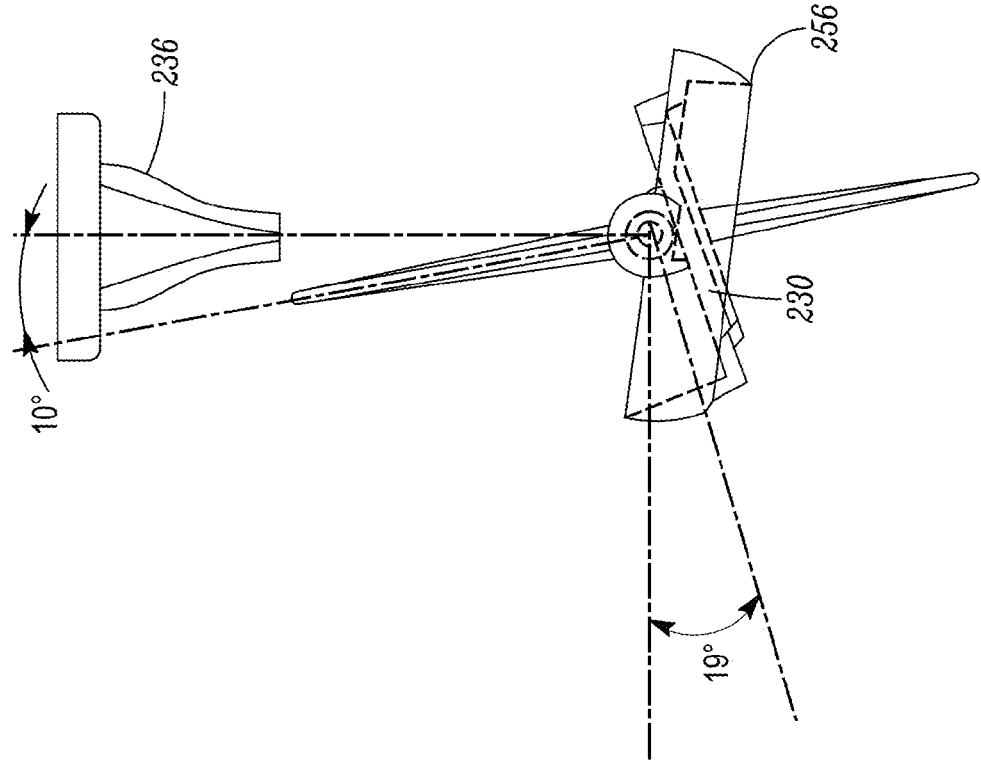
Figure 34A:
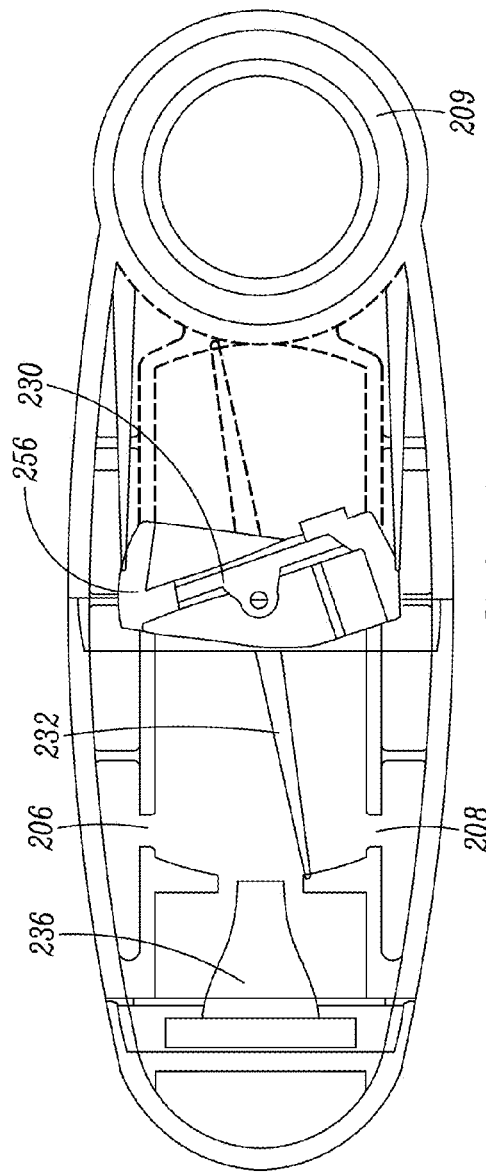
FIGS. 34A-B are top phantom views of the OPEP device of FIG. 18, illustrating the adjustability of the OPEP device.
Figure 34B:
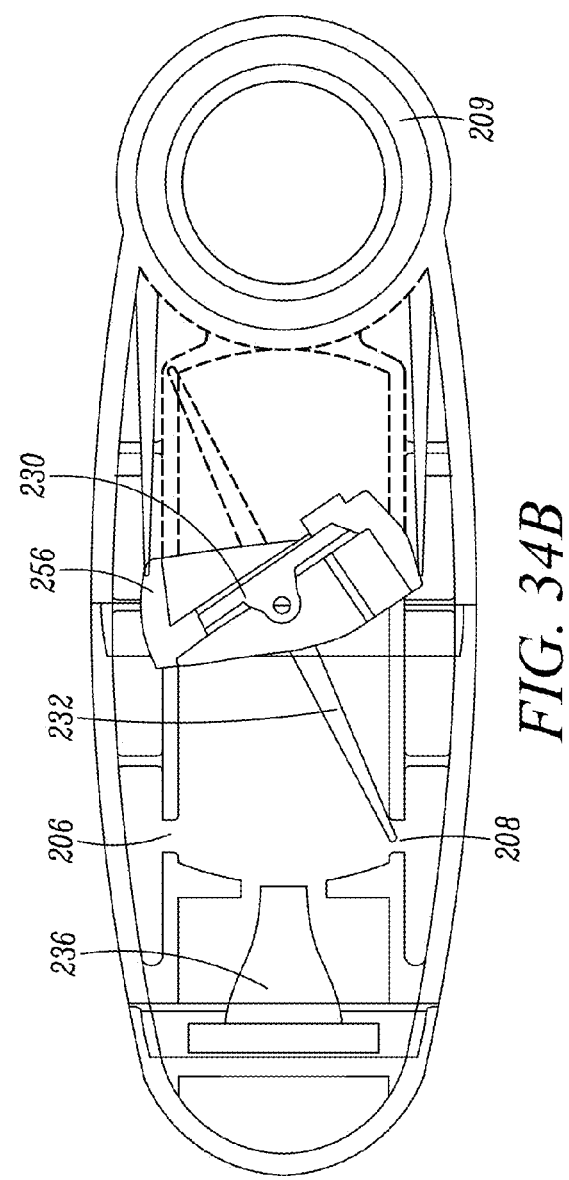

The selective adjustment of the OPEP device 200 will now be described with reference to FIGS. 32A-B, 33A-B, and 34A-B. FIGS. 32A-B are partial cross-sectional views of the OPEP device 200; FIGS. 33A-B are illustrations of the adjustability of the OPEP device 200; and, FIGS. 34A-B are top phantom views of the OPEP device 200. As previously mentioned with regards to the OPEP device 100, it is preferable that the vane 232 and the restrictor member 230 are configured such that when the OPEP device 200 is fully assembled, the angle between a centerline of the variable nozzle 236 and the vane 232 is between 10° and 25° when the restrictor member 230 is in a closed position. However, it should be appreciated that the adjustability of the OPEP device 200 is not limited to the parameters described herein, and that any number of configurations may be selected for purposes of administering OPEP therapy within the ideal operating conditions.

FIG. 32A shows the vane 232 at an angle of 10° from the centerline of the variable nozzle 236, whereas FIG. 32B shows the vane 232 at an angle of 25° from the centerline of the variable nozzle 236. FIG. 33A illustrates the necessary position of the frame 256 (shown in phantom) relative to the variable nozzle 236 such that the angle between a centerline of the variable nozzle 236 and the vane 232 is 10° when the restrictor member 230 is in the closed position. FIG. 33B, on the other hand, illustrates the necessary position of the frame 256 (shown in phantom) relative to the variable nozzle 236 such that the angle between a centerline of the variable nozzle 236 and the vane 232 is 25° when the restrictor member 230 is in the closed position.

Referring to FIGS. 34A-B, side phantom views of the OPEP device 200 are shown. The configuration shown in FIG. 34A corresponds to the illustrations shown in FIGS. 32A and 33A, wherein the angle between a centerline of the variable nozzle 236 and the vane 232 is 10° when the restrictor member 230 is in the closed position. FIG. 34B, on the other hand, corresponds to the illustrations shown in FIGS. 32B and 33B, wherein the angle between a centerline of the variable nozzle 236 and the vane 232 is 25° when the restrictor member 230 is in the closed position. In other words, the frame 256 of the adjustment member 253 has been rotated counter-clockwise 15°, from the position shown in FIG. 34A, to the position shown in FIG. 34B, thereby also increasing the permissible rotation of the vane 232.

In this way, a user is able to rotate the adjustment dial 254 to selectively adjust the orientation of the chamber inlet 204 relative to the restrictor member 230 and the housing 202. For example, a user may increase the frequency and amplitude of the OPEP therapy administered by the OPEP device 200 by rotating the adjustment dial 254, and therefore the frame 256, toward the position shown in FIG. 34A. Alternatively, a user may decrease the frequency and amplitude of the OPEP therapy administered by the OPEP device 200 by rotating the adjustment dial 254, and therefore the frame 256, toward the position shown in FIG. 34B. Furthermore, as shown for example in FIGS. 18 and 30, indicia may be provided to aid the user in the setting of the appropriate configuration of the OPEP device 200.

Operating conditions similar to those described below with reference to the OPEP device 800 may also be achievable for an OPEP device according to the OPEP device 200.

Third Embodiment

Turning now to FIGS. 35-38, a third embodiment of an OPEP device 300 is shown. As described below, with the exception of an adjustment mechanism 353, the design and operation of the OPEP device 300 is the same as the OPEP device 200. For example, as seen in the front perspective view of FIG. 35, a housing 302 of the OPEP device 300 includes a mouthpiece 309, a first chamber outlet 306, and a second chamber outlet (not shown) positioned opposite the first chamber outlet 306. The housing 302 is formed of a front section 301, a middle section 303, and a rear section 305. As shown in the cross-sectional view of FIG. 36, the OPEP device 300 also includes a restrictor member 330 operatively connected to a vane 332 by a shaft (not shown), and a variable nozzle 336 separating a first chamber 314 and a second chamber 318. Finally, an exhalation flow path 310, identified by a dashed line, is formed between the mouthpiece 309 and at least one of the first chamber outlet 306 and the second chamber outlet. Those skilled in the art will appreciate that the exhalation flow path 310 identified by the dashed line is exemplary, and that air exhaled into the OPEP device 300 may flow in any number of directions or paths as it traverses from the mouthpiece 309 or chamber inlet 304 to the first chamber outlet 306 or the second chamber outlet.

Figure 36:
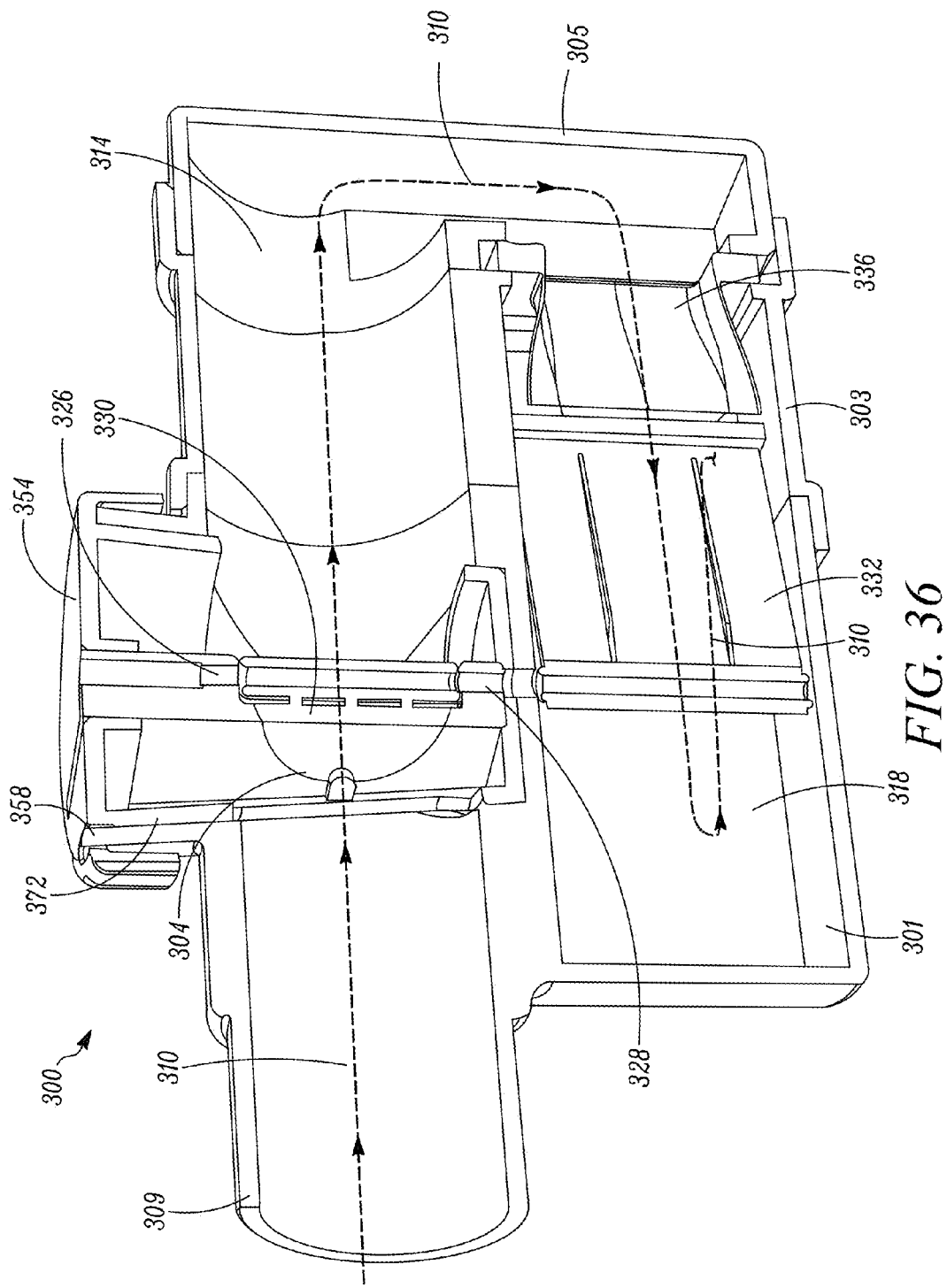
FIG. 36 is a cross-sectional view taken along line I in FIG. 35 of the OPEP device.
Figure 38:
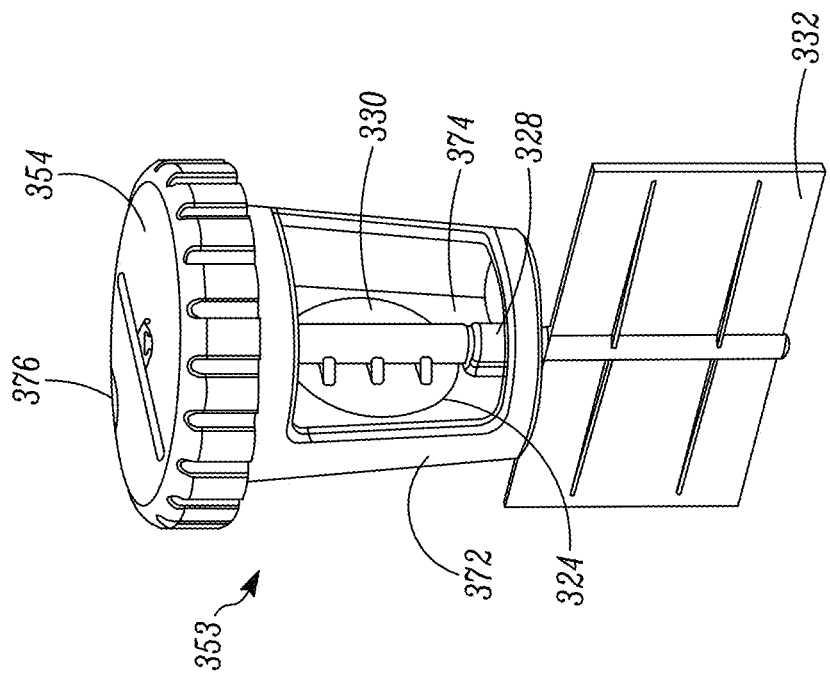
FIG. 38 is a rear perspective view of the assembly of FIG. 37.
Figure 37:
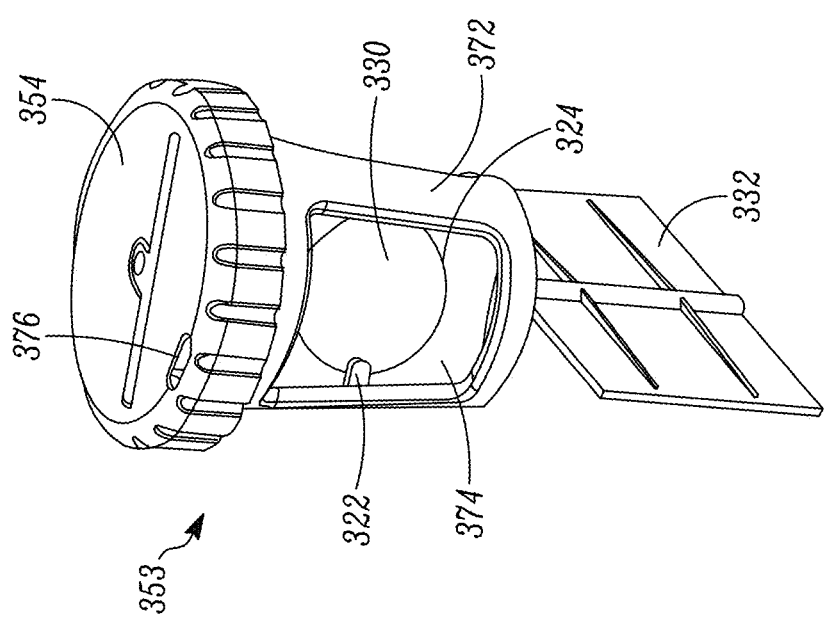
FIG. 37 is a front perspective view of an adjustment mechanism of the OPEP device of FIG. 35 assembled with a restrictor member and a vane.

Referring to FIGS. 37-38, a front perspective view and a rear perspective view of the adjustment mechanism 353 assembled with the restrictor member 330 and the vane 332 are shown. The adjustment mechanism 353 is comprised of a cup 372 shaped to fit within the housing 302 such that a user may rotate the cup 372 relative to the housing 302 via an adjustment dial 354. A wall 374 extends through the central portion of the cup 372. The wall 372 includes an opening defined by a seat 324 shaped to accommodate the restrictor member 330. As seen in FIG. 36, the opening operates as the chamber inlet 304 during the administration of OPEP therapy. The cup 372 further includes an upper bearing 326 and a lower bearing 328 adapted to rotatably mount the restrictor member 330, the vane 332, and the shaft (not shown) to the adjustment mechanism 353, such that the restrictor member 330 and the vane 332 are rotatable relative to the cup 372. The wall also includes a stop 322 to prevent the restrictor member 330 from opening in a wrong direction.

Figure 35:
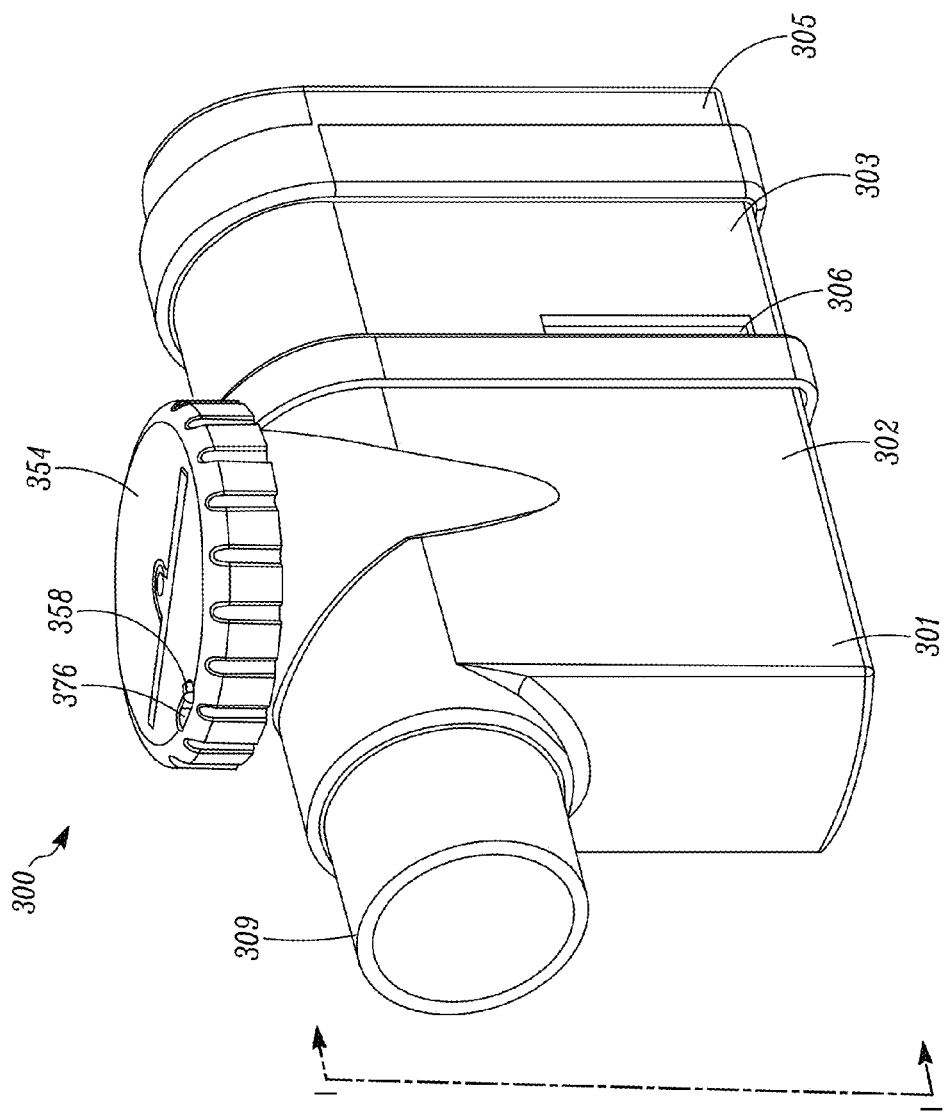
FIG. 35 is a front perspective view of a third embodiment of an OPEP device.

When the OPEP device 300 is fully assembled as shown in FIGS. 35-36, a user is able to rotate the adjustment dial 354 relative to the housing 302 to selectively adjust the frequency and amplitude of the OPEP therapy administered by the OPEP device 300. Similar to the adjustment mechanism 253 of the OPEP device 200, a user may adjust the orientation of the chamber inlet 304 relative to the restrictor member 330 in the OPEP device 300 by rotating the adjustment dial 354, thereby rotating the cup 372 and the wall 374 relative to the restrictor member 330 and the housing 302. A user may increase the frequency and amplitude of the OPEP therapy administered by the OPEP device 300 by rotating the adjustment dial 354, and therefore the wall 374, in the clockwise direction. Alternatively, a user may decrease the frequency and amplitude of the OPEP therapy administered by the OPEP device 300 by rotating the adjustment dial 354, and therefore the wall 374, in the counter-clockwise direction. As shown in FIGS. 35-36, a protrusion 358 extending from the housing 302 through a slot 376 in the adjustment dial 354 may be provided to restrict the rotation of the adjustment dial 354 such that the permissible configurations of the OPEP device 300 are limited, and the ideal operating conditions are maintained.

Operating conditions similar to those described below with reference to the OPEP device 800 may also be achievable for an OPEP device according to the OPEP device 300.

Fourth Embodiment

Figure 39:
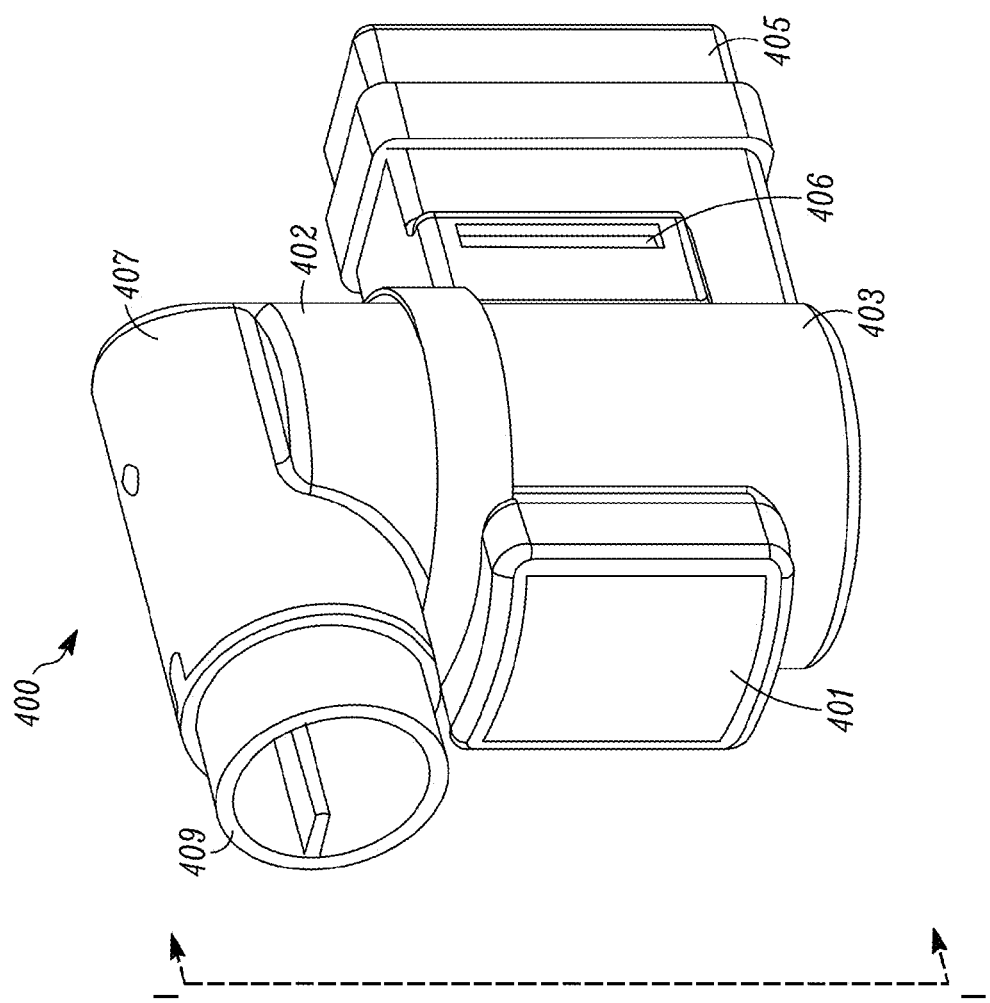
FIG. 39 is a front perspective view of a fourth embodiment of an OPEP device.
Figure 40:
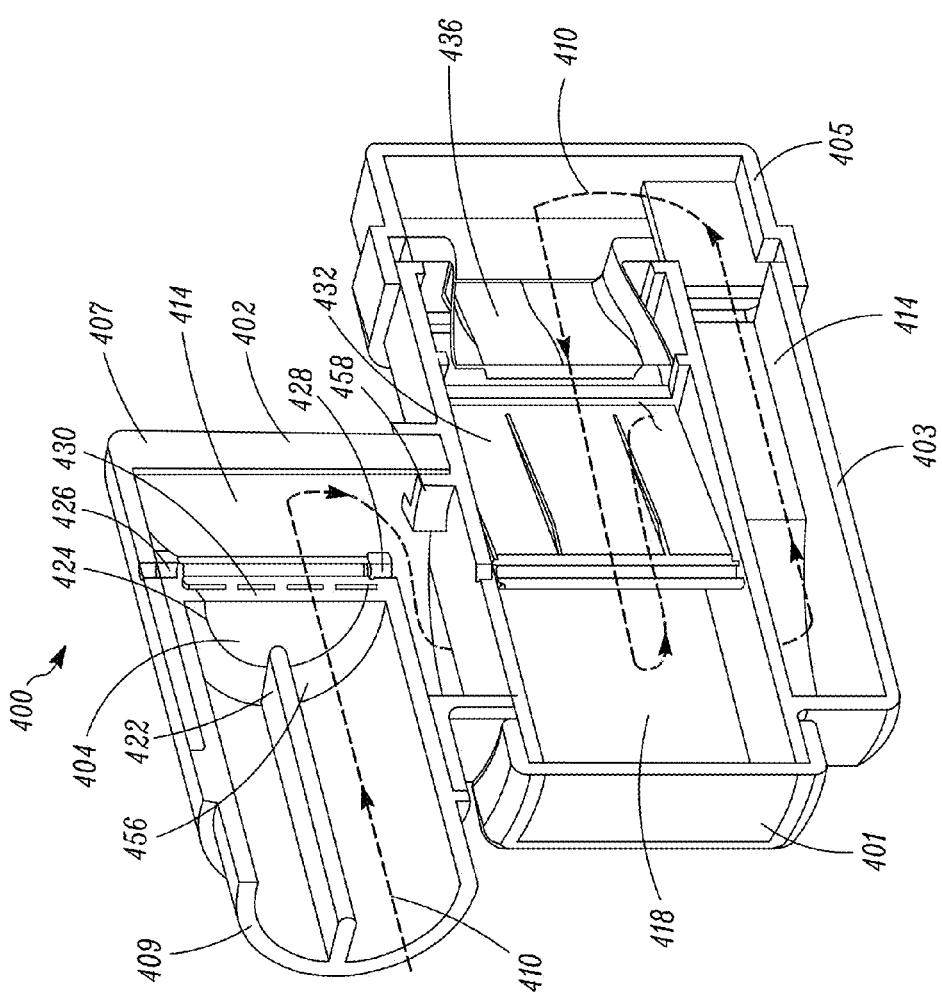
FIG. 40 is a cross-sectional view taken along line I in FIG. 39 of the OPEP device.

Turning to FIGS. 39-40, a fourth embodiment of an OPEP device 400 is shown. Although the configuration of the OPEP device 400 differs from that of the OPEP device 300 and the OPEP device 200, the internal components and operation of the OPEP device 400 are otherwise the same. For example, as seen in the front perspective view of FIG. 39, a housing 402 of the OPEP device 400 includes a mouthpiece 409, a first chamber outlet 406, and a second chamber outlet 408 (best seen in FIGS. 41A-41B) positioned opposite the first chamber outlet. The housing 402 is formed of a front section 401, a middle section 403, and a rear section 405, as well as an upper section 407 adapted to rotate relative to the front section 401, the middle section 403, and the rear section 405.

As seen in the cross-sectional view of FIG. 40, the OPEP device 400 further includes a restrictor member 430 operatively connected to a vane 432 by a shaft (not shown), and a variable nozzle 436 separating a first chamber 414 and a second chamber 418. The upper section 407 of the housing 402 includes a frame 456 having a seat 424 shaped to accommodate the restrictor member 430, a stop 422 to prevent the restrictor member 430 from opening in a wrong direction, as well as an upper bearing 426 and a lower bearing 428 about which the shaft (not shown) operatively connecting the restrictor member 430 and the vane 436 is rotatably mounted. In operation, the seat 422 defines the chamber inlet 404. Consequently, the restrictor member 430 is rotatable relative to the seat 422 and the chamber inlet 404.

As with the previously described embodiments, an exhalation flow path 410, identified by a dashed line, is formed between the mouthpiece 409 and at least one of the first chamber outlet 406 and the second chamber outlet 408. Once again, those skilled in the art will appreciate that the exhalation flow path 410 identified by the dashed line is exemplary, and that air exhaled into the OPEP device 400 may flow in any number of directions or paths as it traverses from the mouthpiece 409 or chamber inlet 404 to the first chamber outlet 406 or the second chamber outlet 408. Due to the configuration of the OPEP device 400, the exhalation flow path 410 differs from those of the embodiments described above. More specifically, the exhalation flow path 410 begins at the mouthpiece 409 formed in the upper section 407 of the housing 402, passes through the chamber inlet 404, and enters into a first chamber 114. In the first chamber 414, the exhalation flow path makes a 180° turn in the direction of the front section 401 of the housing 402, followed by a 90° turn toward the bottom of the OPEP device 400, past a second chamber 418 of the housing 402. The exhalation flow path 410 then makes a 90° turn toward the rear section 405 of the housing 402, where it makes another 180° turn and passes through a variable nozzle 436, and enters into the second chamber 418. In the second chamber 418, the exhalation flow path 410 may exit the OPEP device 410 through at least one of the first chamber outlet 406 or the second chamber outlet 408.

As seen in FIGS. 40 and 41A-B, the upper section 407 of the housing 402 is rotatable relative to the front section 401, the middle section 403, and the rear section 405 of the housing 402. In this way, a user is able to rotate the upper section 407 relative to the front section 401, the middle section 403, and the rear section 405 to selectively adjust the orientation of the chamber inlet 404 relative to the restrictor member 430 and the housing 402, and thereby selectively adjust the frequency and amplitude of the OPEP therapy administered by the OPEP device 400, in a similar manner as previously described in relation to the adjustability of the OPEP device 200. For example, a user may increase the frequency and amplitude of the OPEP therapy administered by the OPEP device 400 by rotating the upper section 407, and therefore the seat 422, relative to the front section 401, the middle section 403, and the rear section 405, toward the position shown in FIG. 41A. Alternatively, a user may decrease the frequency and amplitude of the OPEP therapy administered by the OPEP device 400 by rotating the upper section 407, and therefore the seat 422, relative to the front section 401, the middle section 403, and the rear section 405, toward the position shown in FIG. 41B. Furthermore, as shown in FIGS. 40 and 41A-B, a protrusion 458 extending from the middle section 403 of the housing 402 may be provided to restrict the rotation of the upper section 407 such that the permissible configurations of the OPEP device 400 are limited, and the ideal operating conditions are maintained.

Operating conditions similar to those described below with reference to the OPEP device 800 may also be achievable for an OPEP device according to the OPEP device 400.

Turning to FIGS. 42-47, various alternative embodiments of the OPEP device 100 are shown. Although the embodiments shown in FIGS. 42-47 and described below are alternative embodiments of the OPEP device 100, it should be appreciated that the disclosed modifications may be applied to any of the embodiments described herein.

Fifth Embodiment

Figure 42:
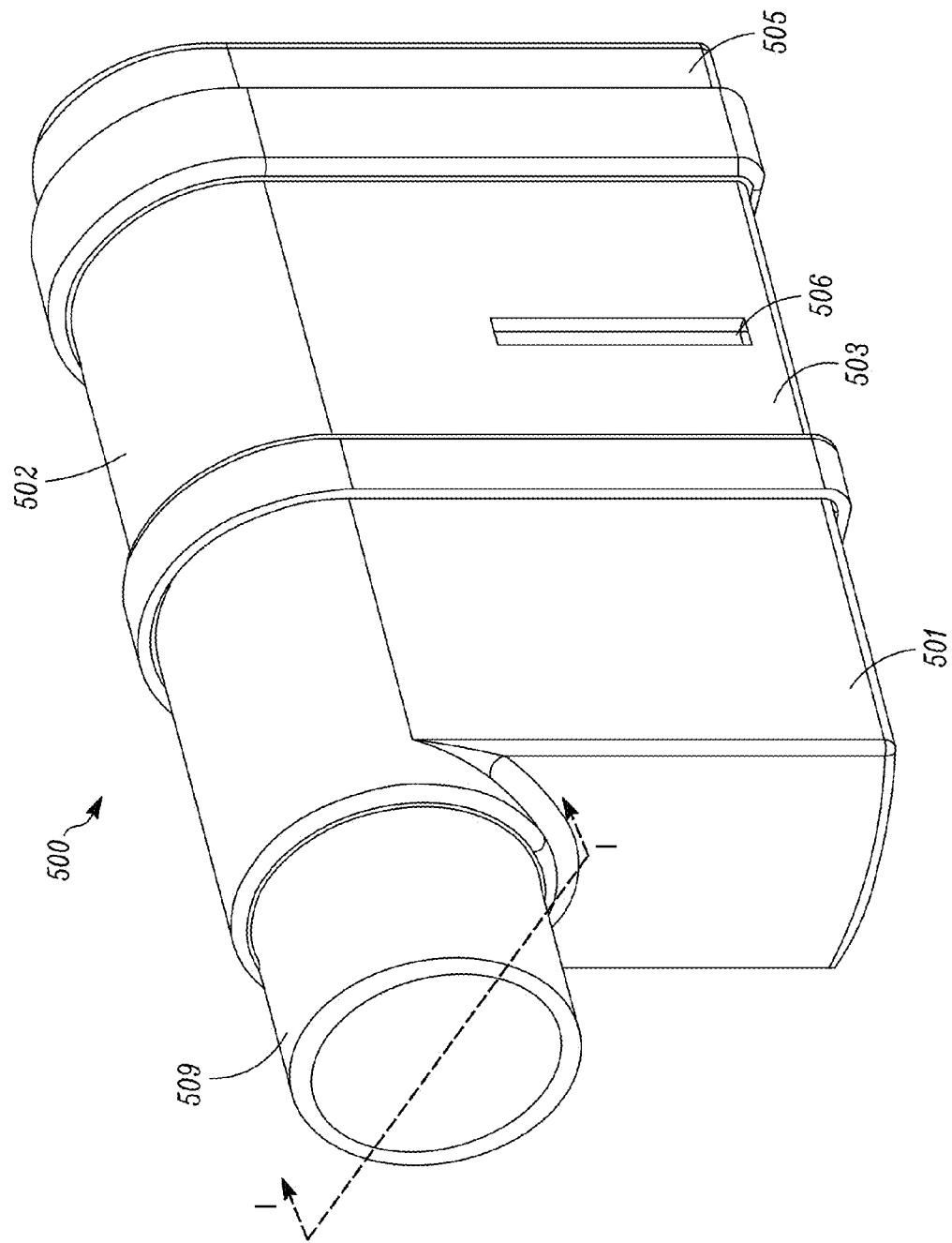
FIG. 42 is a front perspective view of an alternative embodiment of the OPEP device of FIG. 1.
Figure 43:
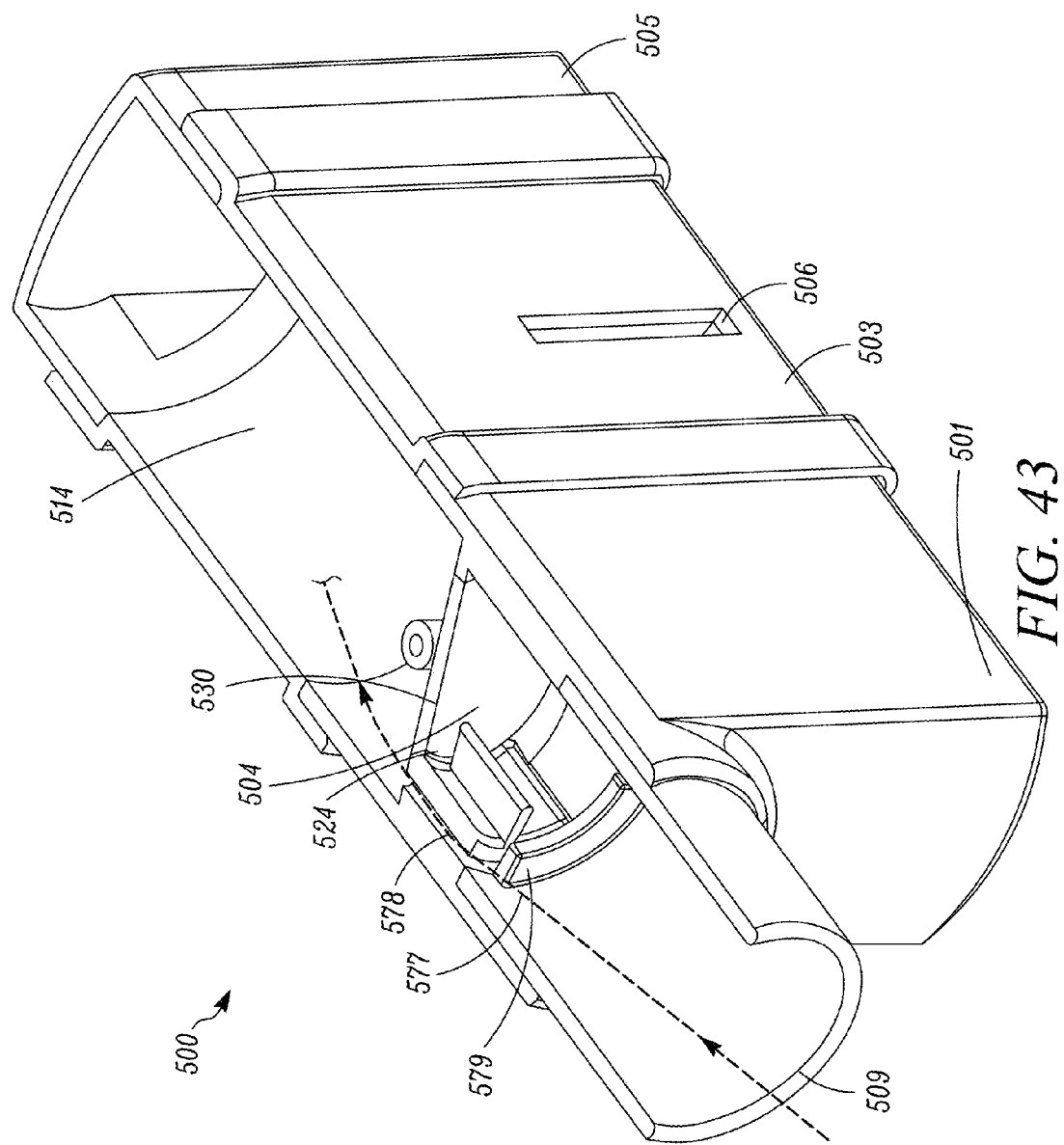
FIG. 43 is a cross-sectional view taken along line I in FIG. 42 of the OPEP device.

Referring to FIGS. 42-43, an OPEP device 500 is shown having a chamber inlet bypass 578 adapted to permit exhaled air into a first chamber 514 without passing through the chamber inlet 504. With the exception of the chamber inlet bypass 578, the OPEP device 500 is otherwise configured and operates the same as the OPEP device 100. As shown, the OPEP device 500 includes a housing 502 comprising a front section 501, a middle section 503, and a rear section 505. The housing is also associated with a mouthpiece 509, and includes a first chamber outlet 506 and a second chamber outlet (not shown) opposite the first chamber outlet 506. As seen in the cross-sectional view of the FIG. 43, the OPEP device 500 includes a restrictor member 530 positioned relative to a seat 524 about the chamber inlet 504 such that it is moveable between a closed position, where the flow of exhaled air through the chamber inlet 504 is restricted, and an open position, where the flow of exhaled air through the chamber inlet 504 is less restricted. The OPEP device 500 further includes a chamber inlet bypass 578 that allows a small amount of exhaled air to move past the chamber inlet 504 and the restrictor member 530 at all times. An exemplary flow path 577 through the chamber inlet bypass 578 is identified in FIG. 43 by a dashed line. By permitting a small amount of exhaled air to bypass the chamber inlet 504 and the restrictor member 530 through the chamber inlet bypass 578, the amplitude of the OPEP therapy administered by the OPEP device 500 is decreased, while the frequency remains substantially unaffected.

Furthermore, a regulation member 579 extending from the mouthpiece 509 permits a user to selectively adjust the amount of exhaled air allowed to flow through the chamber inlet bypass 578. For example, as shown in FIG. 43, a user may rotate the mouthpiece 509 relative to the front section 501 of the housing 502, thereby rotating the regulation member 579 relative to the chamber inlet bypass 578, to either increase or decrease the cross-sectional area of the chamber inlet bypass 578 through which exhaled air may flow. In this way, the user may selectively adjust the OPEP device 500 to maintain the ideal operating conditions.

Sixth Embodiment

Figure 44:
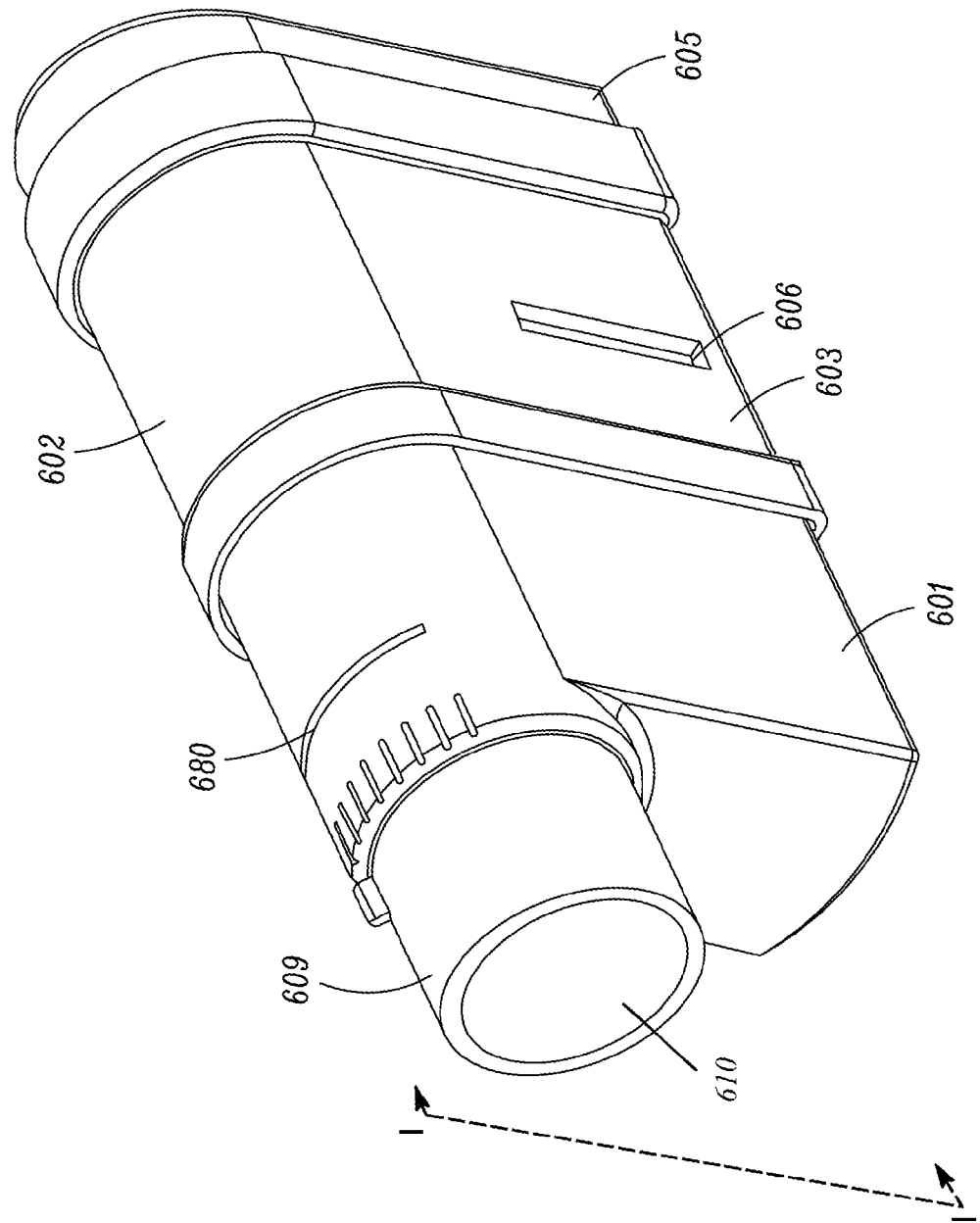
FIG. 44 is a front perspective view of another alternative embodiment of the OPEP device of FIG. 1.
Figure 45:
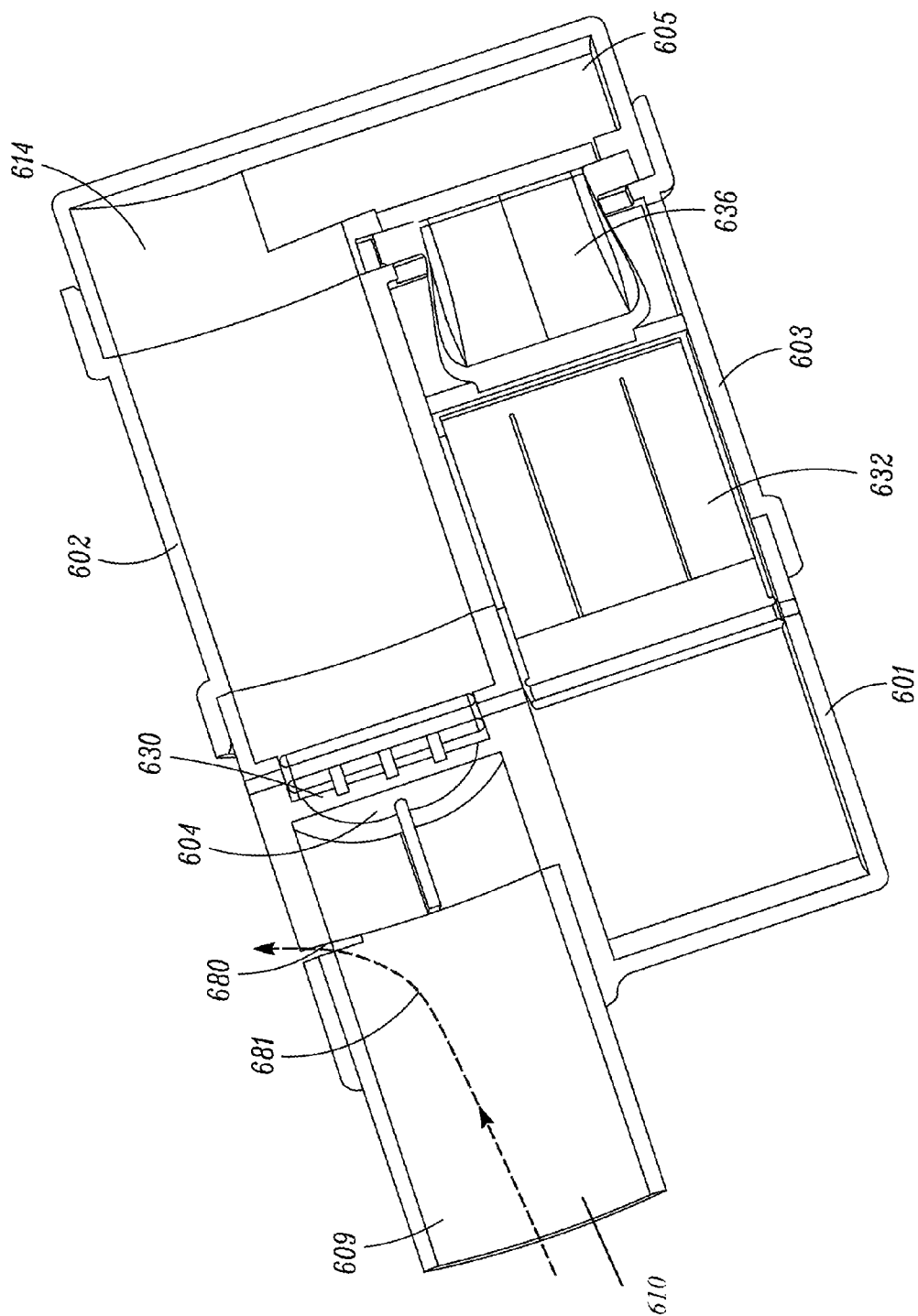
FIG. 45 is a cross-sectional view taken along line I in FIG. 44 of the OPEP device.

Referring to FIGS. 44-45, an OPEP device 600 is shown having an aperture or a control port 680 adapted to permit exhaled air to exit the respiratory treatment device 600 prior to entering a first chamber 614 of the OPEP device 600. With the exception of the control port 680, the OPEP device 600 is otherwise configured and operates the same as the OPEP device 100. As shown, the OPEP device 600 includes a housing 602 comprising a front section 601, a middle section 603, and a rear section 605. The housing 602 is also associated with a mouthpiece 609 having a patient port 610, and includes a first chamber outlet 606 and a second chamber outlet (not shown) positioned opposite the first chamber outlet 606. As seen in the cross-sectional view of the FIG. 45, the OPEP device 600 includes a restrictor member 630 positioned relative to a chamber inlet 604 such that it is moveable between a closed position, where the flow of exhaled air through the chamber inlet 604 is restricted, and an open position, where the flow of exhaled air through the chamber inlet 604 is less restricted, as well as a variable nozzle 636, and a vane 632 operatively connected to the restrictor member 630 by a shaft (not shown). A control port 680 allows a small amount of exhaled air to exit the respiratory treatment device 600 prior to entering the first chamber 614 of the OPEP device 600. An exemplary flow path 681 through the control port 680 is identified in FIG. 45 by a dashed line. By permitting a small amount of exhaled air to exit the OPEP device 600 through the control port 680, the amplitude and the frequency of the OPEP therapy administered by the OPEP device 600 is decreased.

Furthermore, the mouthpiece 609 is rotatable relative to the front section 601 of the housing 602 to permit a user to selectively adjust the amount of exhaled air allowed to exit the respiratory treatment device 600 through the control port 680. For example, as shown in FIG. 45, a user may rotate the mouthpiece 609 relative to the front section 601 to either increase or decrease the cross-sectional area of the control port 680 through which exhaled air may flow. In this way, the user may selectively adjust the OPEP device 600 to maintain the ideal operating conditions.

Operating conditions similar to those described below with reference to the OPEP device 800 may also be achievable for an OPEP device according to the OPEP device 600.

Seventh Embodiment

Figure 46:
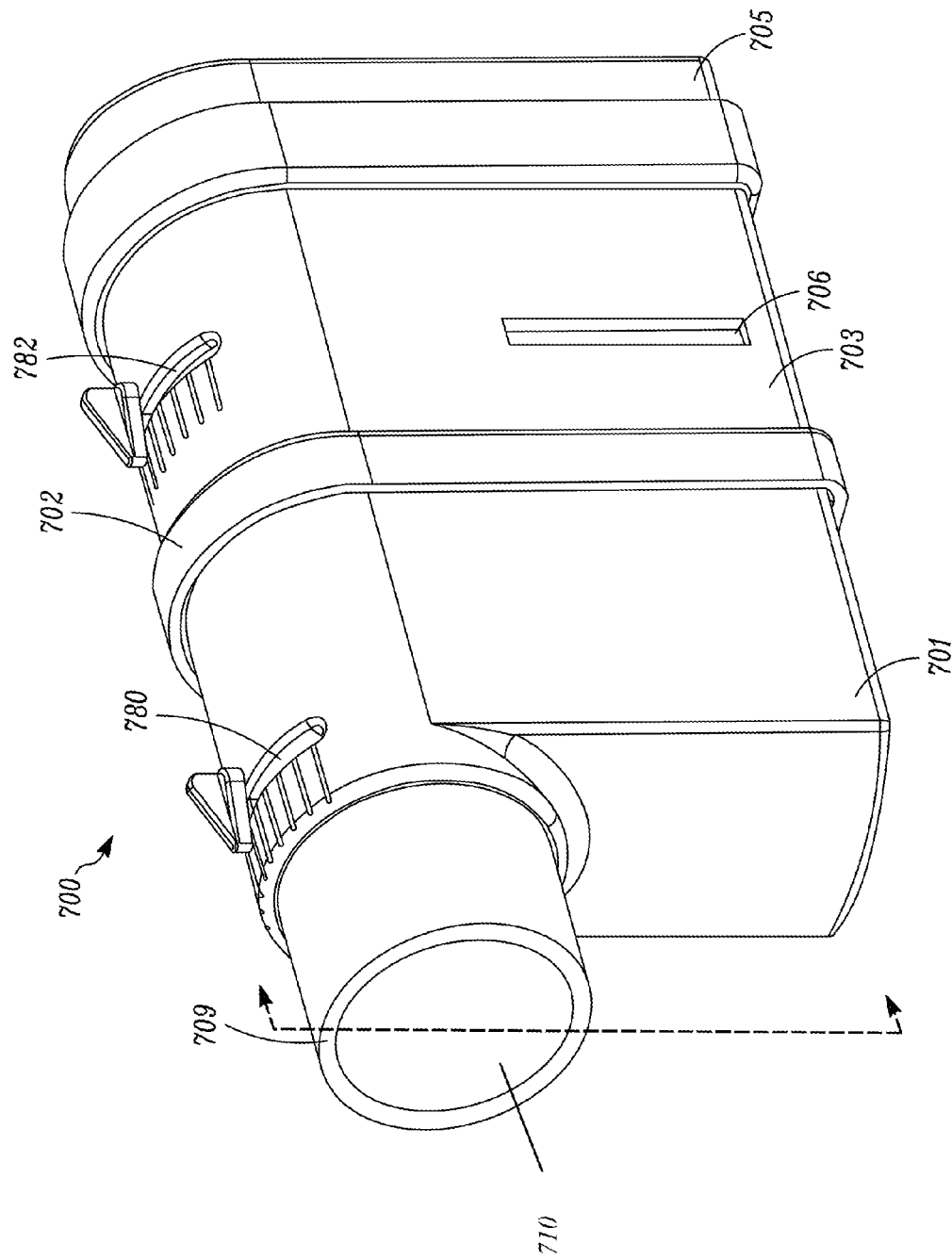
FIG. 46 is a front perspective view of yet another alternative embodiment of the OPEP device of FIG. 1.
Figure 47:
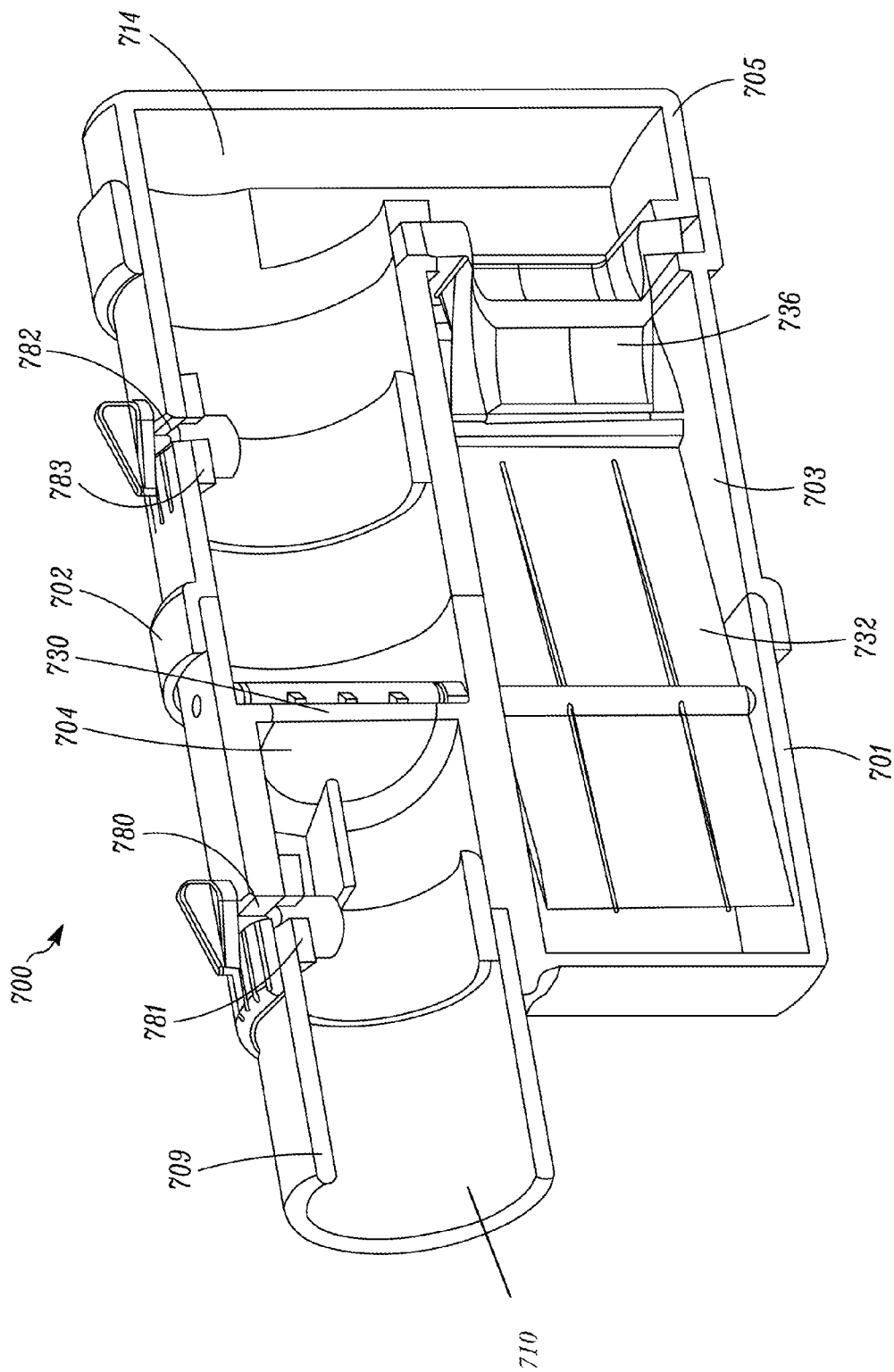
FIG. 47 is a cross-sectional view taken along line I in FIG. 46 of the OPEP device.

Turning to FIGS. 46-47, an OPEP device 700 is shown having a first aperture or control port 780 adapted to permit exhaled air to exit the respiratory treatment device 700 prior to entering a first chamber 714, and a second aperture or control port 782 adapted to permit exhaled air to exit the respiratory treatment device 700 from the first chamber 714. With the exception of the first control port 780 and the second control port 782, the OPEP device 700 is otherwise configured and operates the same as the OPEP device 100. As shown, the OPEP device 700 includes a housing 702 comprising a front section 701, a middle section 703, and a rear section 705. The housing is also associated with a mouthpiece 709 having a patient port 710, and includes a first chamber outlet 706 and a second chamber outlet (not shown) positioned opposite the first chamber outlet 706. As seen in the cross-sectional view of the FIG. 47, the OPEP device 700 includes a restrictor member 730 positioned relative to a chamber inlet 704 such that it is moveable between a closed position, where the flow of exhaled air through the chamber inlet 704 is restricted, and an open position, where the flow of exhaled air through the chamber inlet 704 is less restricted, as well as a variable nozzle 736, and a vane 732 operatively connected to the restrictor member 730 by a shaft (not shown).

Furthermore, both the first control port 780 and the second control port 782 may be equipped with regulation members 779, 783 configured to permit a user to selectively adjust the amount of exhaled air allowed to exit the respiratory treatment device 700 through either the first control port 780 or the second control port 782. For example, as shown in FIGS. 46-47, the regulation members 779, 783 are formed as a ring configured to rotate relative to the housing 702 to either increase or decrease the cross-sectional area of the control port 780, 782 through which exhaled air may flow. By selectively increasing the cross-sectional area of the first control port 780 through which exhaled air may flow, a user may decrease the amplitude and frequency of the OPEP therapy administered by the OPEP device 700, and vice-versa. By selectively increasing the cross-sectional area of the second control port 782, a user may decrease the frequency of the OPEP therapy administered by the OPEP device 700, and vice-versa. In this way, a user may selectively adjust the OPEP device 700 to maintain the ideal operating conditions.

Eighth Embodiment

Figure 48:
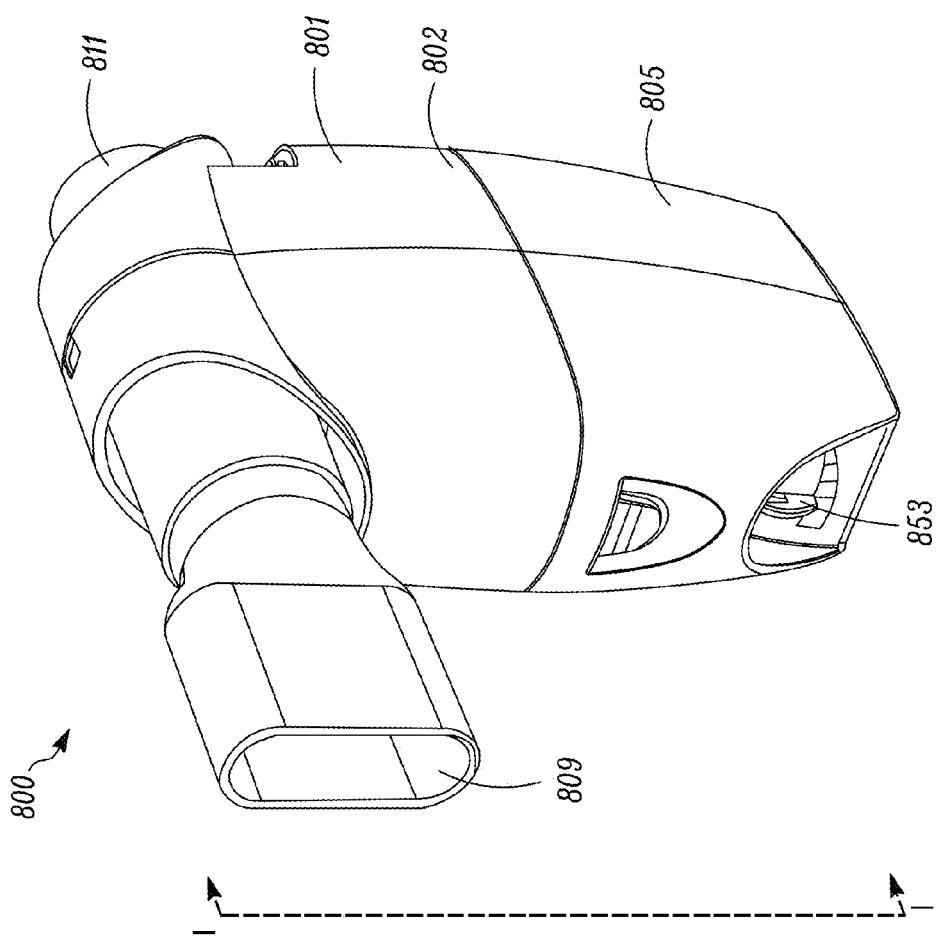
FIG. 48 is a front perspective view of another embodiment of an OPEP device.
Figure 49:
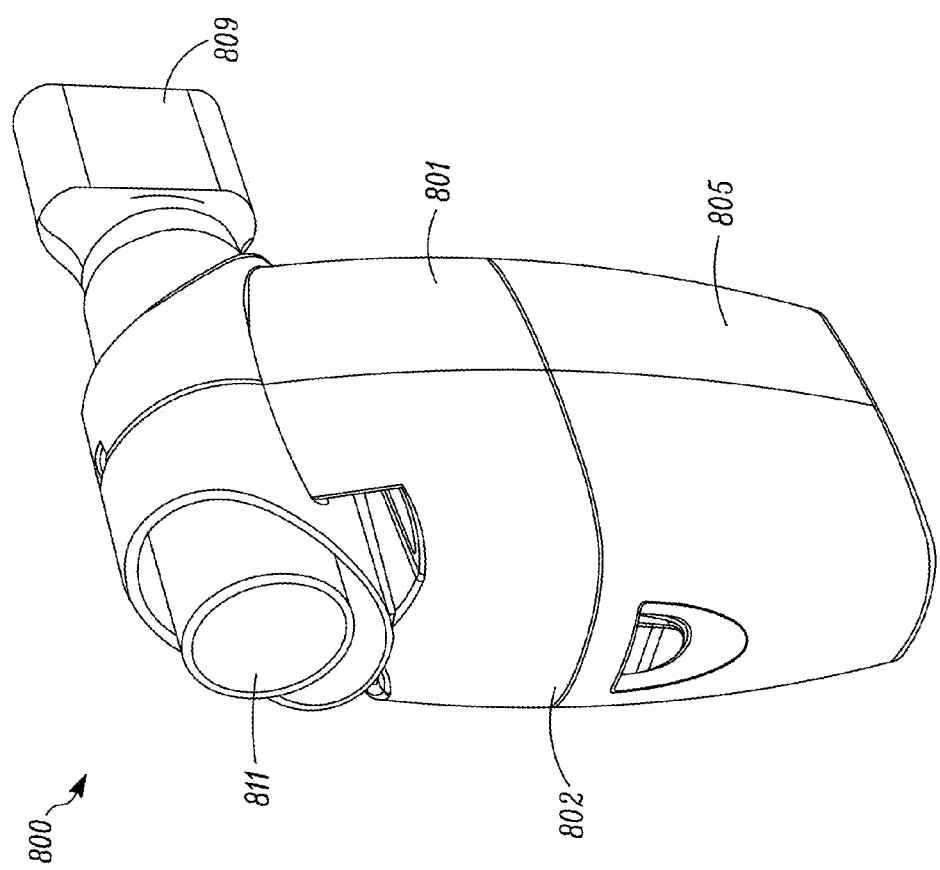
FIG. 49 is a rear perspective view of the OPEP device of FIG. 48.
Figure 50:
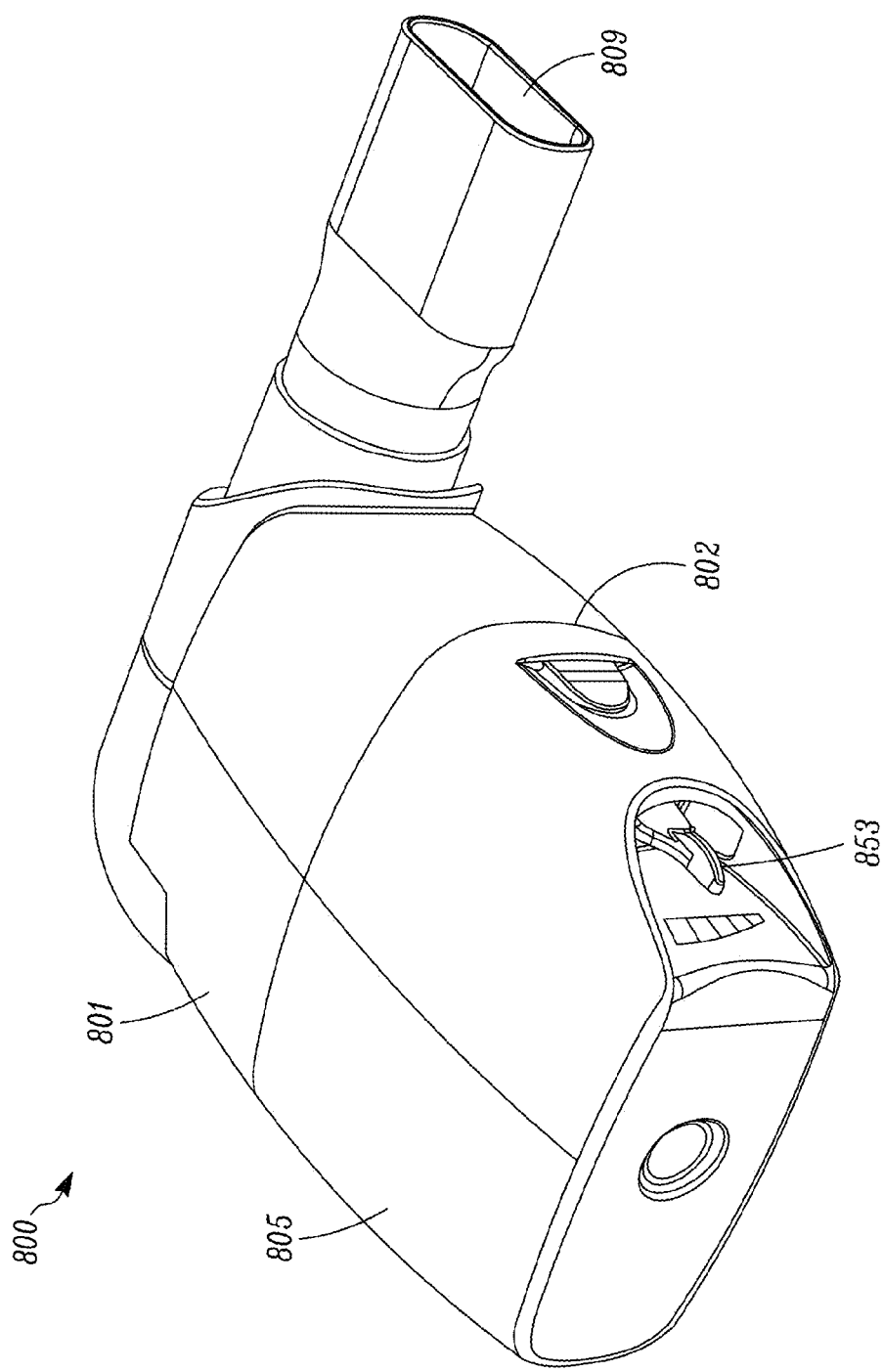
FIG. 50 is a perspective view of the bottom of the OPEP device of FIG. 48.

Turning to FIGS. 48-50, another embodiment of an OPEP device 800 is shown. The OPEP device 800 is similar to that of the OPEP device 200 in that is selectively adjustable. As best seen in FIGS. 48, 50, 53, and 62, the OPEP device 800, like the OPEP device 200, includes an adjustment mechanism 853 adapted to change the relative position of a chamber inlet 804 with respect to a housing 802 and a restrictor member 830, which in turn changes the range of rotation of a vane 832 operatively connected thereto. As previously explained with regards to the OPEP device 200, a user is therefore able to conveniently adjust both the frequency and the amplitude of the OPEP therapy administered by the OPEP device 800 without opening the housing 802 and disassembling the components of the OPEP device 800. The administration of OPEP therapy using the OPEP device 800 is otherwise the same as described above with regards to the OPEP device 100.

The OPEP device 800 comprises a housing 802 having a front section 801, a rear section 805, and an inner casing 803. As with the previously described OPEP devices, the front section 801, the rear section 805, and the inner casing 803 are separable so that the components contained therein can be periodically accessed, cleaned, or reconfigured, as required to maintain the ideal operating conditions. For example, as shown in FIGS. 48-50, the front section 801 and the rear section 805 of the housing 802 are removably connected via a snap fit engagement.

Figure 51:
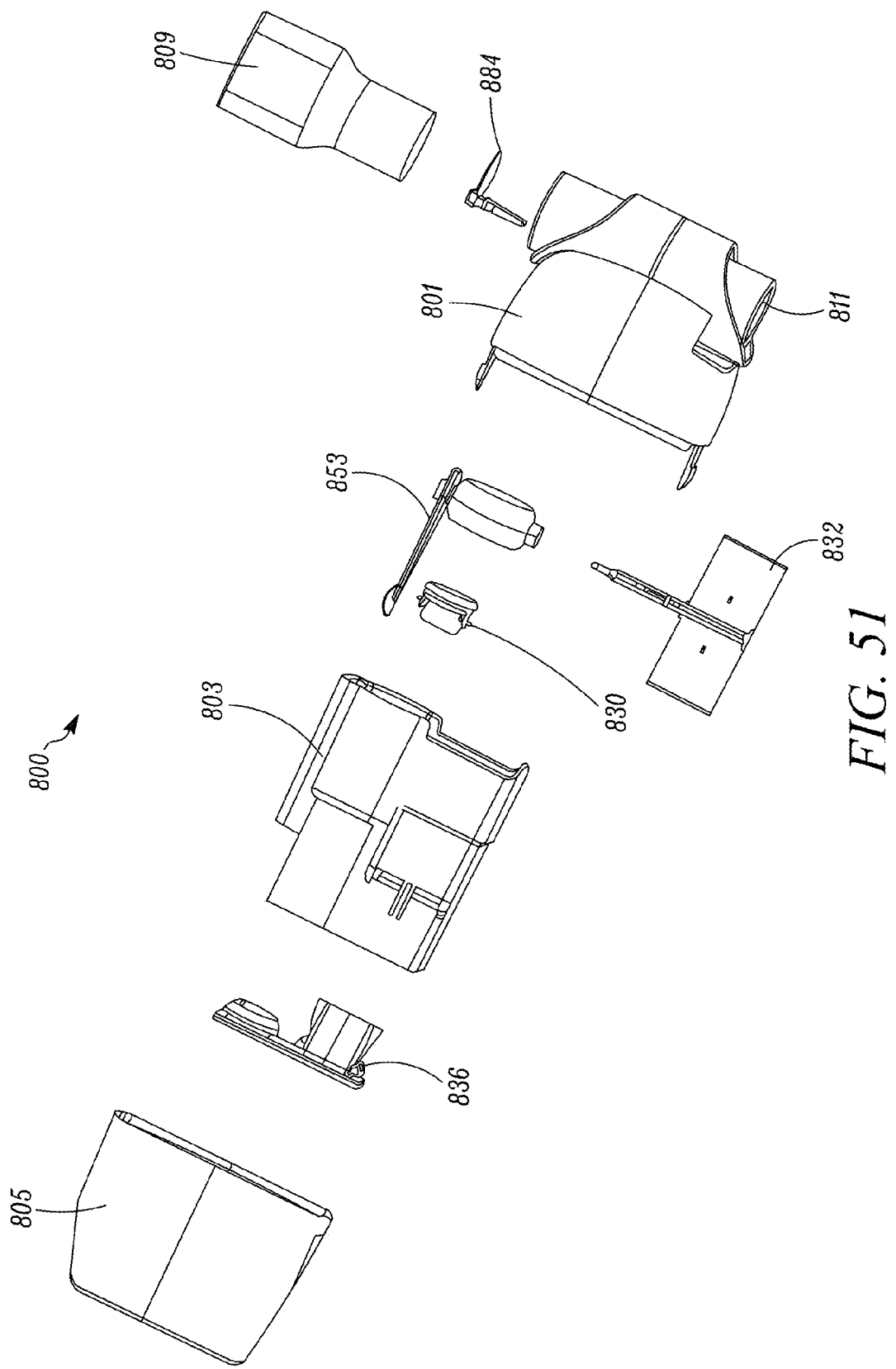
FIG. 51 is an exploded view of the OPEP device of FIG. 48.

The components of the OPEP device 800 are further illustrated in the exploded view of FIG. 51. In general, in addition to the front section 801, the rear section 805, and the inner casing 803, the OPEP device 800 further comprises a mouthpiece 809, an inhalation port 811, a one-way valve 884 disposed therebetween, an adjustment mechanism 853, a restrictor member 830, a vane 832, and a variable nozzle 836.

Figure 52:
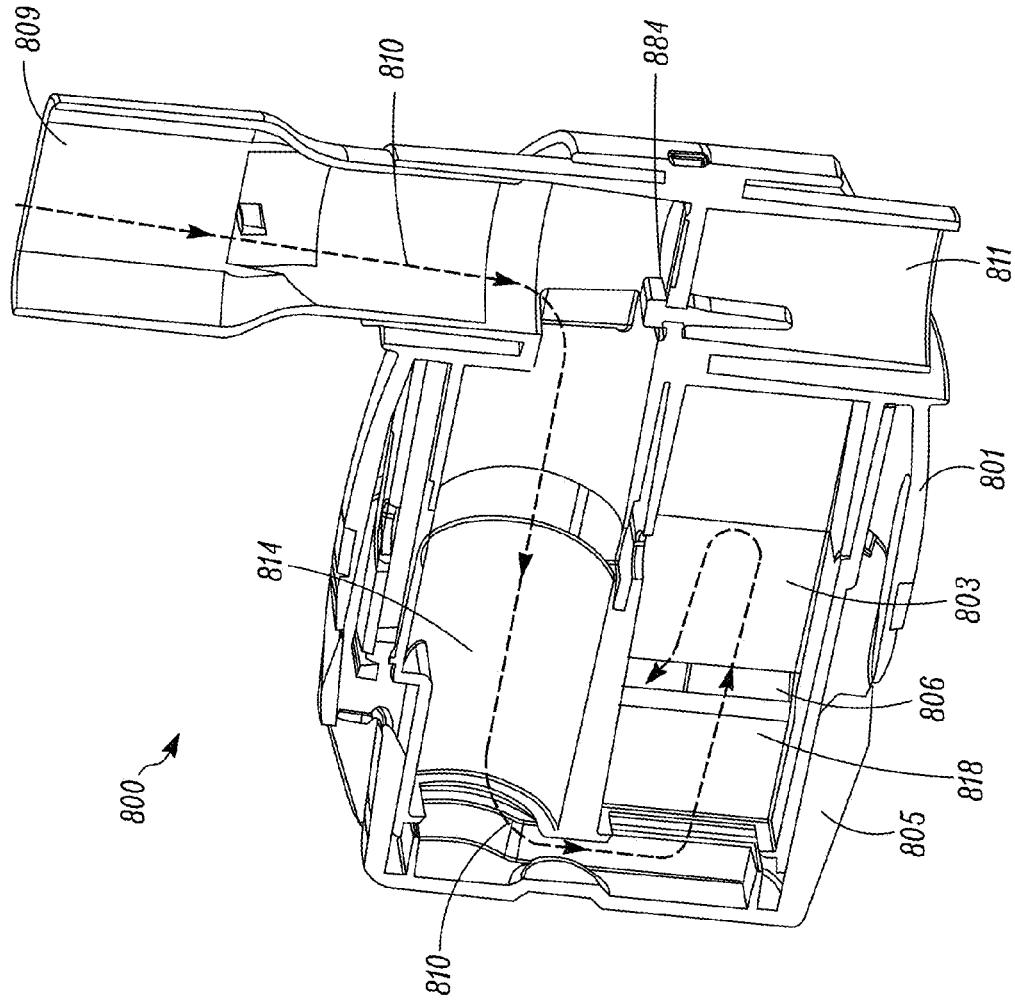
FIG. 52 is a cross-sectional view taken along line I in FIG. 48, shown without the internal components of the OPEP device.
Figure 53:
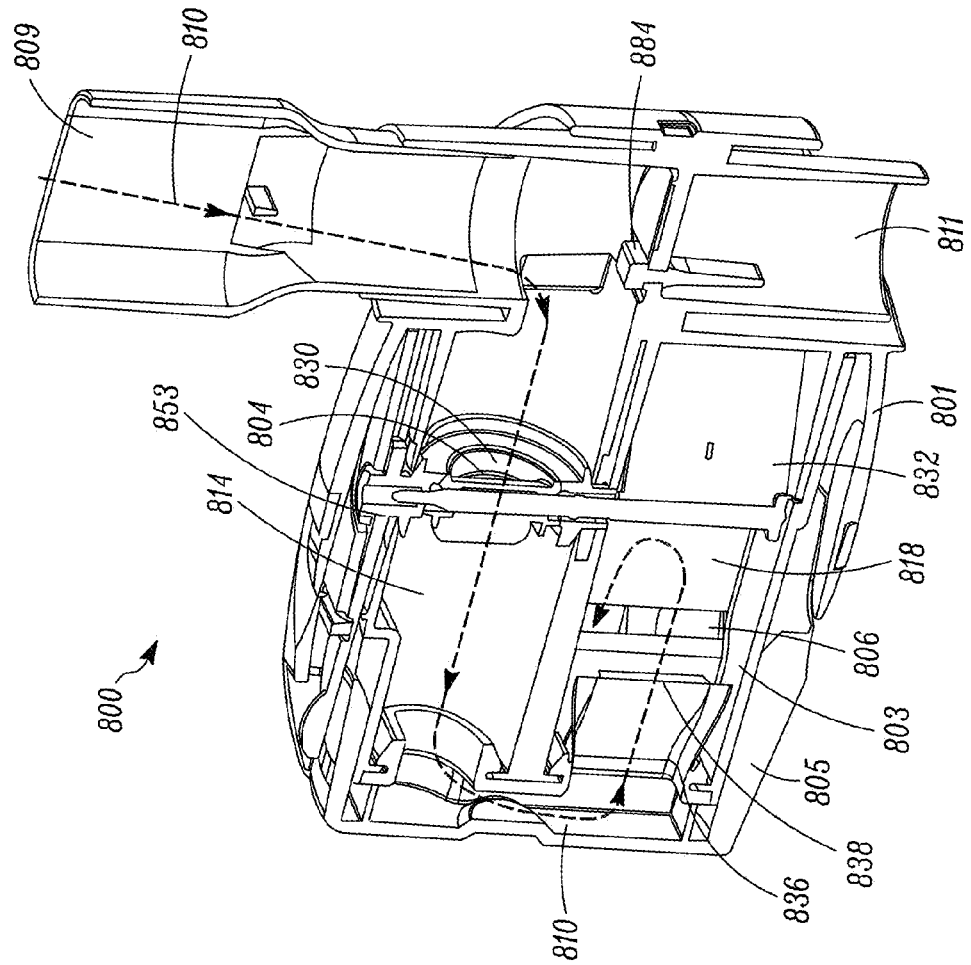
FIG. 53 is a cross-sectional view taken along line I in FIG. 48, shown with the internal components of the OPEP device.
Figure 54:
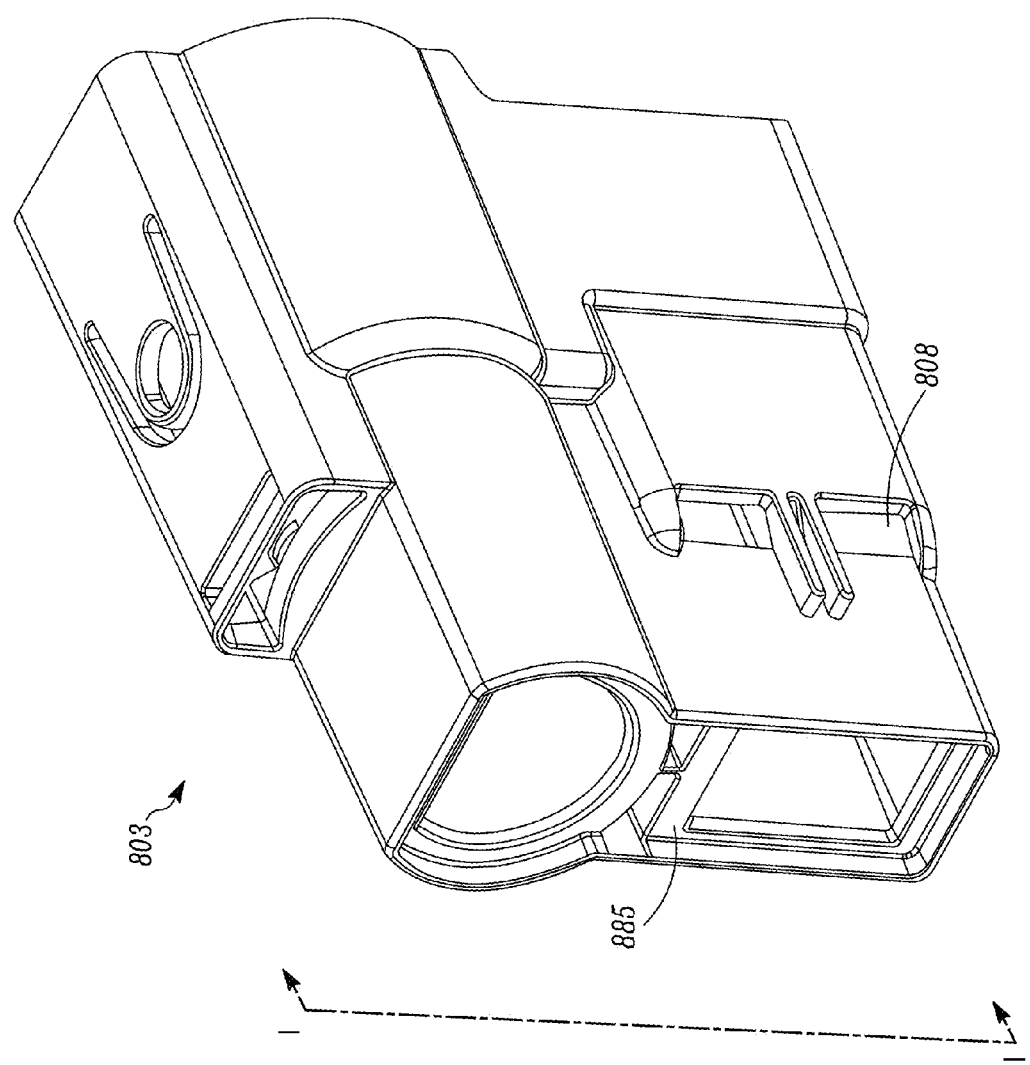
FIG. 54 is a front-perspective view of an inner casing of the OPEP device of FIG. 48.
Figure 55:
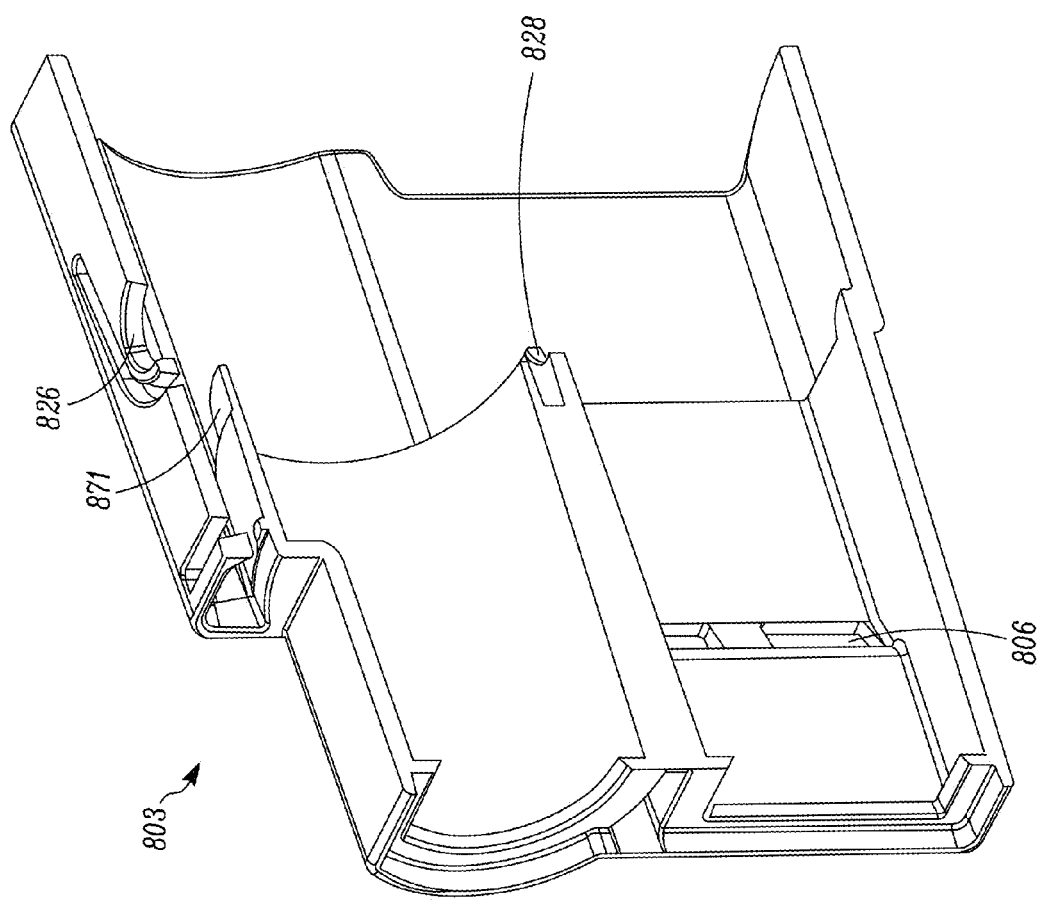
FIG. 55 is a cross-sectional view of the inner casing taken along line I of in FIG. 54.

As seen in FIGS. 52-53, the inner casing 803 is configured to fit within the housing 802 between the front section 801 and the rear section 805, and partially defines a first chamber 814 and a second chamber 818. The inner casing 803 is shown in further detail in the perspective and cross sectional views shown in FIGS. 54-55. A first chamber outlet 806 and a second chamber outlet 808 are formed within the inner casing 803. One end 885 of the inner casing 803 is adapted to receive the variable nozzle 836 and maintain the variable nozzle 836 between the rear section 805 and the inner casing 803. An upper bearing 826 and a lower bearing 828 for supporting the adjustment mechanism 853 is formed, at least in part, within the inner casing 803. Like the flexible cylinder 271 and sealing edge 270 described above with regards to the OPEP device 200, the inner casing 803 also includes a flexible cylinder 871 with a sealing edge 870 for engagement about a frame 856 of the adjustment mechanism 853.

Figure 56:
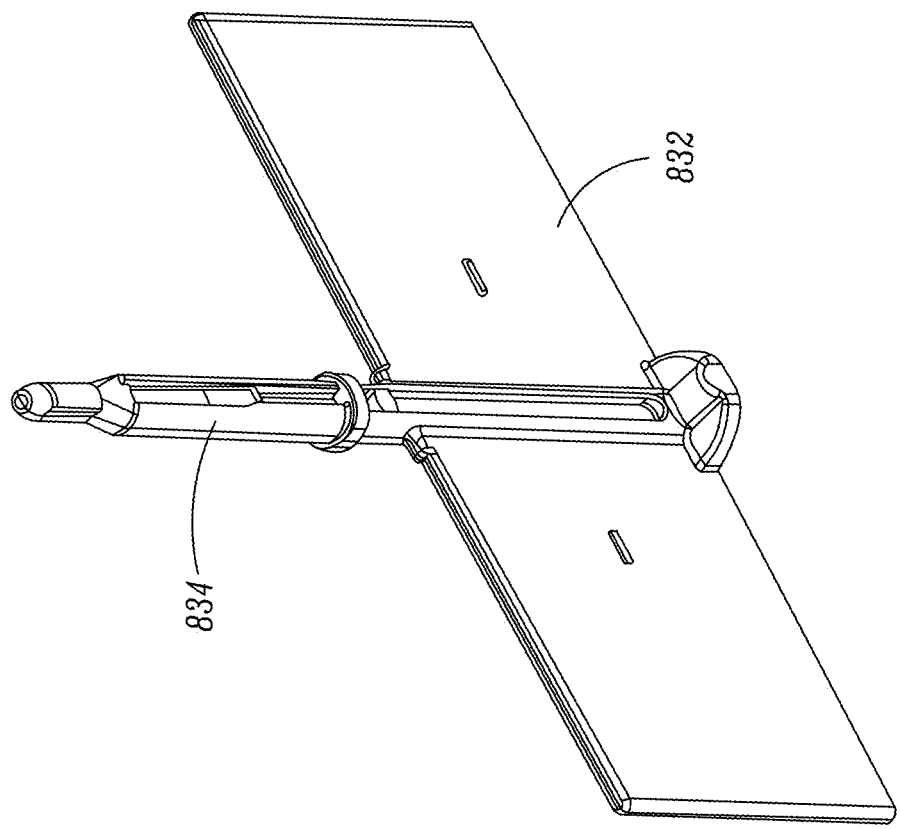
FIG. 56 is a perspective view of a vane of the OPEP device of FIG. 48.

The vane 832 is shown in further detail in the perspective view shown in FIG. 56. A shaft 834 extends from the vane 832 and is keyed to engage a corresponding keyed portion within a bore 865 of the restrictor member 830. In this way, the shaft 834 operatively connects the vane 832 with the restrictor member 830 such that the vane 832 and the restrictor member 830 rotate in unison.

Figure 57:
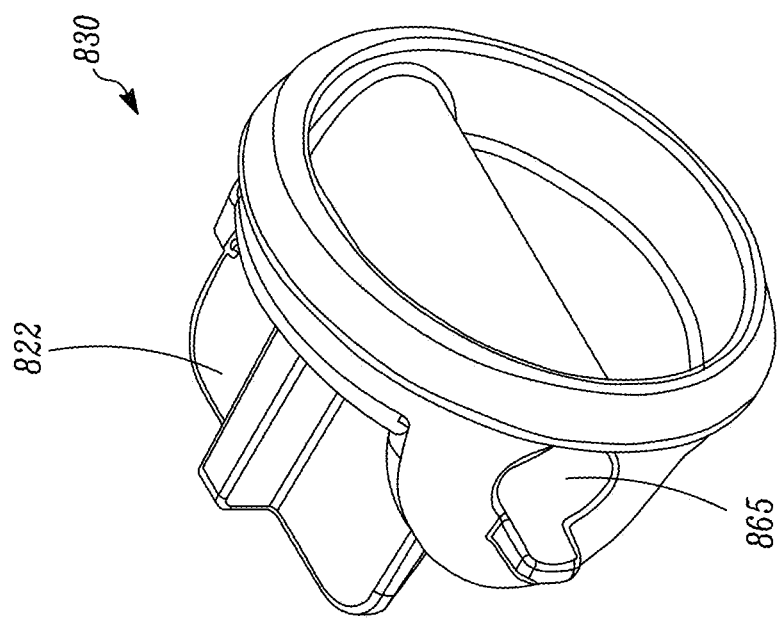
FIG. 57 is a front perspective view of a restrictor member of the OPEP device of FIG. 48.
Figure 59:
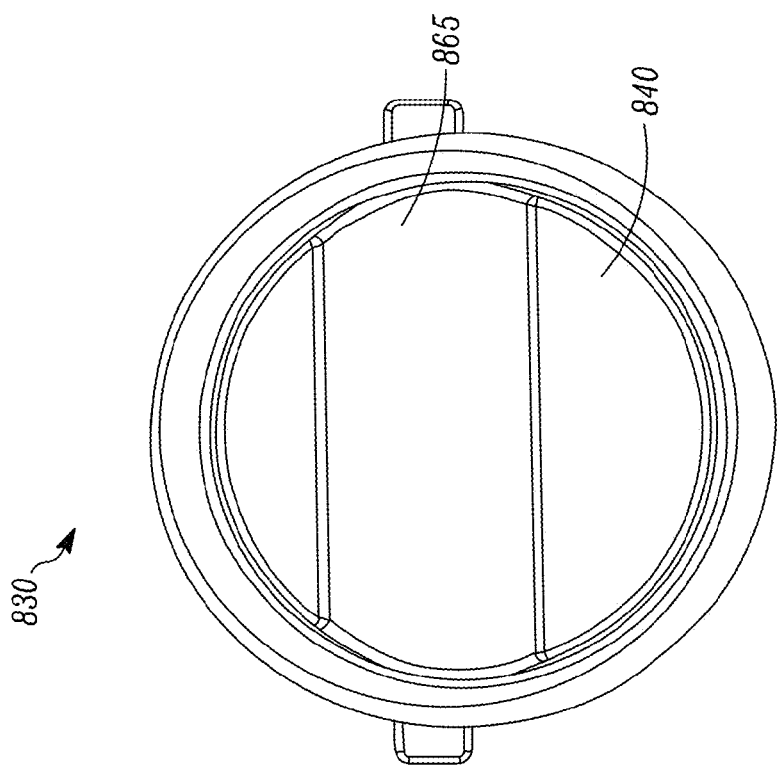
FIG. 59 is a front view of the restrictor member of FIG. 57.
Figure 58:
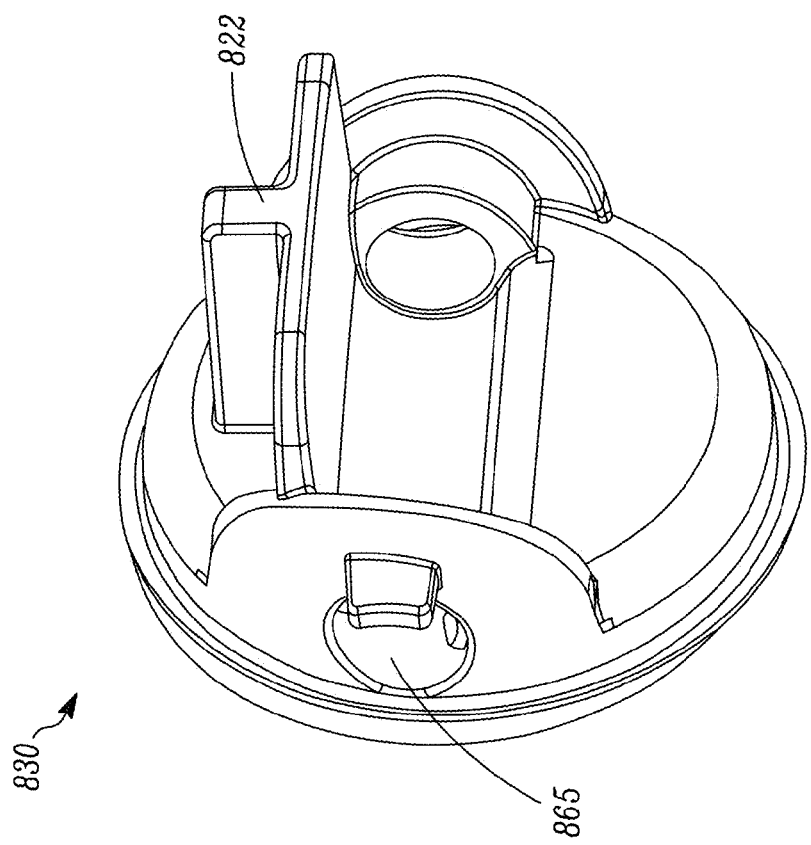
FIG. 58 is a rear perspective view of the restrictor member of the FIG. 57.

The restrictor member 830 is shown in further detail in the perspective views shown in FIGS. 57-58. The restrictor member 830 includes a keyed bore 865 for receiving the shaft 834 extending from the vane 832, and further includes a stop 822 that limits permissible rotation of the restrictor member 830 relative to a seat 824 of the adjustment member 853. As shown in the front view of FIG. 59, like the restrictor member 130, the restrictor member 830 further comprises an offset designed to facilitate movement of the restrictor member 830 between a closed position and an open position. More specifically, a greater surface area of the face 840 of the restrictor member 830 is positioned on one side of the bore 865 for receiving the shaft 834 than on the other side of the bore 865. As described above with regards to the restrictor member 130, this offset produces an opening torque about the shaft 834 during periods of exhalation.

Figure 60:
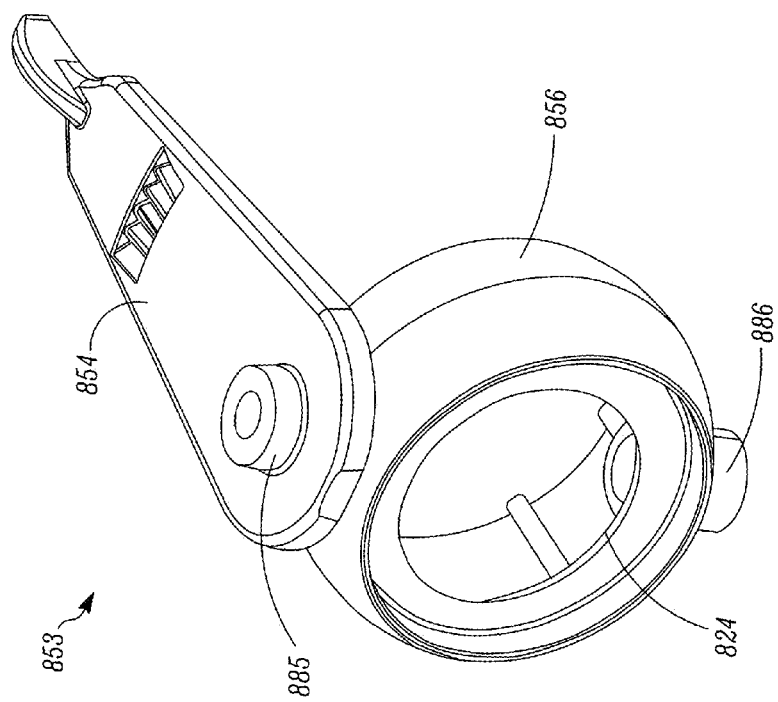
FIG. 60 is a front perspective view of an adjustment mechanism of the OPEP device of FIG. 48.
Figure 61:
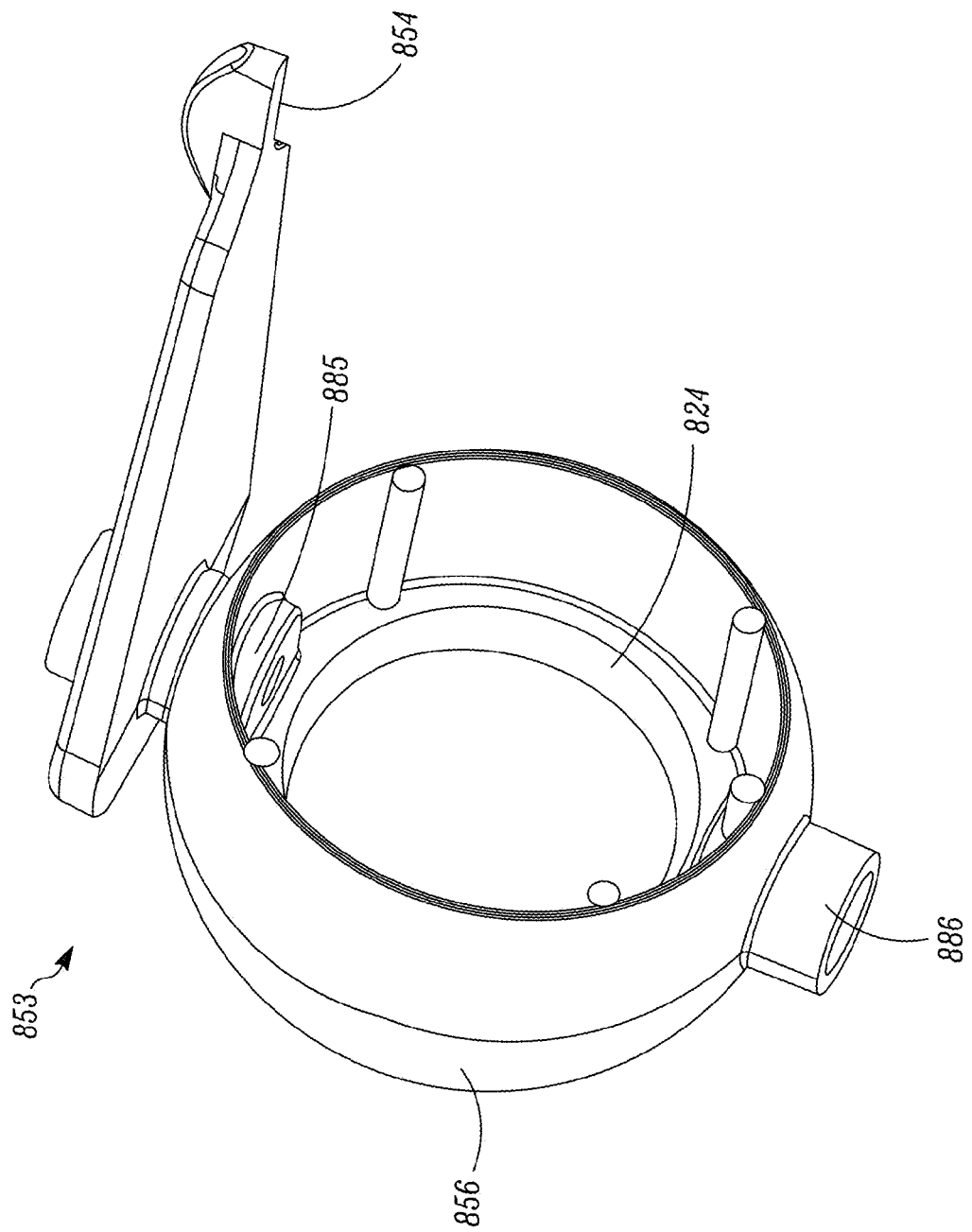
FIG. 61 is a rear perspective view of the adjustment mechanism of FIG. 60.

The adjustment mechanism 853 is shown in further detail in the front and rear perspective views of FIGS. 60 and 61. In general, the adjustment mechanism includes a frame 856 adapted to engage the sealing edge 870 of the flexible cylinder 871 formed on the inner casing 803. A circular opening in the frame 856 forms a seat 824 shaped to accommodate the restrictor member 830. In this embodiment, the seat 824 also defines the chamber inlet 804. The adjustment mechanism 853 further includes an arm 854 configured to extend from the frame 856 to a position beyond the housing 802 in order to permit a user to selectively adjust the orientation of the adjustment mechanism 853, and therefore the chamber inlet 804, when the OPEP device 800 is fully assembled. The adjustment mechanism 853 also includes an upper bearing 885 and a lower bearing 886 for receiving the shaft 834.

Figure 62:
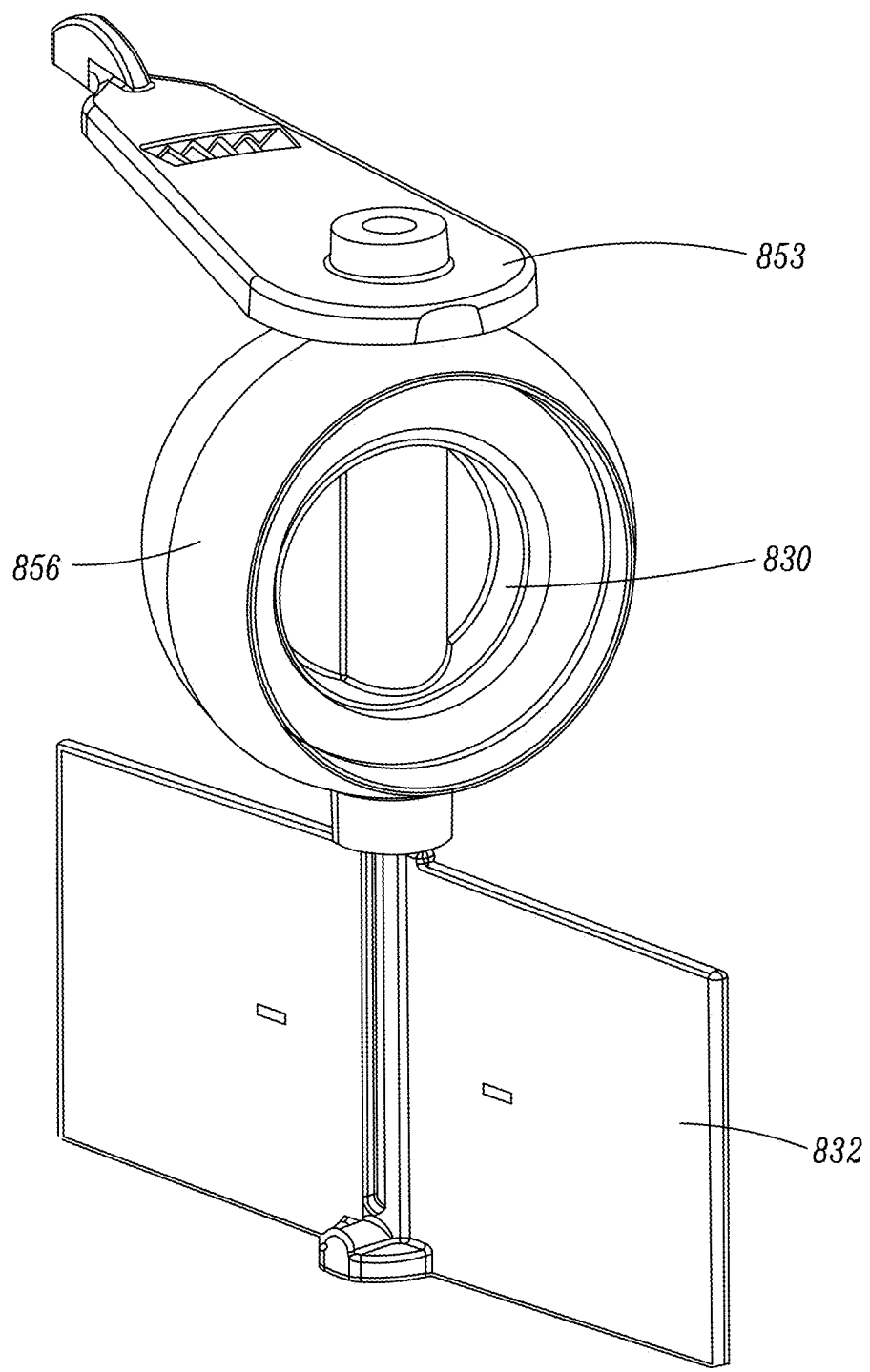
FIG. 62 is a front perspective view of the adjustment mechanism of FIGS. 60-61 assembled with the restrictor member of FIGS. 57-59 and the vane of FIG. 56.

An assembly of the vane 832, the adjustment mechanism 853, and the restrictor member 830 is shown in the perspective view of FIG. 62. As previously explained, the vane 832 and the restrictor member 830 are operatively connected by the shaft 834 such that rotation of the vane 832 results in rotation of the restrictor member 830, and vice versa. In contrast, the adjustment mechanism 853, and therefore the seat 824 defining the chamber inlet 804, is configured to rotate relative to the vane 832 and the restrictor member 830 about the shaft 834. In this way, a user is able to rotate the arm 854 to selectively adjust the orientation of the chamber inlet 804 relative to the restrictor member 830 and the housing 802. For example, a user may increase the frequency and amplitude of the OPEP therapy administered by the OPEP device 800 by rotating the arm 854, and therefore the frame 856, in a clockwise direction. Alternatively, a user may decrease the frequency and amplitude of the OPEP therapy administered by the OPEP device 800 by rotating the adjustment arm 854, and therefore the frame 256, in a counter-clockwise direction. Furthermore, as shown for example in FIGS. 48 and 50, indicia may be provided on the housing 802 to aid the user in the setting of the appropriate configuration of the OPEP device 800.

Figure 64:
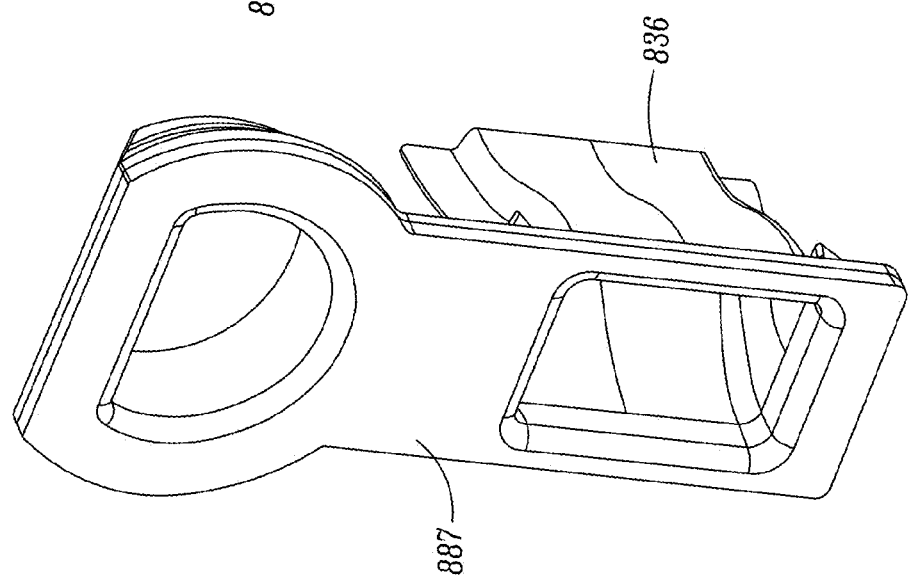
FIG. 64 is a rear perspective view of the variable nozzle of FIG. 63.
Figure 63:
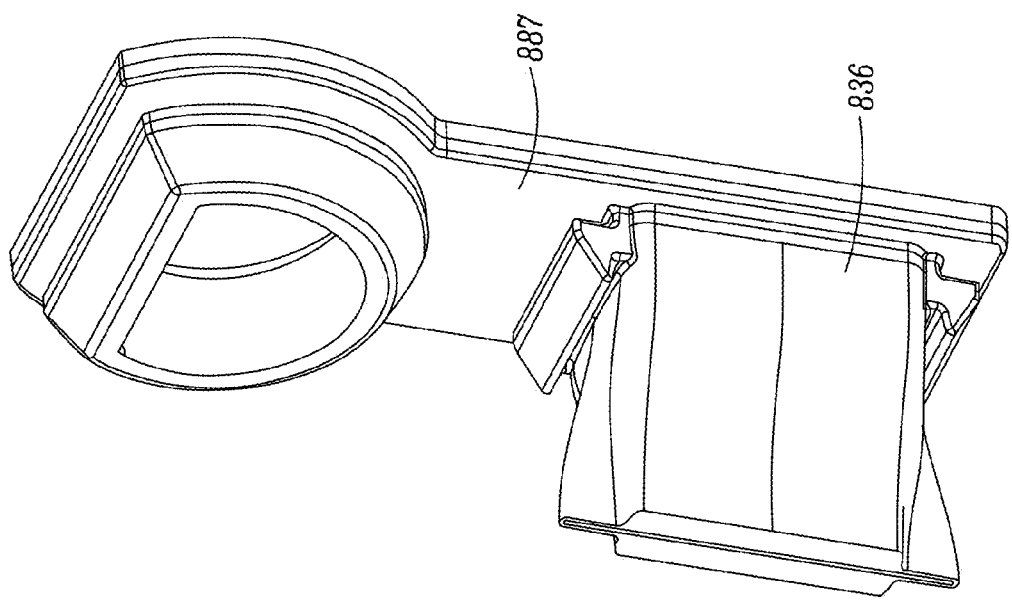
FIG. 63 is a front perspective view of a variable nozzle of the OPEP device of FIG. 48.

The variable nozzle 836 is shown in further detail in the front and rear perspective views of FIGS. 63 and 64. The variable nozzle 836 in the OPEP device 800 is similar to the variable nozzle 236 described above with regards to the OPEP device 200, except that the variable nozzle 836 also includes a base plate 887 configured to fit within one end 885 (see FIGS. 54-55) of the inner casing 803 and maintain the variable nozzle 836 between the rear section 805 and the inner casing 803. Like the variable nozzle 236, the variable nozzle 836 and base plate 887 may be made of silicone.

Figure 65:
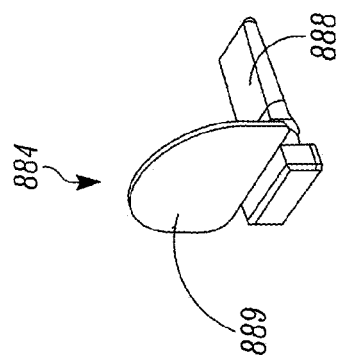
FIG. 65 is a front perspective view of the one-way valve of the OPEP device of FIG. 48.

The one-way valve 884 is shown in further detail in the front perspective view of FIG. 65. In general, the one-way valve 884 comprises a post 888 adapted for mounting in the front section 801 of the housing 802, and a flap 889 adapted to bend or pivot relative to the post 888 in response to a force or a pressure on the flap 889. Those skilled in the art will appreciate that other one-way valves may be used in this and other embodiments described herein without departing from the teachings of the present disclosure. As seen in FIGS. 52-53, the one-way valve 884 may be positioned in the housing 802 between the mouthpiece 809 and the inhalation port 811.

As discussed above in relation to the OPEP device 100, the OPEP device 800 may be adapted for use with other or additional interfaces, such as an aerosol delivery device. In this regard, the OPEP device 800 is equipped with an inhalation port 811 (best seen in FIGS. 48-49 and 51-53) in fluid communication with the mouthpiece 809. As noted above, the inhalation port may include a separate one-way valve 884 (best seen in FIGS. 52-53 and 65) configured to permit a user of the OPEP device 800 both to inhale the surrounding air through the one-way valve 884 and to exhale through the chamber inlet 804, without withdrawing the mouthpiece 809 of the OPEP device 800 between periods of inhalation and exhalation. In addition, the aforementioned commercially available aerosol delivery devices may be connected to the inhalation port 811 for the simultaneous administration of aerosol therapy (upon inhalation) and OPEP therapy (upon exhalation).

The OPEP device 800 and the components described above are further illustrated in the cross-sectional views shown in FIGS. 52-53. For purposes of illustration, the cross-sectional view of FIG. 52 is shown without all the internal components of the OPEP device 800.

The front section 801, the rear section 805, and the inner casing 803 are assembled to form a first chamber 814 and a second chamber 818. As with the OPEP device 100, an exhalation flow path 810, identified by a dashed line, is defined between the mouthpiece 809 and at least one of the first chamber outlet 806 (best seen in FIGS. 52-53 and 55) and the second chamber outlet 808 (best seen in FIG. 54), both of which are formed within the inner casing 803. As a result of the inhalation port 811 and the one-way valve 848, the exhalation flow path 810 begins at the mouthpiece 809 and is directed toward the chamber inlet 804, which in operation may or may not be blocked by the restrictor member 830. After passing through the chamber inlet 804, the exhalation flow path 810 enters the first chamber 814 and makes a 180° turn toward the variable nozzle 836. After passing through an orifice 838 of the variable nozzle 836, the exhalation flow path 810 enters the second chamber 818. In the second chamber 818, the exhalation flow path 810 may exit the second chamber 818, and ultimately the housing 802, through at least one of the first chamber outlet 806 or the second chamber outlet 808. Those skilled in the art will appreciate that the exhalation flow path 810 identified by the dashed line is exemplary, and that air exhaled into the OPEP device 800 may flow in any number of directions or paths as it traverses from the mouthpiece 809 or chamber inlet 804 to the first chamber outlet 806 or the second chamber outlet 808. As previously noted, the administration of OPEP therapy using the OPEP device 800 is otherwise the same as described above with regards to the OPEP device 100.

Solely by way of example, the follow operating conditions, or performance characteristics, may be achieved by an OPEP device according to the OPEP device 800, with the adjustment dial 854 set for increased frequency and amplitude:

| Flow Rate (lpm) | 10 | 30 |
| Frequency (Hz) | 7 | 20 |
| Upper Pressure (cm H2O) | 13 | 30 |
| Lower Pressure (cm H2O) | 1.5 | 9 |
| Amplitude (cm H2O) | 11.5 | 21 |

The frequency and amplitude may decrease, for example, by approximately 20% with the adjustment dial 854 set for decreased frequency and amplitude. Other frequency and amplitude targets may be achieved by varying the particular configuration or sizing of elements, for example, increasing the length of the vane 832 results in a slower frequency, whereas, decreasing the size of the orifice 838 results in a higher frequency. The above example is merely one possible set of operating conditions for an OPEP device according to the embodiment described above.

Ninth Embodiment

Turning to FIGS. 66-69, another embodiment of a respiratory treatment device 900 is shown. Unlike the previously described OPEP devices, the respiratory treatment device 900 is configured to administer oscillating pressure therapy upon both exhalation and inhalation. Those skilled in the art will appreciated that the concepts described below with regards to the respiratory treatment device 900 may be applied to any of the previously described OPEP devices, such that oscillating pressure therapy may be administered upon both exhalation and inhalation. Likewise, the respiratory treatment device 900 may incorporate any of the concepts above regarding the previously described OPEP devices, including for example, a variable nozzle, an inhalation port adapted for use with an aerosol delivery device for the administration of aerosol therapy, an adjustment mechanism, a chamber inlet bypass, one or more control ports, etc.

Figure 66:
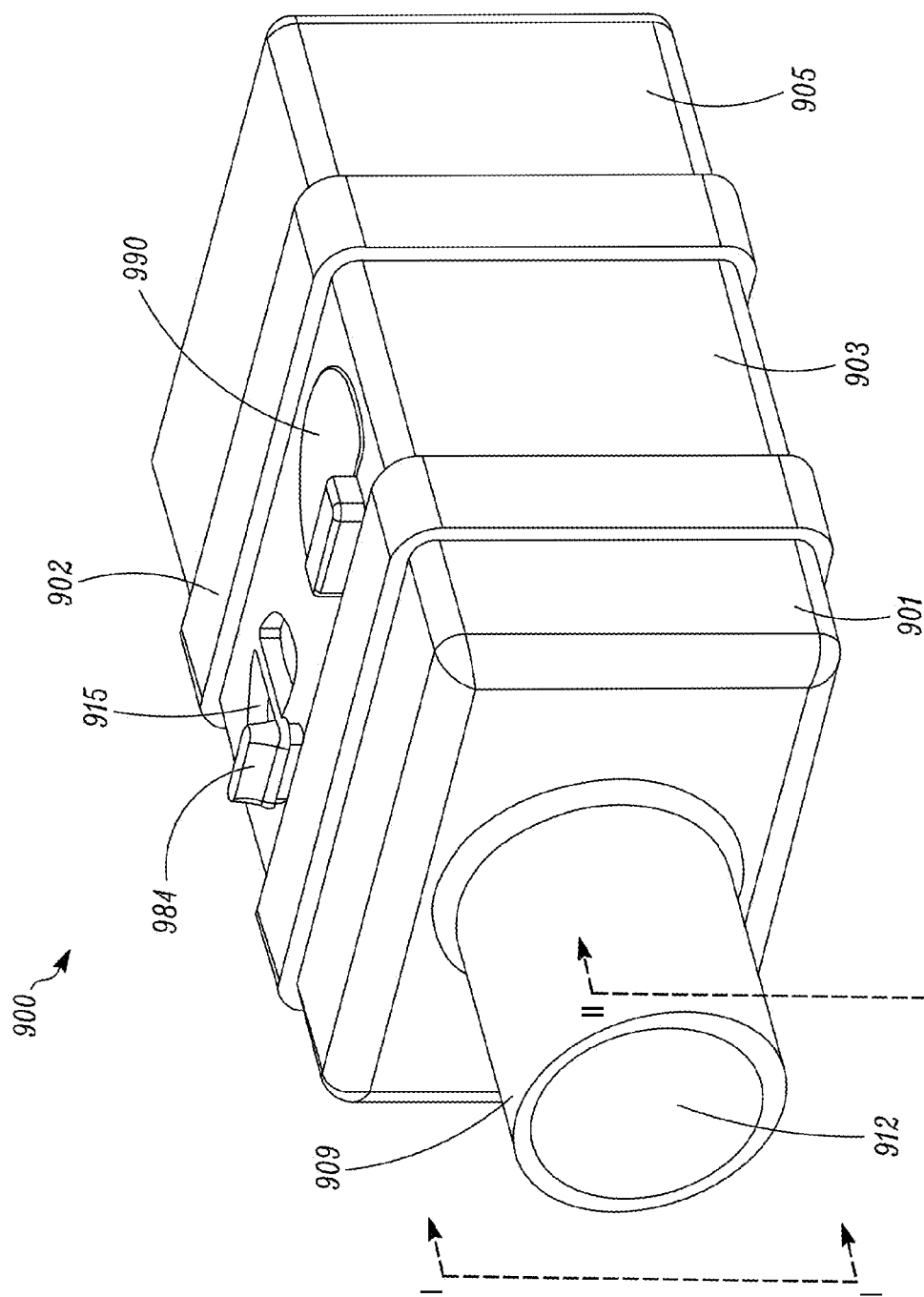
FIG. 66 is a perspective view of another embodiment of a respiratory treatment device.
Figure 67:
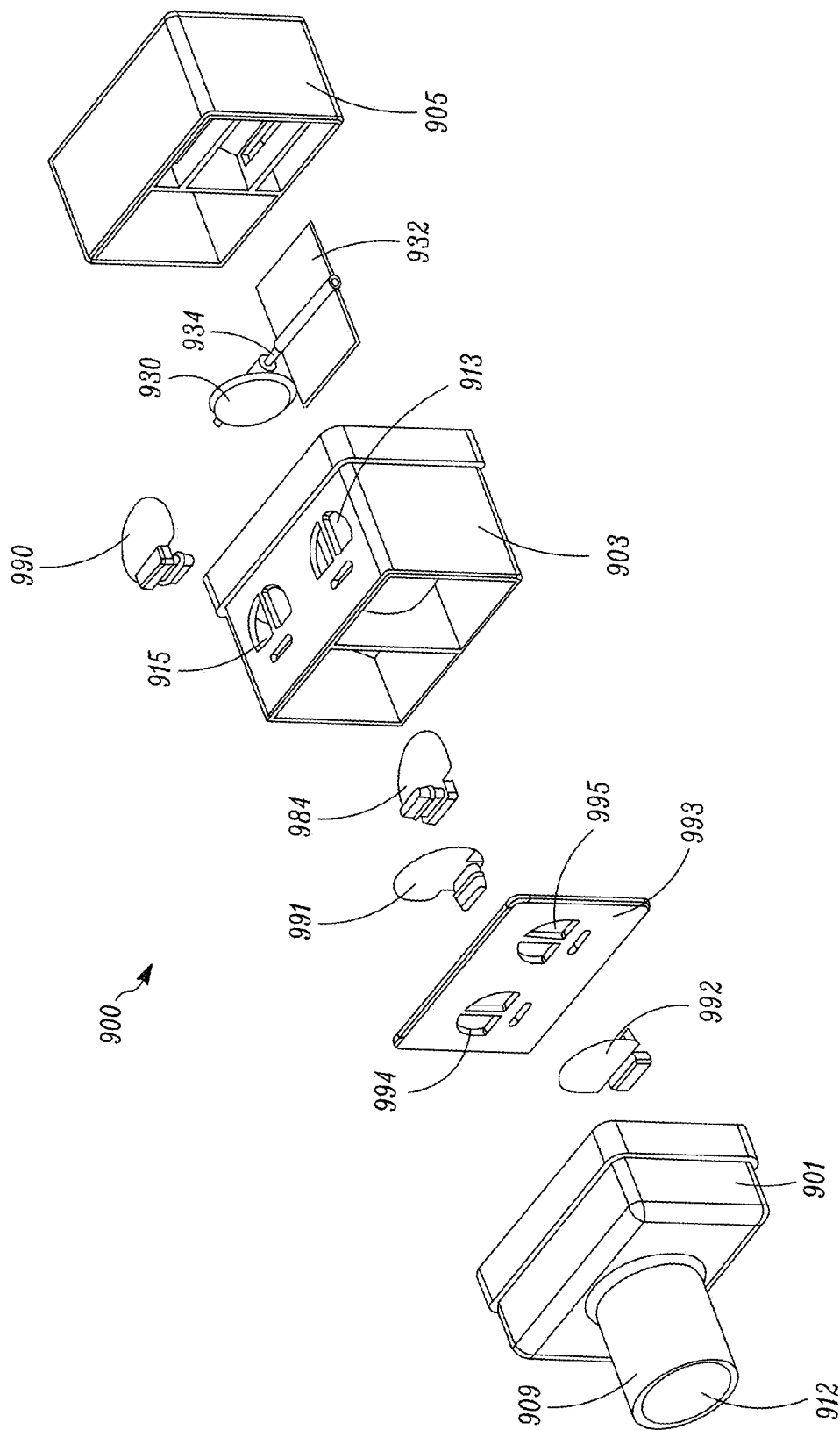
FIG. 67 is an exploded view of the respiratory treatment device of FIG. 66.

As shown in FIGS. 66 and 67, the respiratory treatment device 900 includes a housing 902 having a front section 901, a middle section 903, and a rear section 905. As with the OPEP devices described above, the housing 902 is openable so that the contents of the housing 902 may be accessed for cleaning and/or selective replacement of the components contained therein to maintain ideal operating conditions. The housing 902 further includes a first opening 912, a second opening 913, and a third opening 915.

Although the first opening 912 is shown in FIGS. 66 and 67 in association with a mouthpiece 909, the first opening 912 may alternatively be associated with other user interfaces, for example, a gas mask or a breathing tube. The second opening 913 includes a one-way exhalation valve 990 configured to permit air exhaled into the housing 902 to exit the housing 902 upon exhalation at the first opening 912. The third opening 915 includes a one-way inhalation valve 984 configured to permit air outside the housing 902 to enter the housing 902 upon inhalation at the first opening 912. As shown in greater detail in FIG. 67, the respiratory treatment device 900 further includes a manifold plate 993 having an exhalation passage 994 and an inhalation passage 995. A one-way valve 991 is adapted to mount to within the manifold plate 993 adjacent to the exhalation passage 994 such that the one-way valve 991 opens in response to air exhaled into the first opening 912, and closes in response to air inhaled through the first opening 912. A separate one-way valve 992 is adapted to mount within the manifold pate 993 adjacent to the inhalation passage 995 such that the one-way valve 992 closes in response to air exhaled into the first opening 912, and opens in response to air inhaled through the first opening 912. The respiratory treatment device 900 also includes a restrictor member 930 and a vane 932 operatively connected by a shaft 934, the assembly of which may operate in the same manner as described above with regards to the disclosed OPEP devices.

Figure 68:
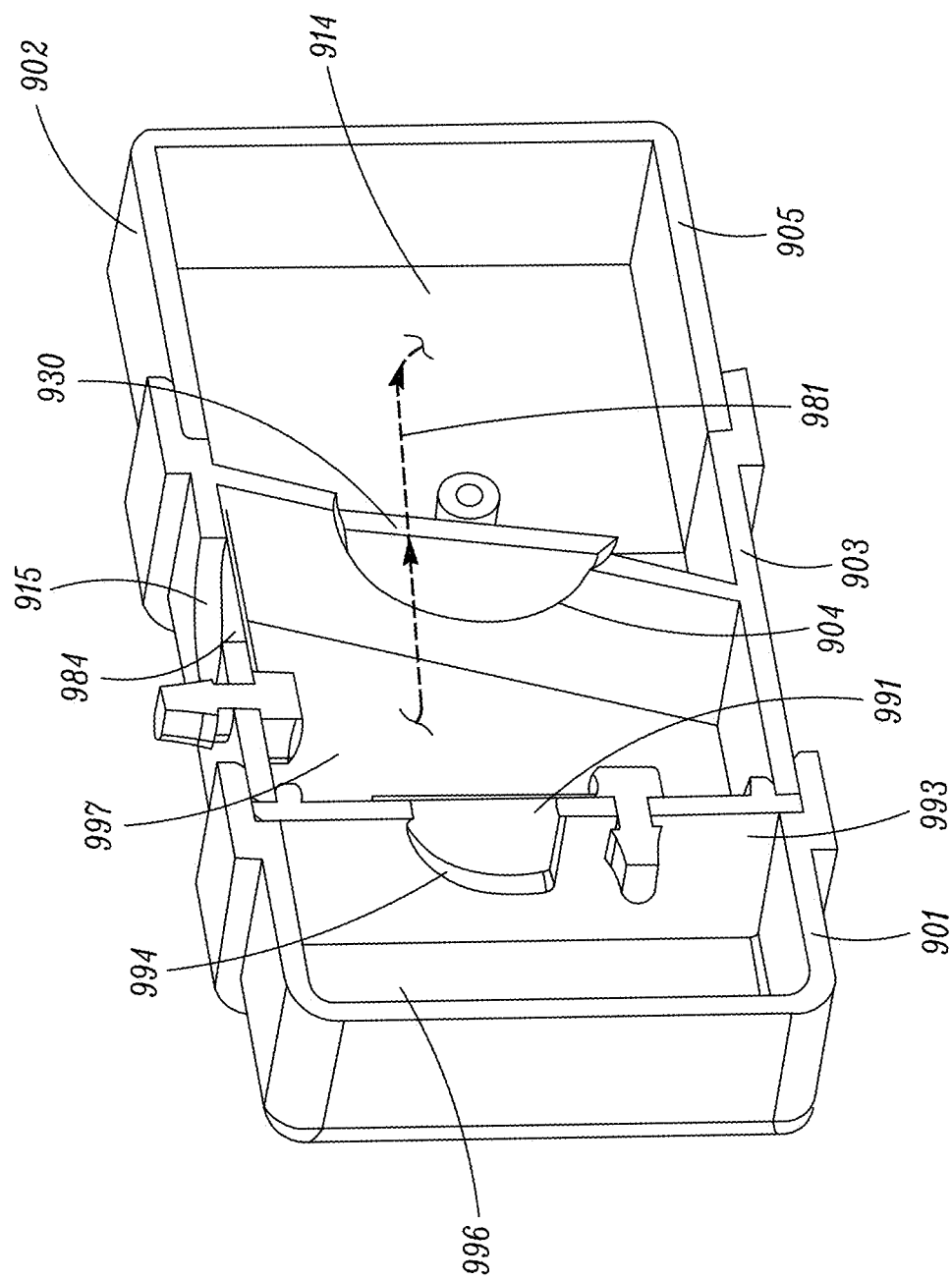
FIG. 68 is a cross-sectional perspective view taken along line I in FIG. 66 of the respiratory treatment device shown with the internal components of the device.
Figure 69:
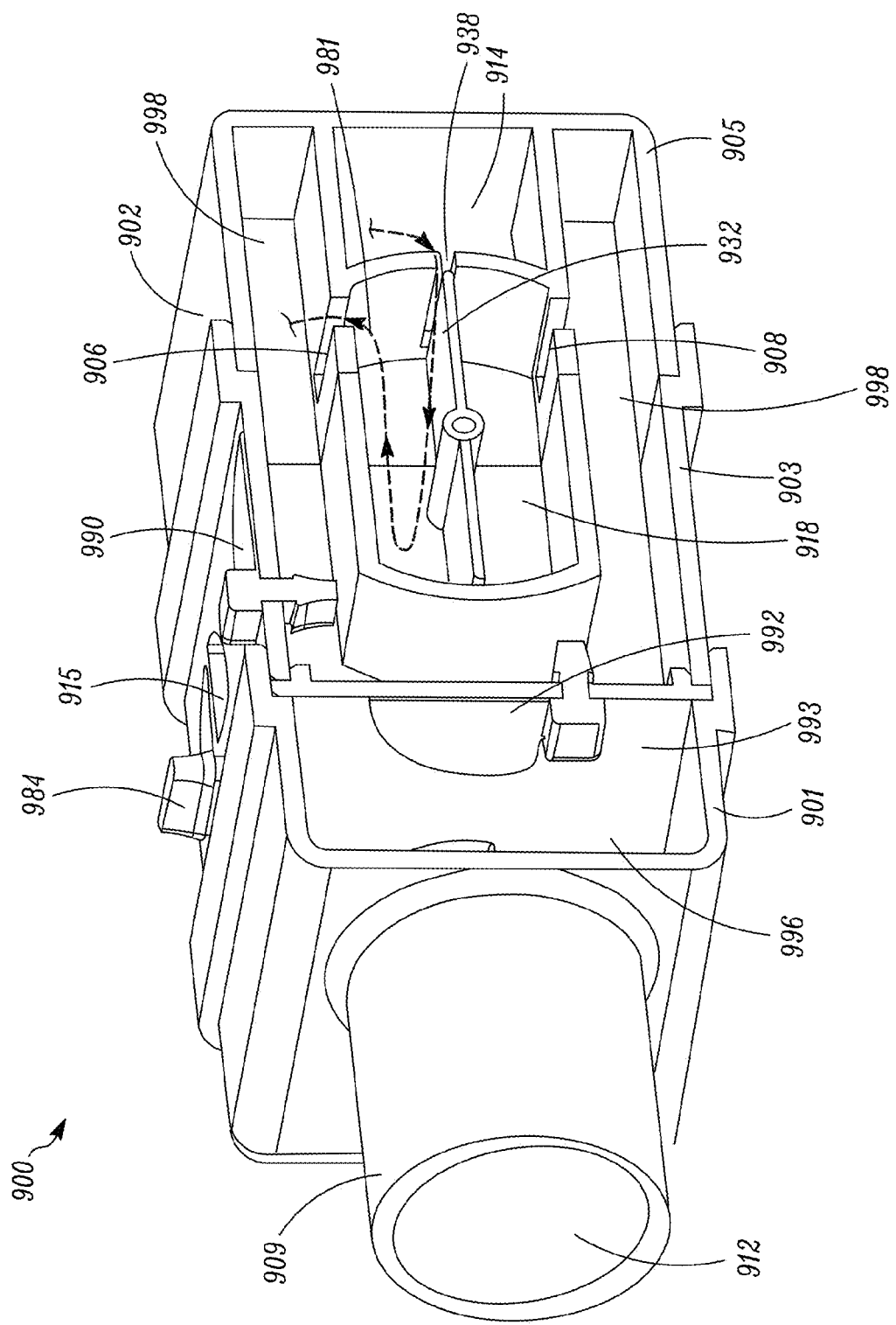
FIG. 69 is a cross-sectional perspective view taken along line II in FIG. 66 of the respiratory treatment device shown with the internal components of the device.

Referring now to FIGS. 68 and 69, cross-sectional perspective views are shown taken along lines I and II, respectively, in FIG. 66. The respiratory treatment device 900 administers oscillating pressure therapy upon both inhalation and exhalation in a manner similar to that shown and described above with regards to the OPEP devices. As described in further detail below, the OPEP device 900 includes a plurality of chambers (i.e., more than one). Air transmitted through the first opening 912 of the housing 902, whether inhaled or exhaled, traverses a flow path that passes, at least in part, past a restrictor member 930 housed in a first chamber 914, and through a second chamber 918 which houses a vane 932 operatively connected to the restrictor member 930. In this regard, at least a portion of the flow path for both air exhaled into or inhaled from the first opening 912 is overlapping, and occurs in the same direction.

For example, an exemplary flow path 981 is identified in FIGS. 68 and 69 by a dashed line. Similar to the previously described OPEP devices, the restrictor member 930 is positioned in the first chamber 914 and is movable relative to a chamber inlet 904 between a closed position, where the flow of air through the chamber inlet 904 is restricted, and an open position, where the flow of air through the chamber 904 inlet is less restricted. After passing through the chamber inlet 904 and entering the first chamber 914, the exemplary flow path 981 makes a 180-degree turn, or reverses longitudinal directions (i.e., the flow path 981 is folded upon itself), whereupon the exemplary flow path 981 passes through an orifice 938 and enters the second chamber 918. As with the previously described OPEP devices, the vane 932 is positioned in the second chamber 918, and is configured to reciprocate between a first position and a second position in response to an increased pressure adjacent the vane, which in turn causes the operatively connected restrictor member 930 to repeatedly move between the closed position and the open position. Depending on the position of the vane 932, air flowing along the exemplary flow path 981 is directed to one of either a first chamber outlet 906 or a second chamber outlet 908. Consequently, as inhaled or exhaled air traverses the exemplary flow path 981, pressure at the chamber inlet 904 oscillates.

The oscillating pressure at the chamber inlet 904 is effectively transmitted back to a user of the respiratory treatment device 900, i.e., at the first opening 912, via a series of chambers. As seen in FIGS. 68 and 69, the respiratory treatment device includes a first additional chamber 996, a second additional chamber 997, and a third additional chamber 998, which are described in further detail below.

The mouthpiece 909 and the first additional chamber 996 are in communication via the first opening 912 in the housing 902. The first additional chamber 996 and the second additional chamber 997 are separated by the manifold plate 993, and are in communication via the exhalation passage 994. The one-way valve 991 mounted adjacent to the exhalation passage 994 is configured to open in response to air exhaled into the first opening 912, and close in response to air inhaled through the first opening 912.

The first additional chamber 996 and the third additional chamber 998 are also separated by the manifold plate 993, and are in communication via the inhalation passage 995. The one-way valve 992 mounted adjacent to the inhalation passage 995 is configured to close in response to air exhaled into the first opening 912, and open in response to air inhaled through the first opening 912.

Air surrounding the respiratory treatment device 900 and the second additional chamber 997 are in communication via the third opening 915 in the housing 902. The one-way valve 984 is configured to close in response to air exhaled in to the first opening 912, and open in response to air inhaled through the first opening 912.

Air surrounding the respiratory treatment device 900 and the third additional chamber 998 are in communication via the second opening 913 in the housing 902. The one way-valve 990 mounted adjacent the second opening 913 is configured to open in response to air exhaled into the first opening 912, and close in response to air inhaled through the first opening 912. The third additional chamber 998 is also in communication with the second chamber 918 via the first chamber outlet 906 and the second chamber outlet 908.

Figure 70:
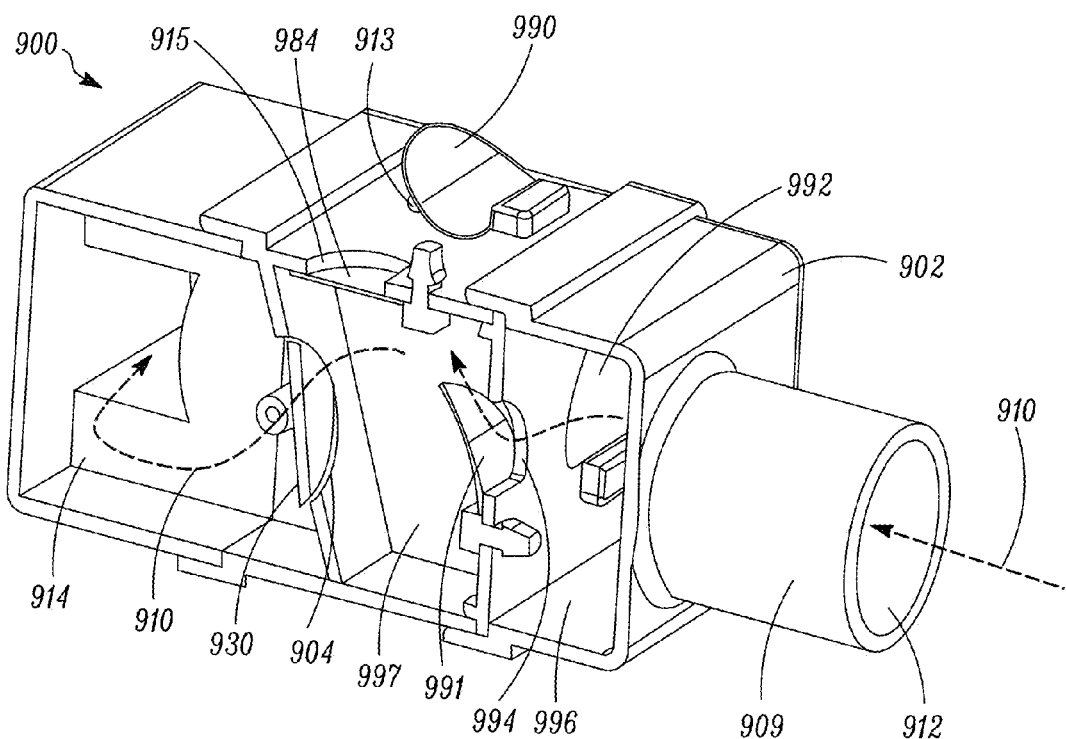
FIG. 70 is a different cross-sectional perspective view taken along line I in FIG. 66 of the respiratory treatment device, showing a portion of an exemplary exhalation flow path.
Figure 71:
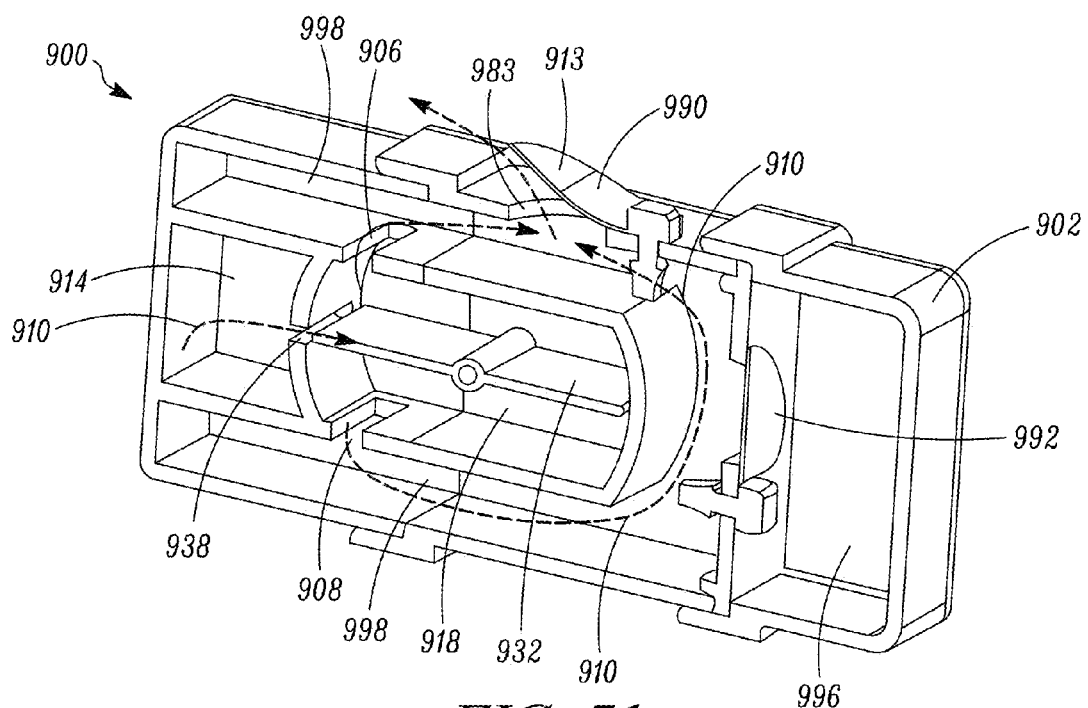
FIG. 71 is a different cross-sectional perspective view taken along line II in FIG. 66, showing a portion of an exemplary exhalation flow path.

Referring now to FIGS. 70-71, cross-sectional perspective views taken along lines I and II, respectively, of FIG. 66, illustrate an exemplary exhalation flow path 910 formed between the first opening 912, or the mouthpiece 909, and the second opening 913. In general, upon exhalation by a user into the first opening 912 of the housing 902, pressure builds in the first additional chamber 996, causing the one-way valve 991 to open, and the one-way valve 992 to close. Exhaled air then enters the second additional chamber 997 through the exhalation passage 994 and pressure builds in the second additional chamber 997, causing the one-way valve 984 to close and the restrictor member 930 to open. The exhaled air then enters the first chamber 914 through the chamber inlet 904, reverses longitudinal directions, and accelerates through the orifice 938 separating the first chamber 914 and the second chamber 918. Depending on the orientation of the vane 932, the exhaled air then exits the second chamber 918 through one of either the first chamber outlet 906 or the second chamber outlet 908, whereupon it enters the third additional chamber 998. As pressure builds in the third additional chamber 998, the one-way valve 990 opens, permitting exhaled air to exit the housing 902 through the second opening 913. Once the flow of exhaled air along the exhalation flow path 910 is established, the vane 932 reciprocates between a first position and a second position, which in turn causes the restrictor member 930 to move between the closed position and the open position, as described above with regards to the OPEP devices. In this way, the respiratory treatment device 900 provides oscillating therapy upon exhalation.

Figure 72:
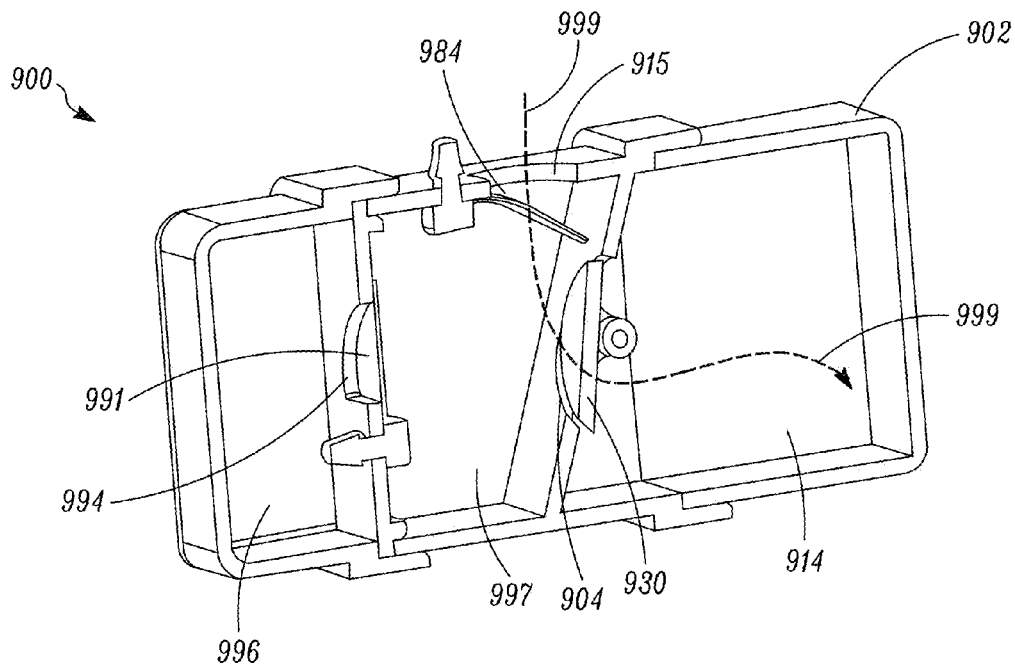
FIG. 72 is another cross-sectional perspective view taken along line I in FIG. 66, showing a portion of an exemplary inhalation flow path.
Figure 73:
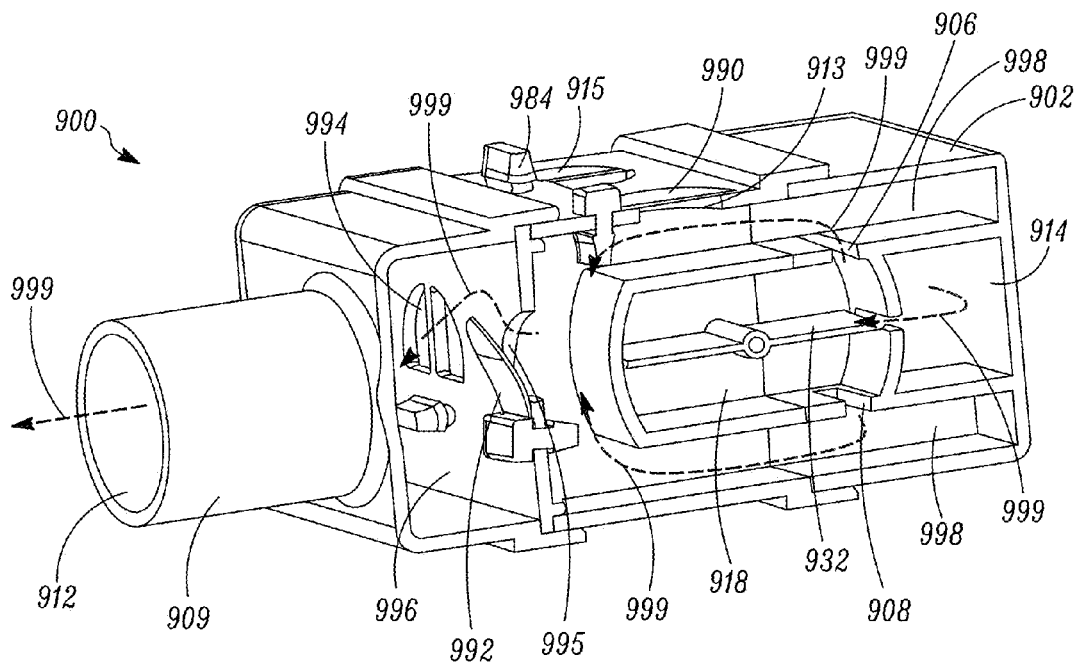
FIG. 73 is another cross-sectional perspective view taken along line II in FIG. 66, showing a portion of an exemplary inhalation flow path; and, FIG. 74 is a front perspective view of the OPEP device of FIG. 48, connected with an exemplary aerosol delivery device in the form of a nebulizer.

Referring now to FIGS. 72-73, different cross-sectional perspective views taken along lines I and II, respectively, of FIG. 66, illustrate an exemplary inhalation flow path 999 formed between the third opening 915 and the first opening 912, or the mouthpiece 909. In general, upon inhalation by a user through the first opening 912, pressure drops in the first additional chamber 996, causing the one-way valve 991 to close, and the one-way valve 992 to open. As air is inhaled from the third additional chamber 998 into the first additional chamber 996 through the inhalation passage 995, pressure in the third additional chamber 998 begins to drop, causing the one-way valve 990 to close. As pressure continues to drop in the third additional chamber 998, air is drawn from the second chamber 918 through the first chamber outlet 906 and the second camber outlet 908, As air is drawn from the second chamber 918, air is also drawn from the first chamber 914 through the orifice 938 connecting the second chamber 918 and the first chamber 914. As air is drawn from the first chamber 914, air is also drawn from the second additional chamber 997 through the chamber inlet 904, causing the pressure in the second additional chamber 997 to drop and the one-way valve 984 to open, thereby permitting air to enter the housing 902 through third opening 915. Due to the pressure differential between the first additional chamber 996 and the second additional chamber 997, the one-way valve 991 remains closed. Once the flow of inhaled air along the inhalation flow path 999 is established, the vane 932 reciprocates between a first position and a second position, which in turn causes the restrictor member 930 to move between the closed position and the open position, as described above with regards to the OPEP devices. In this way, the respiratory treatment device 900 provides oscillating therapy upon inhalation.

Figure 74:
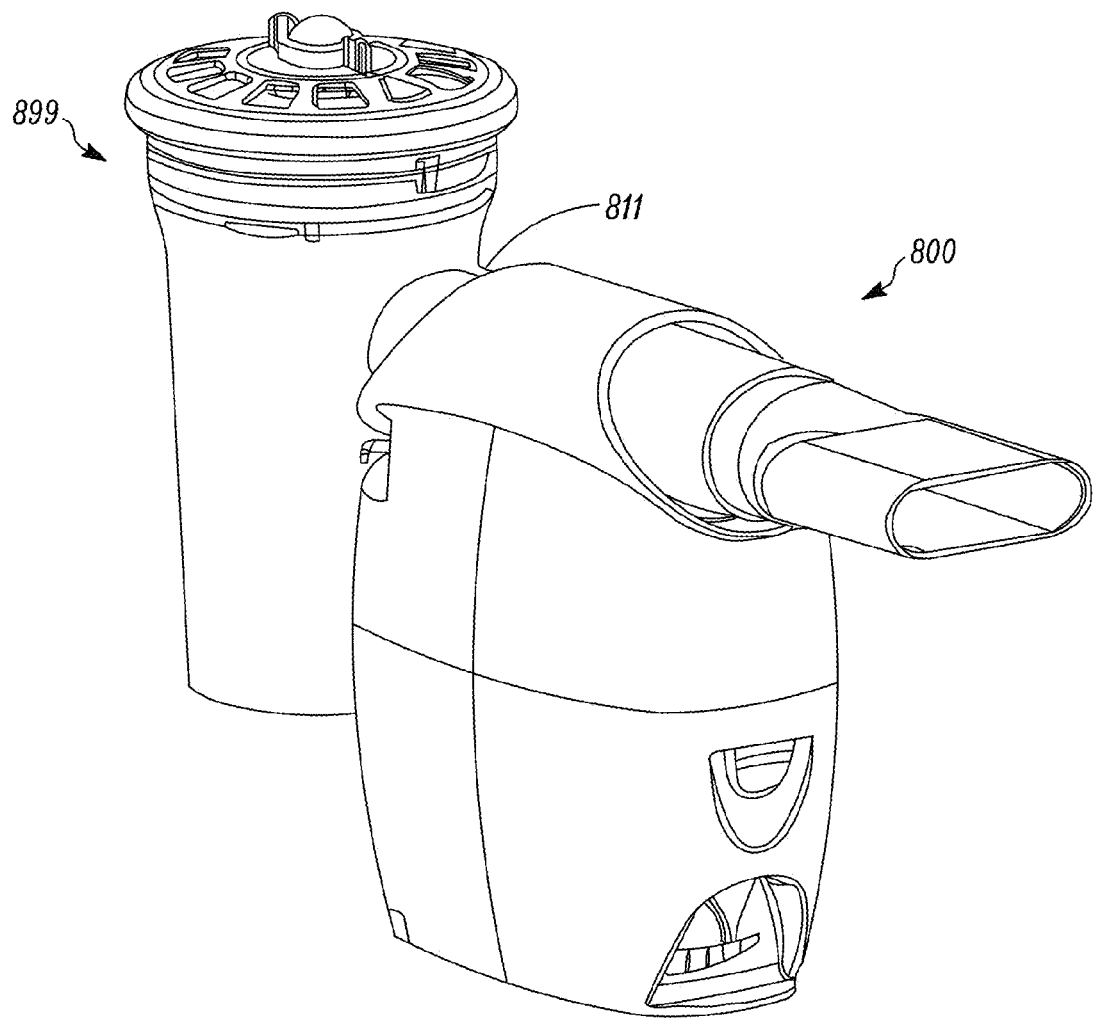

Referring now to FIG. 74, a front perspective view is shown of the OPEP device 800 connected with an aerosol delivery device in the form of a nebulizer 899 via the inhalation port 811. The system comprising the OPEP device 800 connected to the nebulizer 899 is configured to provide both oscillating pressure therapy and aerosol therapy, as described above. The combination of the OPEP device 800 and the nebulizer 899, however, is exemplary. Alternative combinations of the OPEP devices described herein and aerosol delivery devices, such as those identified above, are also envisioned.

Those skilled in the art will appreciated that the various concepts described above with regards to a particular embodiment of an OPEP device may also be applied to any of the other embodiments described herein, even though not specifically shown or described with regards to the other embodiments. For example, any one of the embodiments described herein may include a variable nozzle, an inhalation port adapted for use with an aerosol delivery device for the administration of aerosol therapy, an adjustment mechanism for adjusting the relative position of the chamber inlet and/or the permissible range of movement by a restrictor member, a chamber inlet bypass, one or more control ports, etc.

Although the foregoing description is provided in the context of an OPEP device, it will also be apparent to those skilled in the art will that any respiratory device may benefit from various teachings contained herein. The foregoing description has been presented for purposes of illustration and description, and is not intended to be exhaustive or to limit the inventions to the precise forms disclosed. It will be apparent to those skilled in the art that the present inventions are susceptible of many variations and modifications coming within the scope of the following claims.

Exemplary Implementations

In one implementation, a respiratory treatment device includes a housing enclosing at least one chamber, a chamber inlet configured to receive exhaled air into the at least one chamber, and at least one chamber outlet configured to permit exhaled air to exit the at least one chamber. An exhalation flow path is defined between the chamber inlet and the at least one chamber outlet, and a restrictor member is positioned in the exhalation flow path, the restrictor member being moveable between a closed position, where a flow of exhaled air through the chamber inlet is restricted, and an open position, where the flow of exhaled air through the chamber inlet is less restricted. An orifice is positioned along the exhalation flow path through which the exhaled air passes, and a vane is positioned adjacent the orifice, the vane being operatively connected to the restrictor member, and configured to reciprocate between a first position and a second position in response to an increased pressure adjacent the vane. Additionally, the restrictor member moves between the closed position and the open position in response to the vane reciprocating between the first position and the second position.

The restrictor member may be positioned in a first chamber, and the vane may be positioned in a second chamber. The orifice may connect the first chamber and the second chamber. A size of the orifice may be configured to change in response to the flow of exhaled air through the orifice. The restrictor member may be a butterfly valve. The vane may be operatively connected to the restrictor member by a shaft. A face of the restrictor member may be rotatable about an axis of rotation, and the face of the restrictor member may be radially offset from the axis of rotation. The face of the restrictor member may also have a greater surface area positioned on one side of the shaft than on the other side of the shaft. An orientation of the chamber inlet may be selectively adjustable. A chamber inlet bypass may be configured to permit exhaled air into the at least one chamber without passing through the chamber inlet. A control port may be configured to permit exhaled air to exit the respiratory treatment device prior to entering the at least one chamber. A control port may also be configured to permit exhaled air to exit the first chamber. An inhalation port may be in fluid communication with a user interface, and a one-way valve may be configured to permit air to flow through the inhalation port to the user interface upon inhalation. The inhalation port may also be configured to receive an aerosol medicament from an aerosol delivery device. The exhalation flow path may be folded upon itself.

In another implementation, a method of performing OPEP therapy includes receiving a flow of exhaled air along an exhalation flow path defined between an inlet and an outlet of a respiratory treatment device, directing the flow of exhaled air toward a vane, reciprocating the vane between a first position and a second position in response to the flow of exhaled air, and, moving a restrictor member in response to the reciprocal movement of the vane between a closed position, where a flow of exhaled air through the chamber inlet is restricted, and an open position, where the flow of exhaled air through the chamber inlet is less restricted.

In another implementation, a method of performing OPEP therapy includes receiving a flow of exhaled air along an exhalation flow path defined between an inlet and an outlet of a respiratory treatment device, accelerating the flow of exhaled air through an orifice positioned along the exhalation flow path, reciprocating a vane adjacent the orifice between a first position and a second position in response to the flow of exhaled air through the orifice, and, moving a restrictor member in response to the reciprocal movement of the vane between a closed position, where the flow of exhaled air along the exhalation flow path is restricted, and an open position, where the flow of exhaled air along the exhalation flow path is less restricted. The method may also include changing a size of the orifice in response to the flow of exhaled air through the orifice.

What is claimed is:

1. A respiratory treatment device, comprising:
   a housing enclosing at least one chamber;
   a chamber inlet configured to receive exhaled air into the at least one chamber;
   a mouthpiece in communication with the chamber inlet;
   a first aperture formed in the mouthpiece;
   a first regulator moveable relative to the first aperture to selectively block a cross-sectional area of the first aperture, wherein the first regulator is moveable relative to the first aperture in a first direction to selectively decrease the cross-sectional area of the first aperture, and movable in a second direction to selectively increase the cross-sectional area of the first aperture;
   a flow path defined between the mouthpiece and the first aperture, wherein the flow path does not pass through the chamber inlet; and,
   a second aperture formed in the at least one chamber;
   a second regulator moveable relative to the second aperture to selectively block a cross-sectional area of the second aperture, wherein the second regulator is moveable relative to the second aperture in a first direction to selectively decrease the cross-sectional area of the second aperture, and movable in a second direction to selectively increase the cross-sectional area of the second aperture;
   wherein the mouthpiece is in fluid communication through the first aperture with air surrounding the device.

2. The respiratory treatment device of claim 1, wherein the first aperture is formed in the mouthpiece between a patient port and the chamber inlet.

3. The respiratory treatment device of claim 1, wherein an exhalation flow path is defined between the mouthpiece and the aperture.

4. The respiratory treatment device of claim 1, wherein the first regulator translates relative to the first aperture between an open position and a closed position.

5. The respiratory treatment device of claim 4, wherein in the open position, the first regulator is not positioned in the cross-sectional area of the first aperture.

6. The respiratory treatment device of claim 1, further comprising:
   a chamber outlet configured to permit exhaled air to exit the at least one chamber; and,
   an exhalation flow path defined between the mouthpiece and the chamber outlet;
   wherein the second aperture is positioned along the exhalation flow path after the chamber inlet.

7. The respiratory treatment device of claim 6, further comprising a restrictor member positioned along the exhalation flow path, the restrictor member moveable in response to a flow of air along the exhalation flow path between a closed position, where the flow of air along the exhalation flow path is restricted, and an open position, where the flow of air along the exhalation flow path is less restricted.

8. The respiratory treatment device of claim 1, wherein the respiratory treatment device is an oscillating positive expiratory pressure treatment device.

9. The respiratory treatment device of claim 1, wherein an inhalation flow path is defined between the patient port and the first aperture.

10. A respiratory treatment device, comprising:
    a housing enclosing a chamber;
    a patient port for transmitting air exhaled from the patient into the chamber and air inhaled by the patient;
    a chamber outlet configured to permit exhaled air to exit the chamber;
    an exhalation flow path defined between the patient port and the chamber outlet;
    a restrictor member positioned in the chamber along the exhalation flow path, the restrictor member moveable in response to the flow of air along the exhalation flow path between a closed position, where the flow of air along the exhalation flow path is restricted, and an open position, where the flow of air along the exhalation flow path is less restricted; and,
    a first aperture positioned along the exhalation flow path prior to the restrictor member;
    a first regulator moveable relative to the aperture to selectively block a cross-sectional area of the aperture, wherein the regulator translates relative to the aperture in a first direction to selectively decrease the cross-sectional area of the aperture, and translates in a second direction to selectively increase the cross-sectional area of the aperture;
    a second aperture formed in the chamber;
    a second regulator moveable relative to the second aperture to selectively block a cross-sectional area of the second aperture, wherein the second regulator is moveable relative to the second aperture in a first direction to selectively decrease the cross-sectional area of the second aperture, and movable in a second direction to selectively increase the cross-sectional area of the second aperture;
    wherein the patient port is in fluid communication through the first aperture with air surrounding the device.

11. The respiratory treatment device of claim 10, wherein the first aperture is formed in the housing.

12. The respiratory treatment device of claim 10, wherein the first aperture is positioned along the exhalation flow path prior to a chamber inlet configured to permit exhaled air to enter the chamber.

13. The respiratory treatment device of claim 10, further comprising a flow path defined between the patient port and the first aperture, wherein the flow path does not pass through the chamber.

14. The respiratory treatment device of claim 10, wherein the first regulator translates relative to the first aperture between an open position and a closed position.

15. The respiratory treatment device of claim 14, wherein in the open position, the first regulator is not positioned in the cross-sectional area of the first aperture.

16. The respiratory treatment device of claim 10, wherein an inhalation flow path is defined between the patient port and the first aperture.

17. A method of performing respiratory treatment, the method comprising:
    passing a flow of exhaled air along an exhalation flow path defined between a patient port and an outlet of an oscillating positive expiratory pressure device;
    moving a restrictor member in response to the flow of exhaled air between a closed position, where the flow of exhaled air along the exhalation flow path is restricted, and an open position, where the flow of exhaled air along the exhalation flow path is less restricted; and, selectively moving a first regulator relative to a first aperture positioned along the exhalation flow path prior to the restrictor member, wherein the first regulator moves relative to the first aperture in a first direction to selectively decrease a cross-sectional area of the first aperture, and moves in a second direction to selectively increase the cross-sectional area of the first aperture;

selectively moving a second regulator relative to a second aperture positioned along the exhalation flow path after the restrictor member, wherein the second regulator moves relative to the second aperture in a first direction to selectively decrease a cross-sectional area of the second aperture, and moves in a second direction to selectively increase the cross-sectional area of the second aperture.

18. The method of claim 17, wherein the patient port is in fluid communication through the first aperture with air surrounding the device.

19. The method of claim 17, further comprising permitting the flow of exhaled air through the first aperture.

20. The method of claim 17, further comprising permitting a flow of air along an inhalation flow path between the first aperture and the patient port.

21. The method of claim 17, wherein the first regulator translates relative to the first aperture between an open position and a closed position, wherein in the open position, the first regulator is not positioned in the cross-sectional area of the first aperture.

* * * * *